(12) United States Patent
Issa

(10) Patent No.: US 6,783,933 B1
(45) Date of Patent: Aug. 31, 2004

(54) CACNA1G POLYNUCLEOTIDE, POLYPEPTIDE AND METHODS OF USE THEREFOR

(75) Inventor: Jean-Pierre Issa, Houston, TX (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/398,522

(22) Filed: Sep. 15, 1999

(51) Int. Cl.[7] .......................... C07H 21/04; C12Q 1/68
(52) U.S. Cl. .......................... 435/6; 435/91.2; 536/23.1
(58) Field of Search .............................. 435/6; 536/23.1

(56) References Cited

U.S. PATENT DOCUMENTS

| 5,501,964 A | | 3/1996 | Wigler et al. ............... 435/91.2 |
| 5,552,277 A | * | 9/1996 | Nelson ........................... 435/6 |
| 5,756,668 A | * | 5/1998 | Baylin ......................... 530/350 |
| 5,786,146 A | | 7/1998 | Herman et al. ................. 435/6 |
| 5,912,147 A | | 6/1999 | Stoler et al. ............... 435/91.2 |

FOREIGN PATENT DOCUMENTS

| WO | WO 96/35704 | 11/1996 |
| WO | WO 97/45560 | 12/1997 |

OTHER PUBLICATIONS

Baylin et al "Alterations in DNA methylation: A fundamental aspect of neoplasia" Advances in Cancer Research, vol. 72, p. 141–196, 1998.*
Toyota, et al., Methylation profiling in acute myeloid leukemia. BLOOD. May 2001, vol. 97 No. 9, pp. 2823–2828.*
Moinova et al. "HLTF gene silencing in human colon cancers". PNAS. vol. 99, No. 7, pp. 4562–4567, Apr. 2, 2002.*
Kazuhiro et al. "Aberrant methylation of multiple genes and clinicopatological features in oral squamous cell carcinoma". Clinical Cancer Research, vol. 8, No. 10, pp. 3164–3171, Oct. 2002.*
Shen L, et al, "DNA methylation and environmental exposures in human hepatocellular carcinoma", J Natl Cancer Inst, vol. 94, No. 10, 755–61, May 15, 1994 (Abstract only).
EMBL; "Homo sapiens T–type calcium channel alpha 1 G (CACNA1G) mRNA, partial cds.", Database EBI Online!, Jun. 3, 1999 (Database accession No. AF124351 XP–002223698).
"Voltage–dependent T–type calcium channel alpha–1 G subunit (NBR13)", Database EBI Online!, Jul. 15, 1999, (Database accession No. 043497 XP–002223697).
Mittman, Scott et al., "Structure and alternative splicing of the gene encoding alphaII, a human brain T calcium channel alpha1 subunit" Neuroscience letters vol. 269, No. 3, 121–124, Jul. 1999.
Mittman, S. et al., "Structure and alternative sicing of the genes encoding the human brain T Ca2= channel subunits alpha1 g and alpha11" Society for Neuroscience Abstracts, vol. 25, No. 1/2, 197, Oct. 1999.

Ueki, Takashi et al., "Hypermethylation of Multiple Genes in Pancreatic Adenocarcinoma", Cancer Research, vol. 60, 1835–1839, Apr. 1, 2000.
Strathdee, Gordon, et al., "Primary Ovarian Carcinomas Display Multiple Methylator Phenotypes Involving Known Tumor Suppressor Genes", American Journal of Pathology, vol. 158, No. 3, 1121–1127, Mar. 2001.
Rashid, Asif et al., "CpG Island Methylation in Colorectal Adenomas", American Journal of Pathology, vol. 159, No. 3, 1129–1135, Sep. 2001.
On–on Chan, Annie et al., "Concordant CpG Island Methylation in Hyperplastic Polyposis", American Journal of Pathology, vol. 160, No. 2, 529–539, Feb. 2002.
West, et al., "Hypomethylation of the Amyloid Precursor Protein Gene in the Brain of an Alzheimer's Disease Patient" Journal of Molecular Neuroscience 6 (2):141–146 (1995).
Zrihan–Licht, et al., "DNA Methylation Status of the MUC1 Gene Coding for a Breast–Cancer–Associated Protein" Int. J. Cancer 62:245–251 (1995).
Merlo and Herman, "DNA Methylation and Inactivation of Tumor Suppressor Genes" In: Hereditary Cancer, Second International Research Conference on Familial Cancer Edited by Hj. Miller, et al., 152–160 (1996).
Ahuja, et al., "Association between CpG island methylation and microsatellite instability in colorectal cancer" Proceedings of the American Association for Cancer Research 38:360–361 (1997).
Perez–Reyes et al., "Molecular characterization of a neuronal low–voltage–activated T–type calcium channel," Nature 391:896–900 (1998).
Perez–Reyes et al., "Molecular Characterization of Two Members of the T–Type Calcium Channel Family," Annals New York Academy of Sciences 868:131–143 (1999).
Toyota et al., "Inactivation of CACNA1G, a T–type calcium channel gene, by aberrant methylation of its 5' CpG island in human tumors" Database Medline US Library of Medicine, AN AF124351 (1999).

* cited by examiner

Primary Examiner—Gary Benzion
Assistant Examiner—Jeanine Goldberg
(74) Attorney, Agent, or Firm—Gray Cary Ware & Freidenrich, LLP

(57) ABSTRACT

A novel T-type calcium channel (CACNA1G) is provided, as are polynucleotides encoding the same. CACNA1G has been implicated in cellular proliferative disorders. More specifically, it has been observed that the methylation state of specific regions within CpG island associated with the CACNA1G gene correlates with a number of cancerous phenotypes involving a variety of tissue and cell types. Also provided are methods for detecting cellular proliferative disorders by determining the methylation state of genes or regulatory regions associated therewith, including CACNA1G, as well as kits containing reagents for performing invention methods.

12 Claims, 11 Drawing Sheets

Figure 2

|  | Island 1 | | | | | | | Island 2 | | | | | Expression of |
|---|---|---|---|---|---|---|---|---|---|---|---|---|---|
| Methylation pattern | R1 | | R2 | | R3 | R4 | | R5 | R6 | R7 | R8 | | hCACNA1G |
|  | M | B | T | B | M | M | T | B | T | H | E | T | B | |
| 1 | ○ | ○ | ○ | ○ | ○ | ○ | ○ | ○ | ○ | ○ | ○ | ○ | ○ | ++ |
| 2 | ○ | ◔ | ○ | ◑ | ○ | ◔ | ◔ | ○ | ○ | ○ | ○ | ○ | ○ | +++ |
| 3 | ◕ | ● | ● | ● | ◔ | ◔ | ◔ | ○ | ○ | ○ | ○ | ● | ◑ | +++ |
| 4 | ◕ | ◑ | ● | ● | ◔ | ● | ● | ◔ | ◑ | ◐ | ● | ● | ◔ | 0 |
| 5 | ● | ◑ | ◑ | ● | ◔ | ◔ | ◔ | ○ | ◔ | ◔ | ◔ | ● | ◑ | 0→++ |

FIGURE 3A (SEQ ID NO:51) CACNA1G nucleotide sequence

```
CCTTTTCGTTCGCCCTCTCGGGGCGGCTTCGCCGAAGGTAGCGCCGAATCCGGCAACCGGAGCCTGGGCGCGAAGCGAAG
AAGCCGGAACAAAGTGAGGGGGAGCCGGCCGGCTGGCCCGGGAAGCCCCAGGGGCGCAGGGGAAGCGGGACTCGCGCCGG
GCGGGGTTTCCCTGCGCCCCGGCGCCCCGCGGGCAGCATGCCCCTGCGGGCAGGGGGAGCTGGGCTGAACTGGCCCTCCC
GGGGGCTCAGCTTGCGCCCTAGAGCCCACCAGATGTGCCCCCGCCGGGGCCCCCGGGTTGCGTGAGGACACCTCCTCTGA
GGGGCGCCGCTTGCCCCTCTCCGGATCGCCCGGGGCCCCGGCTGGCCAGAGGATGGACGAGGAGGAGGATGGAGCGGGCG
CCGAGGAGTCGGGACAGCCCCGGAGCTTCATGCGGCTCAACGACCTGTCGGGGGCCGGGGGCCGGCCGGGGCCGGGGTCA
GCAGAAAAGGACCCGGGCAGCGCGGACTCCGAGGCGGAGGGGCTGCCGTACCCGGCGCTGGCCCCGGTGGTTTTCTTCTA
CTTGAGCCAGGACAGCCGCCCGCGGAGCTGGTGTCTCCGCACGGTCTGTAACCCCTGGTTTGAGCGCATCAGCATGTTGG
TCATCCTTCTCAACTGCGTGACCCTGGGCATGTTCCGGCCATGCGAGGACATCGCCTGTGACTCCCAGCGCTGCCGGATC
CTGCAGGCCTTTGATGACTTCATCTTTGCCTTCTTTGCCGTGGAGATGGTGGTGAAGATGGTGGCCTTGGGCATCTTTGG
GAAAAAGTGTTACCTGGGAGACACTTGGAACCGGCTTGACTTTTTCATCGTCATCGCAGGGATGCTGGAGTACTCGCTGG
ACCTGCAGAACGTCAGCTTCTCAGCTGTCAGGACAGTCCGTGTGCTGCGACCGCTCAGGGCCATTAACCGGGTGCCCAGC
ATGCGCATCCTTGTCACGTTGCTGCTGGATACGCTGCCCATGCTGGGCAACGTCCTGCTGCTCTGCTTCTTCGTCTTCTT
CATCTTCGGCATCGTCGGCGTCCAGCTGTGGGCAGGGCTGCTTCGGAACCGATGCTTCCTACCTGAGAATTTCAGCCTCC
CCCTGAGCGTGGACCTGGAGCGCTATTACCAGACAGAGAACGAGGATGAGAGCCCCTTCATCTGCTCCCAGCCACGCGAG
AACGGCATGCGGTCCTGCAGAAGCGTGCCCACGCTGCGCGGGGACGGGGCGGTGCCCACCTTGCGGTCTGGACTATGA
GGCCTACAACAGCTCCAGCAACACCACCTGTGTCAACTGGAACCAGTACTACACCAACTGCTCAGCGGGGGAGCACAACC
CCTTCAAGGGCGCCATCAACTTTGACAACATTGGCTATGCCTGGATCGCCATCTTCCAGGTCATCACGCTGGAGGGCTGG
GTCGACATCATGTACTTTGTGATGGATGCTCATTCCTTCTACAATTTCATCTACTTCATCCTCCTCATCATCGTGGGCTC
CTTCTTCATGATCAACCTGTGCCTGGTGGTGATTGCCACGCAGTTCTCAGAGACCAAGCAGCGGGAAAGCCAGCTGATGC
GGGAGCAGCGTGTGCGGTTCCTGTCCAACGCCAGCACCCTGGCTAGCTTCTCTGAGCCCGGCAGCTGCTATGAGGAGCTG
CTCAAGTACCTGGTGTACATCCTTCGTAAGGCAGCCCGCAGGCTGGCTCAGGTCTCTCGGGCAGCAGGTGTGCGGGTTGG
GCTGCTCAGCAGCCCAGCACCCCTCGGGGGCCAGGAGACCCAGCCCAGCAGCAGCTGCTCTCGCTCCCACCGCCGCCTAT
CCGTCCACCACCTGGTGCACCACCACCACCACCATCACCACCACTACCACCTGGGCAATGGGACGCTCAGGGCCCCCCGG
GCCAGCCCGGAGATCCAGGACAGGGATGCCAATGGGTCCCGCCGGCTCATGCTGCCACCACCCTCGACGCCTGCCCTCTC
CGGGGCCCCCCCTGGTGGCGCAGAGTCTGTGCACAGCTTCTACCATGCCGACTGCCACTTAGAGCCAGTCCGCTGCCAGG
CGCCCCCTCCCAGGTCCCCATCTGAGGCATCCGGCAGGACTGTGGGCAGCGGGAAGGTGTATCCCACCGTGCACACCAGC
CCTCCACCGGAGACGCTGAAGGAGAAGGCACTAGTAGAGGTGGCTGCCAGCTCTGGGCCCCCAACCCTCACCAGCCTCAA
CATCCCACCCGGGCCCTACAGCTCCATGCACAAGCTGCTGGAGACACAGAGTACAGGTGCCTGCCAAAGCTCTTGCAAGA
TCTCCAGCCCTTGCTTGAAAGCAGACAGTGGAGCCTGTGGTCCAGACAGCTGCCCCTACTGTGCCCGGGCCGGGGCAGGG
GAGGTGGAGCTCGCCGACCGTGAAATGCCTGACTCAGACAGCGAGGCAGTTTATGAGTTCACACAGGATGCCCAGCACAG
CGACCTCCGGGACCCCCACAGCCGGCGGCAACGGAGCCTGGGCCCAGATGCAGAGCCCAGCTCTGTGCTGGCCTTCTGGA
GGCTAATCTGTGACACCTTCCGAAAGATTGTGGACAGCAAGTACTTTGGCCGGGGAATCATGATCGCCATCCTGGTCAAC
ACACTCAGCATGGGCATCGAATACCACGAGCAGCCCGAGGAGCTTACCAACGCCCTAGAAATCAGCAACATCGTCTTCAC
CAGCCTCTTTGCCCTGGAGATGCTGCTGAAGCTGCTTGTGTATGGTCCCTTTGGCTACATCAAGAATCCCTACAACATCT
TCGATGGTGTCATTGTGCTGAAGCTGGTGCGCTTCCTGCCGGCGCTGCAGGGGCAGCTGGTGGTGCTCATGAAGACCATGA
CGCCTGATGCGTGTGCTGAAGCTGGTGCGCTTCCTGCCGGCGCTGCAGGGGCAGCTGGTGGTGCTCATGAAGACCATGGA
CAACGTGGCCACCTTCTGCATGCTGCTTATGCTCTTCATCTTCATCTTCAGCATCCTGGGCATGCATCTCTTCGGCTGCA
AGTTTGCCTCTGAGCGGGATGGGGACACCCTGCCAGACCGGAAGAATTTTGACTCCTTGCTCTGGGCCATCGTCACTGTC
TTTCAGATCCTGACCCAGGAGGACTGGAACAAAGTCCTCTACAATGGTATGGCCTCCACGTCGTCCTGGGCGGCCCTTTA
TTTCATTGCCCTCATGACCTTCGGCAACTACGTGCTCTTCAATTTGCTGGTCGCCATTCTGGTGGAGGGCTTCCAGGCGG
AGGGAGATGCCAACAAGTCCGAATCAGAGCCCGATTTCTTCTCACCCAGCCTGGATGGTGATGGGGACAGGAAGAAGTGC
TTGGCCTTGGTGTCCCTGGGAGAGCACCCGGAGCTGCGGAAGAGCCTGCTGCCGCCCTCTCATCATCCACACGGCCGCCAC
ACCCATGTCGCTGCCCAAGAGCACCAGCCACGGGCCTGGGCGAGGCGCTGGGCCCTGCGTCGCGCCGCACCAGCAGCGCG
GGTCGGCAGAGCCTGGGCGGCCCACGAGATGAAGTCACCGCCCAGCGCCCGCAGCTCTCCGCACAGCCCCTGGAGCGCT
GCAAGCAGCTGGACCAGCAGGCGCTCCAGCCGGAACAGCCTCGGCCGTGCACCCAGCCTGAAGCGGAGAAGCCCAAGTGG
AGAGCGGCGGTCCCTGTTGTCGGGAGAAGGCCAGGAGAGCCAGGATGAAGAGGAGAGCTCAGAAGAGGAGCGGGCCAGCC
CTGCGGGCAGTGACCATCGCCACAGGGGGTCCCTGGAGCGGGAGGCCAAGAGTTCCTTTGACCTGCCAGACACACTGCAG
GTGCCAGGGCTGCATCGCACTGCCAGTGGCCGAGGGTCTGCTTCTGAGCACCAGGACTGCAATGGCAAGTCGGCTTCAGG
GCGCCTGGCCCGGGCCCTGCGGCCTGATGACCCCCACTGGATGGGGATGACGCCGATGACGAGGGCAACCTG
```

Figure 3B (SEQ ID NO:52)

```
MDEEEDGAGAEESGQPRSFMRLNDLSGAGGRPGPGSAEKDPGSA
DSEAEGLPYPALAPVVFFYLSQDSRPRSWCLRTVCNPWFERISMLVILLNCVTLGMFR
PCEDIACDSQRCRILQAFDDFIFAFFAVEMVVKMVALGIFGKKCYLGDTWNRLDFPIV
IAGMLEYSLDLQNVSPSAVRTVRVLRPLRAINRVPSMRILVTLLLDTLPMLGNVLLLC
FFVFFIFGIVGVQLWAGLLRNRCFLPENFSLPLSVDLERYYQTENEDESPFICSQPRE
NGMRSCRSVPTLRGDGGGGPPCGLDYEAYNSSSNTTCVNWNQYYTNCSAGEHNPFKGA
INFDNIGYAWIAIFQVITLEGWVDIMYFVMDAHSFYNFIYFILLIIVGSFFMINLCLV
VIATQFSETKQRESQLMREQRVRFLSNASTLASFSEPGSCYEELLKYLVYILRKAARR
LAQVSRAAGVRVGLLSSPAPLGGQETQPSSSCSRSHRRLSVHHLVHHHHHHHHYHLG
NGTLRAPRASPEIQDRDANGSRRLMLPPPSTPALSGAPPGGAESVHSFYHADCHLEPV
RCQAPPPRSPSEASGRTVGSGKVYPTVHTSPPPETLKEKALVEVAASSGPPTLTSLNI
PPGPYSSMHKLLETQSTGACQSSCKISSPCLKADSGACGPDSCPYCARAGAGEVELAD
REMPDSDSEAVYEFTQDAQHSDLRDPHSRRQRSLGPDAEPSSVLAFWRLICDTFRKIV
DSKYFGRGIMIAILVNTLSMGIEYHEQPEELTNALEISNIVFTSLFALEMLLKLLVYG
PFGYIKNPYNIFDGVIVVISVWEIVGQQGGGLSVLRTFRLMRVLKLVRFLPALQRQLV
VLMKTMDNVATFCMLLMLFIFIFSILGMHLFGCKFASERDGDTLPDRKNFDSLLWAIV
TVFQILTQEDWNKVLYNGMASTSSWAALYFIALMTFGNYVLFNLLVAILVEGFQAEGD.
ANKSESEPDFFSPSLDGDGDRKKCLALVSLGEHPELRKSLLPPLIIHTAATPMSLPKS
TSTGLGEALGPASRRTSSSGSAEPGAAHEMKSPPSARSSPHSPWSAASSWTSRRSSRN
SLGRAPSLKRRSPSGERRSLLSGEGQESQDEEESSEEERASPAGSDHRHRGSLEREAK
SSFDLPDTLQVPGLHRTASGRGSASEHQDCNGKSASGRLARALRPDDPPLDGDDADDE
GNL
```

FIGURE 4A

APOB CpG ISLAND (SEQ ID NO:105)

cccgggaggcgcccttttggaccttttgcaatcctggcgctcttgcagcctgggcttcctataaatggggtgcgggcgccggccgcgcattc
ccaccgggacctgcggggctgagtgcccttctcggttgctgccgctgaggagcccgcccagccagccagggccgcgaggccgaggcc
aggccgcagcccaggagccgccccaccgcagctggcgatggacccgccgaggcccgcgctgctggcgctgcctgcgctgctgctgct
gctgctggcgggcgccagggccggtgagtgcgcggccgctctgcgggcagcagaggggagcgggagggagccggcggaccgaggtt
ggccggggcagcctgggcctaggccagagggagggcagccacagggtccagggcgagtggggggattggaccagctggcggcccc
tgcaggctcaggatggggggcgcgggatggaggggctgaggagggggtctccggagcctgcctccctcctgaaaggtgaaacctgtgc
cggtggtcccccctgtcgggcccctagcacccgctgggaagacgtgggaagctc CACNA1G CpG ISLAND (SEQ ID NO:106)

cctgcggccctacgccaggaccccgcgccgaatactctgattcttcgggctccctccaagggagtcccaaagaccccaatggccaatagg
aaagtggggttcggtctgggcagcagtctgattggctccagccttcgggagcggacccaggggcaaggggaggggagaggggcggtcct
gggttttggggtgggaatcggattccagctgtggttctctccctgcgctcccgcccgcactgccacggcggacggccaatgggcgcgcgg
ctcggggccggcggcgtccggcgattggctgcggggctgtctggggggcggggccgaggcttgaagttgaagtgagggatccagctgtg
gtgtgcgcggggctcctcgccgccgctttcgctcgctcgctccgcgtctcggccggaggaggaggctgtggcgccggcgacagctacg
gcagcggcagccaccgcggcggctgcggcggcggcatctccgcctccactcccgcccgggactgccccccactgtctcccgcccctc
ccggacagtgagcccgcggcggggcggggaaggagccgcccccaccccctccaagcccaccccctaaagagatcctcctcccctcc
cccgccgcctggcgcggagccgggacgatgctgacccctagatccggctccagctgcgccgcgggaagaggggggcgcccctccccg
gaccccccgccctccgccgctgcccccctttcgttcgccctctcgggggcggcttcgccgaaggtagcgccgaatccggcaaccggagcct
gggcgcgaagcgaagaagccggaacaaagtgaggggggagccggccggctggcccgggaagcccccaggggcgcagggggaagcgg
gactcgcgccgggcggggtttccctgcgccccggcgccccgcgggcagcatgcccctgcgggcagggggagctgggctgaactggc
cctcccgggggctcagcttgcgccctagagcccaccagatgtgccccgccggggccccgggttgcgtgaggacacctcctctgagg
Ggcgccgcttgcccctctccggatcgcccggggcccggctggccagaggatggacgaggaggaggatggagcgggcgccgagga
gtcgggacagccccggagcttcatgcggctcaacgacctgtcggggccgggggcggccggggccgggggtcagcagaaaaggaccc
gggcagcgcggactccgaggcggaggggctgccgtacccggcgctggccccggtggttttcttctacttgagccaggacagccgcccg
cggagctggTgtctccgcacggtctgtaacccatatccttcggggcacgacggccaggcgcggggtcagaaggggggacgggccgcac
cgccgggggtcggggggggaagaagacccaccgccaggtgagtcgaagtgagcccggagggtaggcggatggggggggggctgcc
agggaggggaggggggcaccagagtggggagcggagacgcgagcaggtctcgtcggtaacccgggcttacccccacctgcgtacacaca
cctcagtcttcctggggttgggggggtggggatccaggccaggagaagagagctgtgccccgctggctcgcagctggacgccctccagat
gtggtcaggggagggtcgtcatcctccagatgtgggaagcttcgggagcctgggagctgtactctgcccgcgccggttagcgagctgggt
ttggtttccgagtttggtgggggggtgggtggggcggtggggaggaagctgcggggacggaggaggggggaccgcaatctcctgggtt
tccctccttccccgccccaaagtttgcggcggattctagatgttgggggggcggggaccaggtcctggcccacctcacccccccacctcgcg
ggttggaggcacaacaaggagattccggcggcggctgatgtcaggggcgcagaatgagaacaagatgtggtggaggggagctgtctgc
ccccggagctgggagtggagcccctttccgctagagcccagtgccgcgggtgcctcctacccgatctccattcgatgc

FIGURE 4B

CDX2 CpG Island (SEQ ID NO:107)
ctcgttaatcacggaagccgccggcctggggctccgcacgccagcctgtgcgggtcttccccgcctctgcagcctagtgggaaggaggt
gggaggaaagaaggaagaaagggagggagggaggaggcaggccagagggagggaccgcctcggaggcagaagagccgcgagg
agccagcggagcaccgcgggctggggcgcagccacccgccgctcctcgagtcccctcgcccctttcccttcgtgcccccggcagcctc
cagcgtcggtccccaggcagcatggtgaggtctgctcccggtccctcgccaccatgtacgtgagcta EGFR CpG Island (SEQ ID NO:108)
gtccgcggggaccgggtccagaggggcagtgctgggaacgcccctctcggaaattaactcctcagggcaccgctcccctcccatgcgcc
gccccactcccgccggagactaggtcccgcgggggccaccgtgtccaccgcctcgcggccgctggccttgggtcccgctgctggttct
cctccctcctcctcgcattctcctcctcctctgctcctcccgatccctcctccgccgcctggtccctcctcctcccgccctgcctcccgcgcctc
ggcccgcgcgagctagacgtccgggcagccccggcgcagcgcggccgcagcagcctcctcccccgcacggtgtgagcgcccgcc
gcgccgaggcggccggagtcccgagctagccccgcggccgccgccgcccagaccggacgacaggccacctcgtcgcgtccgcccg
agtccccgcctcgccgccaacgccacaaccaccgcgcacggcccctgactccgtccagtattgatcgggagagccggagcgagctctt
cggggagcagcgatgcgaccctccgggacggccggggcagcgctcctggcgctgctggctgcgctctgccCggcgagtcgggctctg
Gaggaaaagaaaggtaagggcgtgtctcgcggctcccgccgccccggatcgcgccccggaccccgcagcccgcccaaccgcacc
gcgcaccggcttcgcccgcgcccccgcccgtccttttcctgtttccttgagatcacgtgcgccgccgacccggggaccgcgggaggaacggg
acgtttcgttcttcggccgggagagtctggggcgggcggaggaggagacgcgtgggacaccgggctgcaggccaggcggggaacgg
ccgccgggacctccggcgccccgaaccgctcccaactttcttccctcactttccccgcccagctgcgcaggatcggcgtcagtgggcgaa
agccgggtgctggtgggcgcctggggccggggtcccgcacgggctccccgcgctgtcttcccagggcgcgacggggtcctggcgcgc
acccgagggccgctgcccacccgccgagactgcctgtttagggaagctgaggaaggaacccaaaaatacagcctccgctcggaccccg
cgggacaggcggctttctgagaggacctccccgcctccgcgctccgcgcaggtctcaaactgaagccggcgcccgccagcctggcccc
ggcccctctccaggtccccgcgatcctcgttcccagtgtgagtcgcagcctcgacctgggagctgggagaactcgtctaccaccacctg
cggctcccggggagggtggtgctggcggccggttagtttcctcgttggcaaaaggcaggtggggtccgacccgccccttgggcgcagac
cccggccgctcgcctcgcccggtgcgccctcgtcttgcctatccaagagtgcccccactcccgggaccccagctccctccgcgcccgc
gccgaaagccccaggctctccttcgatggccgcctcgcggagacgtccgggtctgctccacctgcagcccttcggtcgcgcctgggcttc
gcggtggagcgggacgcggctgtccggccactgcaggggggatcgcgggactcttgagcggaagccccg FIGURE 4C
FBN1 CpG Island (SEQ ID NO:109)

agagccgcgtctggagtgggctctcgacacccagggcaagtggggcggcagagccctctcctcggtcggcacagcagcctctgccgcggtcccgg
cctgcgacgcgcccagtcttagcctcccggcctccggcgtctgctgagtgtccggcgggagaggcgcagggagcgcgctaccgggaggcgcgggc
agcggggactggttttctctcgggccagggcctccggggcaaccgtctccagcgcgcattcttggtgcaggtggaacagctttctgctccggtagggctt
cacctatcgcgggagaggttaatctcggatctaaacctcgcagccgcagagcgggctaaaaccgctactccacctcttcccatttctcccctcccccacctc
aagacaaaaagtcccaggccgggcaggacctgatcacctctgcctcctcccactgcgctaatcctgcgagcgagaggccccgcaccgaggcggagg
ctgcaaagggggagtggaaagggaggatggatggggccgggggtggggtggtgatgagggcgacgaaggaggggggtgtcattttcttttcttttcttttt
ttaaaaaaagtatttctctcgcgagaaaccgctgcgcggacgatacttgaagaggtggggaaaggaggggggctgcgggagccgcggcagagactgtg
ggtgccacaagcggacaggagccacagctgGgacagctgcgagcggagccgagcagtggctgtagcggccacgactgggagcagccgccgccg
cctcctcgggagtcggagccgccgcttctccagtgggtgcagccggggtccgacggggtcgggcggcaccggggctggagctgcggccacgga
ggcttttgcgtttgcgccgnnngagggcagggacagggactggggtgagggcgtgtcccggaacgtccaacgtggncgctggaccctcccctgcct
gacagcttcctgnccggggcttcttggtgccggnccggcgtcagatgttcgggggcggtgcatcgcccggagtcggcggggacggcgcggctgctt
ccagctggcggagagggcaggctgaggagtggggcgttcagagcgcgcatcgcgcgcaattcgtgccgctaaaaaaaataaaaaccagagagctcgc
ccggggcttaggaccgctggggatatgggtactttgcgccgcgctcttctggcggggcccgggaggcgagggattggccggggctgctgcgccggg
gcctgggcttccagccagctgtggaccaaacggtcttccccttacccaaattaactgcgccacaggcggccgacnggttgggcttttgggaatggggacc
gcgagcttcagcatcccgatgccctgaaagtctcccccgcctcggggatttgtctctgtgttgcagctggcaggggccgcctgaagtgggagcagcgcct
ggagaaggcgggaggagcccggcccgggggacgggcggcgggatagcgggaccccggcggcgcggtgcgcttcagggcgcagcggcggccg
cagaccgagccccgggcgcggcaagaggcggcgggagccggtggcggctcggcatcatgcgtcgagggcgtctgctggagatcgccctgggattt
accgtgcttttagcgtcctacacgagccatggggcggacgccaatttggaggctgggaacgtgaaggaaaccagagccagtcgggccaagagaaga
ggcggtggaggacacgacgcgcttaaagggtaaaggaaccggttccctc

GPR37 (SEQ ID NO:110)

Tcccgccccgcaccgccccctagcccgggctcggggacctgtcaggctggtttcgacagctggggaattaacctgtcccgcccatccctagcctcgag
ccgcgcaggctccgcgcctccgcccttgttccctcccagctcctccgagtggaagccgctacaaatggcttgaatgaaacgtgtgtgggtttagtgagtg
gtgaaccaccagggatcccgtctcccacaaaccagtatctctccgaggaggaggcgaaggagtgggaggaggcaacgagccgagagtcgagctt
cgcgggcgcgcgcagcggctggagcgcgggggcgaggccgggccacctcccctccccggccgcgcactgcctggcccgcggcggttccaggca
ccaccctcccgtccgggctgagcccgctgtggcagtgactagctcccgcggctagcggcactgtccaccgacgagcggcgccctcttctccccttct
ccccacgatttccttctctgcggcggcacgccgtccagcagcctgcttcgccccgtcgtcaactttgagctggaggagaagcaactttggcagtggccgc
gggggttggaatcccgcttctcctcggcagcagtaggctcgcaagtcgctggggttaggtggggcaagagtttcgccggcgcatcagcgctgcttcggac
tgtttgcaacgtgttccagcgagctgggagcggggttgtgactgcgagtcgtctgggggaggggggacttgtttttcttttcctctagagacctcggcttgca
actggatcaaacgctgtcgaaa HSPA6 CpG Island (SEQ ID NO:111)

tgtattcgcatggtaacatatcttcggtcttcctgccgctgggctctcagcggccctccaaggcagcccgcaggcccgtgctcgcctcagggatcctccac
agccccggggagaccttgcctctaaagttgctgcttttgcagctctgccacaaccgcgcgtcctcagagccagccgggaggagctagaaccttccccgc
gtttctttcagcagccctgagtcagaggcgggctggccttgcaagtagccgcccagccttcttcggtctcacggaccgatccgcccgaaccttctcccgg
ggtcagcgccgccgctgcgccgcccgctgactcagcccgggcgggcgggcgggaggctctcgactgggcgggaaggtgcgggaaggttcgcgg
cggcggggtcggggaggtgcaaaaggatgaaaagcccgtggacgggagctgagcagatccggccgggctggcggcagagaaaccgcagggagag
cctcactgctgagcgccccctcgacgcgggcggcagcagcctccgtggcctccagcatccgacaa

FIGURE 4D

IQGAP2 CpG Island (SEQ ID NO:112)

Agagttcacttttacttcagtgtcagcgcgcggcggccgtggctggctctggcgagagagcaccgagggagtgggtcgcagatcttcgg
gcggctaggggaaatcggcgagaggcgggatccgagcgcgccggcggggcgcagagcccgcgagcctggccagcgagggtagcc
gcgggggcgcgcccgggcgggccccggagacgcgcaggatgccacacgaagagctgccgtcgctgcagagacccgctatgg
ctctattgtggacgatgaaa KL CpG Island (SEQ ID NO:113)

ctcgaaagaggggcgcgggtgggcgcgtctccccgcgagcatctcacctaaggggaatcccttcagcgcacggcgaagttccccctc
ggctgtcccacctggcagtccctctaggatttcggccagtccctaattggctccagcaatgtccagccggagcttctttgggcctccgagtgg
gagaaaagtgagagcaggtgcttccccagcggcgcgctccgctagggcccggcaggatcccgcccccaagtcgggaaaagttggtcg
gcgccttttctccccgacgaagccgctccagggctgctctcagaggacgcgcggcaggcaaagagaatgaacctgagcgtccacgaaac
gtcctgcacggctcccgggagctgggagaaacaggtgcctttctccgacgtccgcggggcgacgcctgccgcaccttgcccgctgccgcg
cccctcccgggcacccctcgccctcggcgcccctgcccccacccccagtgccagggcggaggcagtcccggctcgcaggtaattattgc
cagcggagcccgccggggagcggggtgggcgcgccggcggtgggcgGcgggcgcggcggggcgcgggcataaagggcgc
ggcgcggggccccggagcctggctcccgcgcagcatgcccgccagcgccccgccgcgccgcccgcggccgccgccgtcgctgt
cgctgctgctggtgctgctgggcctgggcggccgccgcctgcgtgcggagccgggcgacggcgcgcagacctgggcccgtttctcgcg
gcctcctgccccgaggccgcgggcctcttccagggcaccttccccgacggcttcctctgggccgtgggcagcgccgcctaccagaccg
agggcggctggcagcagcacggcaagggtgcgtccatctgggacacgttcacccaccacccctggcacccccgggagactcccgga
acgccagtctgccgttgggcgccccgtcgccgctgcagcccgccaccggggacgtagccagcgacagctacaacaacgtcttccgcga
cacggaggcgctgcgcgagctcggggtcactcactaccgcttctccatctcgtgggcgcgagtgctccccaatggcagcgcgggcgtcc
ccaaccgcgaggggctgcgctactaccggcgcctgctggagcggctgcgggagctgggcgtgcagcccgtggtcaccctgtaccactg
ggacctgccccagcgcctgcaggacgcctacggcggctgggccaaccgcgccctggccgaccacttcagggattacgcggagctctgc
ttccgccacttcggcggtcaggtcaagtactggatcaccatcgacaacccctacgtggtggcctggcacggctacgccaccgggcgcctg
gcccccggcatccggggcagcccgcggctcgggtacctggtggcgcacaa PAR2 CpG Island (SEQ ID NO:114)

Cccggggcgtggcctcccgcaggtgagtacgctgctccttcggtttccctgaaacctaacccgccctggggaggcgcgcagcagaggct
ccgattcggggcaggtgagaggctgactttctctcggtgcgtccagtggagctctgagtttcgaatcggcggcggcggattccccgcgcgc
ccggcgtcggggcttccaggaggatgcggagccccagcgcggcgtggctgctgggggccgccatcctgc FIGURE 4E
PITX2 CpG Island (SEQ ID NO:115)

agtccgtgctcctgctcctcggttggctcctaagtgccccgccaggtccctctccttcgctctcccggctccggctcccgactcttcggcccgctggcatctgcttccctc
ccctgcctcgtttctcgtcgcccctgctcgctcccccggcgctcgcccggcgctgtgctcgctcctggatcgccagccgcgcagccgggctcggccggccgcccg
cgcgccactgtgcagtggagtttggtggaatctctgctgacgtcacgtcactccccacacggagtaggagcagagggaagagagagggatgagagggagggagag
gagagagagtgcgagaccgagcgagaaagctggagaggagcagaaagaaactgccagtggcggctagatttcggaggccccagtgcacccgtggactccttcgga
acttggcaccctcaggagccctgcagtcctctcaggcccggctttcgggcgcttgccgtgcagccggaggctcggctcgctggaaatcgccccgggaagcagtggga
cgcggagacagcagctctctcccggtagccgataacggggaaatggagaccaactgccgcaaactggtgtcggcgtgtctgcaattagagaaagataaaagccagca
ggggaagaatgaggacgtgggcgccgaggacccgtctaagaagaagcggcaaaggcggcagcgga PTCA CpG Island (SEQ ID NO:116)

GCGGCCGCAGCGGCAGCAGCGCCCGCCGTGTGAGCAGCAGCAGCGGCTGGTCTGTCAACCGGAGCCC
GAGCCCGAGCAGCCTGCGGCCAGCAGCGTCCTCGCAAGCCGAGCGCCCAGGCGCGCCAGGAGCCCGC
AGCAGCGGCAGCAGCGCGCCGGGCCGCCCGGGAAGCCTCCGTCCCCGCGGCGGCGGCGGCGGCGGCG
GCAACATGGCCTCGGCTGGTAACGCCGCCGAGCCCCAGGACCGCGGCGGCGGCGGCAGCGGCTGTAT
CGGTGCCCCGGGACGGCCGGCTGGAGGCGGGAGGCGCAGACGGACGGGGGGGCTGCGCCGTGCTGCC
GCGCCGGACCGGGACTATCTGCACCGGCCCAGCTACTGCGACGCCGCCTTCGNTNNGGAGNAGATTTN
CCANGGNNGGCATTTCAGACTNTNTCNTTCCCACTTTNTCTTCCCNTACCTNTAACTCNTGGGGATCG
CCCCCGCCACACACAAACACACACACTNTCTTCCTCTNTNTCTCACACACAACACACACACTCACTCAC
ACNTCTNCAGGAAAAGCAGCAGACAAATGGGGATTGAAAAATTCAAACCCTCCCTCTGGTNNTGGGA
GGAAAGGGCTGTCTGAGGTCCGCAGGGGGTGGAGGTGTGTGTGTGTGCGTGTGTGTGTGTGNANACAC
ACGCCCTCCCTGGTGTGCCTTTTCCGGAGCACTGGAAAGCCGTCCACGGCGGACCACCTCAAGGGCGG
CCGC

GCGGTCGTAGCGGTAGTAGCGTTCGTCGTGTGAGTAGTAGTAGCGGTTGGTTTGTTAATCGGAGTTCG
AGTTCGAGTAGTTTGCGGTTAGTAGCGTTTTCGTAAGTCGAGCGTTTAGGCGCGTTAGGAGTTCGTAGT
AGCGGTAGTAGCGCGTCGGGTCGTTCGGGAAGTTTTCGTTTTCGCGGCGGCGGCGGCGGCGGCGGTAA
TATGGTTTCGGTTGGTAACGTCGTCGAGTTTTAGGATCGCGGCGGCGGCGGTAGCGGTTGTATCGGTGT
TTCGGGACGGTCGGTTGGAGGCGGGAGGCGTAGACGGACGGGGGGGTTGCGTCGTGTTGTCGCGTCG
GATCGGGATTATTTGTATCGGTTTAGTTATTGCGACGTCGTTTTCGNTNNGGAGNAGATTTNTTANGGN
NGGTATTTTAGATTNTNTNTTNTTTTTATTTTNTTTTTTTNTATTTNTAATTTNTGGGGATCGTTTTCGTTA
TATATAAATATATATATNTTTTTTTTTNTNTTTTATATATAATATATATATTTATTTATATNTTTNTAGG
AAAAGTAGTAGATAAATGGGGATTGAAAAATTTAAATTTTTTTTTTGGTNNTGGGAGGAAAGGGTTGT
TTGAGGTTCGTAGGGGGTGGAGGTGTGTGTGTGTGCGTGTGTGTGTGTGNANATATACGTTTTTTTTGG
TGTGTTTTTTTCGGAGTATTGGAAAGTCGTTTACGGCGGATTATTTTAAGGGCGGTCGT

PTCHB CpG Island (SEQ ID NO:117)

GCGGCCGCGGCACTGTCCTGCCCCGTGCCCCCTGCCCTGAACTTCTTCCTCCTGCGCCCCTGCCCCTAT
TTGCAGCCTAAACTCCTGTACGGCTGCCACATTTCTTAACATCTTGGAGGGGGAGGCGGAGTGGAGAG
AGGCGGAGAGAGGAAGGGGGGAGGGAGCCGAAATAAAGGTGGTTTCCTTTTTTGGCAGCCAGTTTTG
GTTTTGTTGAGCATGAAATCTCTGCTCCCTTAAAAAATTATTCTCGGAAAAAGATATCCCCCCCGTTTT
CCAGGTTTTGAGCCGCCTCTCCTTAGGGCCTGGTCGGGGGAGGAAAAGTTGTAAACAAATTGCCACCT
TAAATTCGCGGTGCGANTCTGCGGAGCTGCCGGGTTCATTGTGTTTACGAGGCTCGCTGAAATGTGTG
GAATCCAGGGAAGGCGAGCACCCAGACGGGGGCCCGCCGGGGCCGCGGCCAGCGCCGGGGAAATGC
CGCGCCGGGGAGCAGCATGCGCCGGCCTGAGCCCTTCCCTTTGCACTCGGCTGTTTTTTACGTTTAACC
AGAAAGGAAGGGAGAGGAGGGAAAGATCCATGTGGCTGCCCTCTTCCGATCACAAATATTGTCGTAA
GTTGCAGCTGGCTGCCCCANTTCCTAATTCAGCTCACACAGCNTNTCCCCACGCTATGGAAATGCGTCG
GGAGTGAACTCCGGCGGCCGC

FIGURE 4F

SDC1 CpG Island (SEQ ID NO:118)

Ggagaggtgcgggccgaatccgagccgagcgagaggaatccggcagtagagagcggactccagccggcggaccctgcagccctcg
cctgggacagcggcgcgctgggcaggcgcccaagagagcatcgagcagcggaacccgcgaagccggcccgcagccgcgacccgc
gcagcctgccgctctcccgccgccggtccgggcagcatgaggcgcgcggcgctctggctctggctgtgcgcgctggcgctgagcctgc
agctggccctgccgca SDC4 CpG Island (SEQ ID NO:119.)

Agtaggagccggcgggctcgggcagggcgggtcccttggggtttccaactccgcgggcgggcgcagtgccccgcaggcctcgcttcc
actggggaattccgggcggggtgcgggcggcggggcggggcgggccggggcggggccggtaggccgcctataagatgggtggcg
cgcccgcccggggccactcgccgcagcctgcgcgccttctccagtccgcggtgccatggccccgcccgtctgttcgcgctgctgctgtt
cttcgtaggcggagtcgccgagtcggtgggtgcttggaggttcccgggctgggggcgaagcggggcgcaggccggtgcctcctttgtt
cgtcggagcgtgggatggggggggggcagatcgggggtacgctaccccaaccggacaccgaggcccgggaaactttgttggaaacttt
gctccggggtcacgggccagcctccgggatggcttcacgcgccgtgcgccccctcgcctgttgctcttccgcctccccgggcctcagccc
cgccgcgggctacgggctcgttagtgactaagccggtgtcaactcttcaactcccacaccctcgtcccttccctggtgaccctggggcagg
cttggagcgctgaatcccctcctcgctctcggggcgcccagagcagacagctttaggatccgagatggccctgggggtcgggggggctgc
gtgtactcggaagggggagggttttagggttgtgcgaggccc

FIGURE 5

```
MINT31 (SEQ ID NO:120)
CCCGGGGCCT CTATCCTGGC GGGAAGGGCA GGCCGACCCG GCAGACTGCG GCCTCTCGGG
AGGGAAGAAG GTGTCAGACG CGCGGAGCAA CCATAAATAG CCCCCCTTTC CCAGAAGACG
GCACGGGGTT CAAGACTCAG GCGCCGCATA CTCAGAATGA GAGCAGAGAC TCCCGCCAGG
AAAAAAGGGC ACTTAGGGGA TCTGCTCATT AACATGAAAT GCAAATGAGC CCGCCCGGCC
TCATTTACAC AACTCTGTGC ATGGATTCGG CGAAAGGGCA ACCAGGGAGA CGACGGCGCA
GCAGCCACTC TGCCACTTCC CCCATCCCCT CCCCCCATC GGCCGGGCG GGAACTGAGA
CGACCCCAAC CCTCTGCGGC GGCGGGAGGT GCGCGGGGGC TGCGTGGGTG GTGCAGCCTT
AGGGAGTGA ACAACGCCCA GGGGTGATGG CCTCAGCAAA GTGAGGGGTG GTGATGGAGG
TCATCCGACC CATCCCGCCG CCTCTCCGCA GTGGCGCAAG CGCCCCAAAA TCTCCGGAGA
NGGAACTGAG TGACCCACTA GGTTCCGCCG TGTCTACCTC TCGCAGATGT TGGGGAAGTG
CTTCCCGGCG TCTAATCCTC GCTGTTCCCC CCTCCACCGG CGCCCAGCAC ACCCGCGGCG
CTCCGCTCCC GGG
```

CACNA1G POLYNUCLEOTIDE, POLYPEPTIDE AND METHODS OF USE THEREFOR

STATEMENT AS TO FEDERALLY SPONSORED RESEARCH

This invention was made with Government support under Grant No. Ca43318 and CA54396, awarded by the National Cancer Institute and Grant No. CA43318, a Colon Cancer Spore Grant. The government may have certain rights in the invention.

FIELD OF THE INVENTION

The present invention relates generally to the regulation of gene expression and more specifically to a method of determining the DNA methylation status of CpG sites in a given locus and correlating the methylation status with the presence of a cell proliferative disorder.

BACKGROUND OF THE INVENTION

DNA methylases transfer methyl groups from the universal methyl donor S-adenosyl methionine to specific sites on the DNA. Several biological functions have been attributed to the methylated bases in DNA. The most established biological function for methylated DNA is the protection of DNA from digestion by cognate restriction enzymes. The restriction modification phenomenon has, so far, been observed only in bacteria. Mammalian cells, however, possess a different methylase that exclusively methy-lates cytosine residues that are 5' neighbors of guanine (CpG). This modification of cytosine residues has important regulatory effects on gene expression, especially when involving CpG rich areas, known as CpG islands, located in the promoter regions of many genes.

Methylation has been shown by several lines of evidence to play a role in gene activity, cell differentiation, tumorigenesis, X-chromosome inactivation, genomic imprinting and other major biological processes (Razin, A., H., and Riggs, R. D. eds. in *DNA Methylation Biochemis-try and Biological Significance,* Springer-Verlag, New York, 1984). In eukaryotic cells, methylation of cytosine residues that are immediately 5' to a guanosine, occurs predominantly in CG poor regions (Bird, A., Nature, 321:209, 1986). In contrast, CpG islands remain unmethylated in normal cells, except during X-chromosome inactivation (Migeon, et al., supra) and parental specific imprinting (Li, et al., Nature 366:362, 1993) where methylation of 5' regulatory regions can lead to transcriptional repression. Do novo methylation of the Rb gene has been demonstrated in a small fraction of retinoblastomas (Sakai, et al., Am. J. Hum. Genet., 48:880, 1991), and recently, a more detailed analysis of the VHL gene showed aberrant methylation in a subset of sporadic renal cell carcinomas (Herman, et al., Proc. Natl. Acad. Sci., U.S.A., 91:9700, 1994). Expression of a tumor suppressor gene can also be abolished by de novo DNA methylation of a normally unmethylated CpG island (Issa, et al., Nature Genet., 7:536, 1994; Herman, et al., supra; Merlo et al., Nature Med., 1:686, 1995; Herman, et al., Cancer Res., 56:772, 1996; Graff, et al., Cancer Res., 55:5195, 1995; Herman, et al., Cancer Res., 55:4525, 1995).

Human cancer cells typically contain somatically altered nucleic acid, characterized by mutation, amplification, or deletion of critical genes. In addition, the nucleic acid from human cancer cells often display somatic changes in DNA methylation (E. R. Fearon, et al., Cell, 61:759, 1990; P. A. Jones, et al., Cancer Res., 46:461, 1986; R. Holliday, Science, 238:163, 1987; A. De Bustros, et al., Proc. Natl. Acad. Sci., USA, 85:5693, 1988); P. A. Jones, et al., Adv. Cancer Res., 54:1, 1990; S. B. Baylin, et al., Cancer Cells, 3:383, 1991; M. Makox, et al., Proc. Natl. Acad. Sci., USA, 89:1929, 1922; N. Ohtani-Fujita, et al., Onco-gene, 8:1063, 1993). However, the precise role of abnormal DNA methylation in human tumorigenesis has not been established. Aberrant methylation of normally unmethylated CpG islands has been described as a frequent event in immortized and transformed cells, and has been associated with transcriptional inactivation of defined tumor suppressor genes in human cancers. In the development of colorectal cancers (CRC), a series of tumor suppressor genes (TSG) such as APC, p53, DCC and DPC4 are inactivated by mutations and chromosomal deletions (reviewed in Kinzler and Vogelstein 1996). Some of these alterations result from a chromosomal instability phenotype described in a subset of CRC (Lengauer et al., 1997a). Recently, an additional pathway has been shown to be involved in a familial form of CRC, hereditary non-polyposis colorectal cancer. The cancers from these patients show a characteristic mutator phenotype which causes microsatellite instability (MI), and mutations at other gene loci such as TGG-beta-RII (Markowitz et al., 1995) and BAX (Rampino et al., 1997). This phenotype usually results from mutations in the mismatch repair (MMR) genes hMSH2 and hMLH1 (reviewed by Peltomaki, and de la Chapelle, 1997). A subset of sporadic CRC also show MI, but mutations in MMR genes appear to be less frequent in these tumors (Liu et al., 1995; Moslein et al., 1996).

Another molecular defect described in CRC is CpG island (CGI) methylation. CGIs are short sequences rich in the CpG dinucleotide and can be found in the 5' region of about half of all human genes. Methylation of cytosine within 5' CGIs is associated with loss of gene expression and has been seen in physiological conditions such as X chromosome inactivation and genomic imprinting (reviewed in Latham, 1996). Aberrant methylation of CGIs has been detected in genetic diseases such as the fragile-X syndrome, in aging cells and in neoplasia. About half of the tumor suppressor genes which have been shown to be mutated in the germline of patients with familial cancer syndromes have also been shown to be aberrantly methylated in some proportion of sporadic cancers, including Rb, VHL, p16, hMLH1, and BRCA1 (reviewed in Baylin, S. B., Herman, J. G., Graff, J. R., Vertino, P. M. and Issa, J. P. Alterations in DNA methylation: a fundamental aspect of neoplasia, Adv. Cancer Res. 72:141–196 1998). TSG methylation in cancer is usually associated with (1) lack of gene transcription and (2) absence of coding region mutation. Thus it has been proposed that CGI methylation serves as an alternative mechanism of gene inactivation in cancer.

The causes and global patterns of CGI methylation in human cancers remain poorly defined. Aging could play a factor in this process because methylation of several CGIs could be detected in an age-related manner in normal colon mucosa as well as in CRC (Issa, J. P., Vertino, P. M., Boehm, C. D., Newsham, I. F. and Baylin, S. B. Methylation of the oestrogen receptor CpG island links ageing and neoplasia in human colon. Nat Genet. 7:536–540, 1994). In addition, aberrant methylation of CGIs has been associated with the MI phenotype in CRC as well as specific carcinogen exposures (Issa et al., 1996) supra. However, an understanding of aberrant methylation in CRC has been somewhat limited by the small number of CGIs analyzed to date. In fact, previous studies have suggested that large numbers of CGIs are methylated in immortalized cell lines (Antequera, F., Boyes, J. and Bird, A. High levels of de novo methylation and altered chromatin structure at CpG islands in cell lines. Cell 62:503–514, 1990), and it is not well understood whether this global aberrant methylation is caused by the cell culture conditions or whether they are an integral part of the pathogenesis of cancer.

Most of the methods developed to date for detection of methylated cytosine depend upon cleavage of the phosphodiester bond alongside cytosine residues, using either methylation-sensitive restriction enzymes or reactive chemicals such as hydrazine which differentiate between cytosine and its 5-methyl derivative. Genomic sequencing protocols which identify a 5-MeC residue in genomic DNA as a site that is not cleaved by any of the Maxam Gilbert sequencing reactions have also be used, but still suffer disadvantages such as the requirement for large amount of genomic DNA and the difficulty in detecting a gap in a sequencing ladder which may contain bands of varying intensity.

Mapping of methylated regions in DNA has relied primarily on Southern hybridization approaches, based on the inability of methylation-sensitive restriction enzymes to cleave sequences which contain one or more methylated CpG sites. This method provides an assessment of the overall methylation status of CpG islands, including some quantitative analysis, but is relatively insensitive and requires large amounts of high molecular weight DNA.

Another method utilizes bisulfate treatment of DNA to convert all unmethylated cytosines to uracil. The altered DNA is amplified and sequenced to show the methylation status of all CpG sites. However, this method is technically difficult, labor intensive and without cloning amplified products, it is less sensitive than Southern analysis, requiring approximately 10% of the alleles to be methylated for detection.

Identification of the earliest genetic changes in tumorigenesis is a major focus in molecular cancer research. Diagnotic approaches based on identification of these changes are likely to allow implementation of early detection strategies and novel therapeutic approaches targeting these early changes might lead to more effective cancer treatment.

SUMMARY OF THE INVENTION

The present invention is based on the finding that several genes are newly identified as being differently methylated in cancer. This seminal discovery is useful for cancer screening, risk-assessment, prognosis, minimal-residual disease identification, staging and identification of therapeutic targets. The identification of new genes that are methylated in cancer, aging or diseases associated with aging increases the likelihood of finding genes methylated in a particular cancer; increases the sensitivity and specificity of methylation detection; allows methylation profiling using multiple genes; and allows identification of new targets for therapeutic intervention. The invention also provides a newly identified gene that is a target for hypermethylation in human tumors. This new gene, as well as genes newly identified as hypermethylated in cancer and aging or aging diseases provides markers which can be used diagnostically, prognostically and therapeutically over the course of such disorders.

In a first embodiment, the invention provides a nucleic acid molecule comprising a coding region for a T-type calcium channel, CACNA1G, and regulatory sequences associated therewith. The discovery of CpG islands, and in particular, methylated CpG islands in the region approximately 300–800 base pairs upstream for the CACNA1G translation initiation start site, led to a method of the present invention for correlating methylated CpG islands with various cancers. In one aspect of this embodiment, the nucleic acid molecule encoding CACNA1G and the associated regulatory sequences and CpG-rich regions include the nucleic acid sequence set forth in SEQ ID NO:51 (FIG. 3A). Also provided is a polypeptide having an amino acid sequence as set forth in SEQ ID NO:52 and FIG. 3B. The methylation state of CpG islands in CACNA1G, associated regulatory regions, and other genes is indicative of the presence of a cellular proliferative disorder in a subject from which the CpG-containing nucleic acid is isolated.

In another embodiment, there are provided methods for detecting a cellular proliferative disorder in a subject. The subject may have or be at risk of having a cellular proliferative disorder. The method of the invention is useful for diagnostic as well as prognostic analyses. One method for detecting a cellular proliferative disorder in a subject includes contacting a nucleic acid-containing specimen from the subject with an agent that provides a determination of the methylation state of at least one gene or associated regulatory region of the gene; and identify aberrant methylation of regions of the gene or regulatory region, wherein aberrant methylation is identified as being different when compared to the same regions of the gene or associated regulator region in a subject not having the cellular proliferative, thereby detecting a cellular proliferative disorder in the subject. The method includes multiplexing by utilizing a combination of primers for more than one loci, thereby providing a methylation "profile" for more than one gene or regulatory region.

For the first time, the invention provides methylated forms of the following genes and/or their associated regulatory sequences: APOB, CACNA1G, CDX2, EGFR, FBN1, GPR37, HSPA6, IQGAP2, KL, PAR2, PITX2, PTCH, SDC1, and SDC4 (see Table 5). In addition, the invention provides the CpG-rich regions from these genes that are hypermethylated (see FIGS. 4A–4F (SEQ ID NO:105–119).

Invention methods include determining, in a nucleic acid-containing specimen taken from a subject, the methylation state of a gene or regulatory sequences associated therewith, wherein the expression or non-expression of the gene is associated with the presence of the cellular proliferative disorder, and identifying as having a cellular proliferative disorder a subject that has aberrant methylation of regions of the gene or associated regulatory sequences when compared to the same regions of the gene in a subject not having the cellular proliferative disorder. In one aspect of this embodiment, the methylated regions of the gene and associated regulatory sequences are contained within CpG islands (i.e., CpG rich regions). In particular, the aberrant methylation typically includes hypermethylation as compared with the same regions of the gene or regulatory sequences in a subject not having the cellular proliferative disorder.

Determining the methylation state of the gene includes contacting the nucleic acid-containing specimen with an agent that modifies unmethylated cytosine, amplifying a CpG-containing nucleic acid in the specimen by means of CpG-specific oligonucleotide primers, wherein the oligonucleotide primers distinguish between modified methylated and nonmethylated nucleic acid, and detecting the methylated acid based on the presence or absence of amplification products produced in said amplifying step. The method includes optionally contacting the amplification products with a methylation sensitive restriction endonuclease. Other methods for determining methylation status of a gene and/or regulatory sequences are well known in the art and are described more fully herein.

In another embodiment, the present invention provides a method of treating a cell proliferative disorder associated with CACNA1G or other methylated genes described herein, comprising administering to a subject with the disorder, a therapeutically effective amount of reagent which modulates CACNA1G or other methylated genes' expression. For example, since CACNA1G -associated disorders typically involve hypermethylation of CACNA1G polynucleotide sequence, a polynucleotide sequence which contains a non-methylatable nucleotide analog is utilized for treatment of a subject. Further, the invention provides a method of gene therapy comprising introducing into cells of a host subject, an expression vector comprising a nucleotide sequence encoding CACNA1G or other methylated genes described herein, in operable linkage with a promoter.

In another embodiment of the present invention there is provided a kit useful for the detection of a cellular proliferative disorder in a subject having at risk for having a cellular proliferative disorder. Invention kits include a carrier means compartmentalized to receive a sample, one or more containers comprising a first container containing a reagent which modifies unmethylated cytosine and a second container containing primers for amplification of a CpG-containing nucleic acid, wherein the primers distinguish between modified methylated and nonmethylated nucleic acid, and optionally, a third container containing a methylation sensitive restriction endonuclease.

BRIEF DESCRIPTION OF THE FIGURES

FIG. 2 depicts the correlation of methylation and the expression of CACNA1G.

FIGS. 3A and 3B show the nucleic acid sequence and deduced amino acid sequence of CACNA1G (SEQ ID NO:51 and 52, respectively).

FIGS. 4A–4F show the CpG-rich regions of the genes depicted in Table 5 (SEQ ID NO:105–119).

FIG. 5 is the nucleotide sequence of MINT31. (SEQ ID NO:120).

DETAILED DESCRIPTION OF THE INVENTION

Figure 1A:
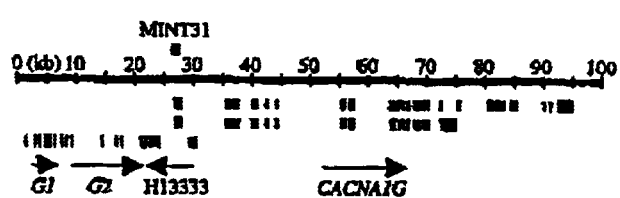
FIG. 1A shows the relative positions of MINT31 and CACNA1G and associated CpG regions.
Figure 1B:
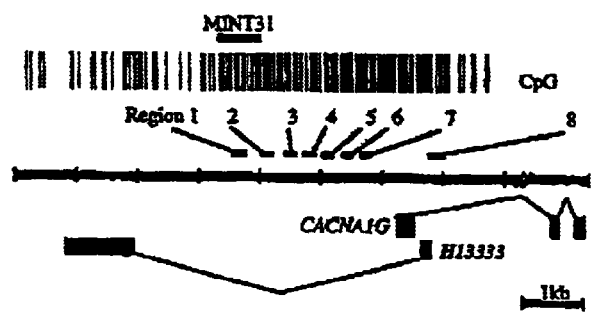
FIG. 1B provides a magnified depiction of MINT31, CACNA1G and CpG rich regions 1–8.

It has been determined that an aberrant methylation state of nucleic acids in certain genes, particularly regulatory sequences, is diagnostic for the presence or potential development of a cellular proliferative disorder in subjects bearing the aberrantly methylated nucleic acid. More particularly, the hypermethylation of certain nucleotides localized in CpG islands has been shown to affect the expression of genes associated with the CpG islands; typically such hypermethylated genes have reduced or abolished expression, primarily due to down-regulated transcription. Using a recently developed PCR-based technique called methylated CpG island amplification (MCA), several nucleic acid molecules aberrantly methylated in a colon cancer cell line were identified. One DNA fragment, termed MINT31, mapped to human chromosome 17q21 where frequent loss of heterozygosity (LOH) has been detected in various human tumors. By characterizing the genomic sequence around this area, a gene encoding a T-type calcium channel, CACNA1G, was identified as a target for hypermethylation in human tumors. Using RT-PCR, expression of CACNA1G was detected in a normal colon and bone marrow, but expression was absent in 5 tumor cells lines where methylation was found. After treatment with the methylation inhibition 5-deoxy-azacytidine, the expression of CACNA1G was restored in all 5 cell lines. Detailed methylation mapping of the 5'CpG island by bisulfite-PCR revealed that methylation of a region 300 to 800 base pairs upsteam of the translation initiation site closely correlated with the inactivation of CACNA1G. Aberrant methylation of CACNA1G was also examined in various human primary tumors, and was detected in 17 of 49 (35%) colorectal cancers, 4 of 16 (25%) gastric cancers, and 3 of 23 (13%) acute myelogenous leukemia cases. While not wanting to be bound by a particular theory, it is believed that inactivation of CACNA1G may play a role in cancer development by modulating calcium signaling, which potentially affects cell proliferation and apoptosis.

Thus, in one embodiment of the present invention, there are provided nucleic acids comprising the coding region for a T-type calcium channel and regulatory sequences associated therewith. Specifically, the T-type calcium channel and associated regulatory sequences comprise CACNA1G. In a more preferred embodiment, the CACNA1G is the human form of the gene. An exemplary CACNA1G gene and associated regulatory sequences is set forth in SEQ ID NO:51.

The invention provides methylated and unmethylated nucleic acid encoding CACNA1G (SEQ ID NO:51). Polynucleotides include DNA, cDNA and RNA sequences which encode CACNA1G polypeptide (SEQ ID NO:52). It is understood that naturally occurring, synthetic, and intentionally manipulated polynucleotides are included. For example, CACNA1G nucleic acid may be subject to site-directed mutagenesis, or the like. The nucleic acid sequences for CACNA1G also include antisense sequences, and sequences encoding dominant negative forms of CACNA1G, as well as sequences encoding functional fragments thereof. It is understood that natural occurring, synthetic, and intentionally manipulated polynucleotides are included.

Methylated nucleic acid sequences are also provided. For the first time, the present invention provides methylated chemical structures for the following genes: APOB, CACNA1G, CDX2, EGFR, FBN1, GPR37, HSPA6, IQGGAP2, KL, PAR2, PITX2, PTCH, SDC1, and SDC4. One of skill in the art can now readily locate the GpG-rich sequences associated with these genes and identify such methylated forms of the genes/regulatory sequences by methods described herein (The gene sequences can be identified in a gene database found at the following uniform resource locator (url): ncbi.nim.mih.gov/UniGene/index.html). The invention provides CpG-rich regions from the above genes as set forth in SEQ ID Nos:105–119. Thus, in yet another embodiment, the invention provides an isolated nucleic acid molecule having at least one methylated Cytosine of a CpG dinucleotide in a CpG-rich region and encoding a gene selected from APOB, CACNA1G, CDX2, EGFR, FBN1, GPR37, HSPA6, IQGAP2, KL, PAR2, PITX2, PTCH, SDC1, and SDC4. The methylated C residue of a CpG dinucleotide is located within a CpG-rich region selected from SEQ ID NO:105–118 and SEQ ID NO:119.

The polynucleotides of the invention include "degenerate variants" which are sequences that encode the same polypeptide yet vary in sequence as a result of the genetic code. There are 20 natural amino acids, most of which are specified by more than one codon. Therefore, all degenerate nucleotide sequences are included in the invention as long as the amino acid sequence of a polypeptide encoded by the nucleotide sequence of SEQ ID NO:51 is functionally unchanged.

The term "polynucleotide" or "nucleic acid sequence" refers to a polymeric form of nucleotides at least 10 bases in length. An "isolated polynucleotide" is a polynucleotide that is not immediately contiguous with both of the coding sequences with which it is immediately contiguous (one on the 5' end and one on the 3' end) in the naturally occurring genome of the organism from which it is derived. Thus, an isolated polynucleotide may include a coding region with its associated regulatory sequences. The term therefore includes, for example, a recombinant DNA which is incorporated into a vector; into an autonomously replicating plasmid or virus; or into the genome DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. Specifically, methylated forms of nucleotides in a polynucleotide sequence, such as regions 1–8 of CACNA1G as described herein, are also included. The term includes single and double forms of DNA.

As will be understood by those of skill in the art, when the sequence is RNA, the deoxynucleotides A, G, C, and T of SEQ ID NO:51, are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes SEQ ID NO:52. The term "selectively hybridize" refers to hybridization under moderately or highly stringent conditions (See, Maniatis, as cited herein) which excludes non-related nucleotide sequences.

The CACNA1G nucleic acid sequence includes the disclosed sequence and sequences that encode conservative variations of the polypeptides encoded by CACNA1G polynucleotide provided herein. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypetide.

CACNA1G nucleic acid sequences can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cells" is used. Methods of stable transfer, meaning that the foreign DNA is continuous-ly maintained in the host, are known in the art.

In one aspect, the CACNA1G nucleic acid sequences may be inserted into an expression vector. The term "expression vector" refers to a plasmid, virus or other vehicle known in the art that has been manipulated by insertion or incorporation of the sequence of interest genetic sequences. Polynucleotide sequence which encode sequence of interest can be operatively linked to expression control sequences. "Operatively linked" refers to a juxtapostion wherein the components so described are in a relationship permitting them to function in their intended manner. An expression control sequence operatively linked to a coding sequence is ligated such that expression of the coding sequence is achieved under conditions compatible with the regulatory or expression control sequences. As used herein, the terms "regulatory sequences" and "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop condons. The terms "regulatory sequences" and "expression control sequences" are intended to included, at a minimum, components whose presence can influence expression, and can also include additional components whose presence is advantageous, for example, leader sequences and fusion partner sequences. An example of an expression control sequence includes a promoter.

A "promoter" is a minimal sequence sufficient to direct transcription. Also included in the invention are those promoter elements which are sufficient to render promoter-dependent gene expression controllable for cell-type specific, tissue-specific, or inducible by external signal or agents; such elements may be located in the 5' or 3' regions of the gene. Both constitutive and inducible promoters, are included in the invention (see, e.g., Bitter et al., Methods in Enzymology 153:516–544, 1987). For example, when cloning in bacterial systems, inducible promoters such as pL of bacteriophage plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the CACNA1G polynucleotide sequence may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., Gene 56:125, 1987), the pMSXND expression vector for expression in mammalian cells (Lee and Nathans, J. Biol. Chem. 263:3521, 1988) and baculovirus-derived vectors for expression in insect cells. The DNA segment can be present in the vector operably linked to regulatory elements, for example, a promoter (e.g., T7, metallothionein I, or polyhedron promoters.

CACNA1G polynucleotide sequences can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorp-orate DNA sequences of the invention.

"Transformation" means a genetic change induced in a cell following incorporation of new DNA (i.e., DNA exogeneous to the cell). Where the cell is a mammalian cell, the genetic change is generally achieved by introduction of the DNA into the genome of the cell (i.e., stable).

Thus, a "transformed cell" is a cell into which (or into an ancestor or which) has been introduced, by means of recombinant DNA techniques, a DNA molecule encoding sequence of interest. Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the CaCl2 method using procedures well known in the art. Alternatively, MgCl2 or RbCl can be used. Transforma-tion can also be performed after forming a protoplast of the host cell if desired.

When the host is a eukaryote, such methods of transfection of DNA as calcium phosphate co-precipitates, conventional mechan-ical procedures such as microinjection, electroporation, insertion of a plasmid encased in liposomes, or virus vectors may be used. Eukaryotic cells can also be cotransformed with DNA sequenc-es encoding the sequence of interest, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukary otic cells and express the protein (see for example, *Eukaryotic Viral Vectors,* Cold Spring Harbor Laboratory, Gluzman ed., 1982).

Methods which are well known to those skilled in the art can be used to construct expression vectors containing the CACNA1G coding sequence and appropriate transcriptional/translational control signals. These methods include in vitro recombinant DNA techniques, synthetic techniques, and in vivo recombination/genetic techniques. See, for example, the techniques described in Maniatis, et al., 1989 Molecular Cloning A Laboratory Manual, Cold Spring Harbor Laboratory, N.Y.

A variety of host-expression vector systems may be utilized to express the CACNA1G coding sequence. These include but are not limited to microorganisms such as bacteria transformed with recombinant bacteriophage DNA, plasmid DNA or cosmid DNA expression vectors containing the CACNA1G coding sequence; yeast transformed with recombinant yeast expression vectors containing the CACNA1G coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the CACNA1G coding sequence; insect cell systems infected with recombinant virus expression vectors (e.g., baculovirus) containing the CACNA1G coding sequence; or animal cell systems infected with recombinant virus expression vectors (e.g., retroviruses, adenovirus, vaccinia virus) containing the CACNA1G coding sequence, or transformed animal cell systems engineered for stable expression. Since CACNA1G has not been confirmed to contain carbohydrates, both bacterial expression systems as well as those that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter, et al., Methods in Enzymology 153:516–544, 1987). For example, when cloning in bacterial systems, inducible promoters such as pL of bacteriophage gamma., plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted CACNA1G coding sequence. In addition, the endogenous CACNA1G promoter may also be used to provide transcription machinery of CACNA1G.

In bacterial systems a number of expression vectors may be advantageously selected depending upon the use intended for the expressed. For example, when large quantities of CACNA1G are to be produced, vectors which direct the expression of high levels of fusion protein products that are readily purified may be desirable. Those which are engineered to contain a cleavage site to aid in recovering are preferred. Such vectors include but are not limited to the *E. coli* expression vector pUR278 (Ruther, et al., EMBO J. 2:1791, 1983), in which the CACNA1G encoding sequence may be ligated into the vector in frame with the lac Z coding region so that a hybrid -lac Z protein is produced; pIN vectors (Inouye & Inouye, Nucleic Acids Res., 13:3101–3109, 1985; Van Heeke & Schuster, J. Biol. Chem. 264:5503–5509, 1989); glutathione-S-transferase (GST) and the like.

In yeast, a number of vectors containing constitutive or inducible promoters may be used. For a review see, Current Protocols in Molecular Biology, Vol. 2, 1988, Ed. Ausubel, et al., Green Publish. Assoc. & Wiley Interscience, Ch. 13; Grant, et al., 1987, Expression and Secretion Vectors for Yeast, in Methods in Enzymology, Eds. Wu & Grossman, 31987, Acad. Press. N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern, et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol.11, A Practical Approach, Ed. DM Glover, 1986, IRL Press, Wash., D.C.). Alternatively, vectors may be used which promote integration of foreign DNA sequences into the yeast chromosome.

In cases where plant expression of the CACNA1G coding sequence may be driven by any of a number of promoters. For example, viral promoters such as the 35S RNA and 19S RNA promoters of CaMV (Brisson, et al., Nature 310:511–514, 1984), or the coat protein promoter to TMV (Takamatsu, et al., EMBO J:6:307–311, 1987) may be used; alternatively, plant promoters such as the small subunit of RUBISCO (Coruzzi, et al., EMBO J.3:1671–1680, 1984;

Broglie, et al., Science 224:838–843, 1984); or heat shock promoters, e.g., soybean hsp17.5-E or hsp17.3-B (Gurley, et al., Mol. Cell. Biol. 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9.

An alternative expression system which could be used to express is an insect system. In one such systems, Autographa california nuclear polyhdedrosis virus (AcNPV) is used as a vector to express foreign genes. The virus grows in Spodoptera frugiperda cells. The CACNA1G coding sequence may be cloned into non-essential regions (for example the polyhedron gene) of the virus and placed under control of an AcNPV promoter (for example the polyhedron promoter). Successful insertion of the CACNA1G coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (e.g., see Smith, et al., 1983, J. Viol. 46:584; Smith, U.S. Pat. No. 4,215,051).

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of CACNA1G. Mammalian cell lines may be preferable. Such host cell lines may include but are not limited to CHO, VERO, BHK, HeLa, COS, MDCK, -293, and W138.

Mammalian cell systems which utilize recombinant viruses or viral elements to direct expression may be engineered. For example, when using adenovirus expression vectors, the CACNA1G coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the protein in infected hosts (e.g., see Logan & Shenk, Proc. Natl. Acad. Sci. USA, 81:3655–3659, 1984). Alternatively, the vaccinia virus75K promoter may be used (e.g., see, Mackett, et al., 1982, Proc. Natl. Acad. Sci. USA 79:7415–7419; Mackett, et al., J. Virol. 49:857–864, 1984; Panicali, et al., Proc. Natl. Acad. Sci. USA 79:4927–4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the CACNA1G gene in host cells. (Cone & Mulligan, Proc. Natl. Acad. Sci. USA 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral orgins of replication, host cells can be transformed with the CACNA1G cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltansferase (Lowy, et al., Cell, 22:817, 1980) genese can be employed in tk.sup.-, hgprt.sup.- or aprt.sup.- cells respectively. Also antimetabolite resistance can be used as the basis of selection for dhfr, which confers resistance to methotrextate (Wigler, et al., Natl. Acad. Sci. USA, 77:3567, 1980; O'Hara, et al., Proc. Natl. Acad. Sci. USA, 78: 1527, 1981); gpt, which confers resistance to mycophenolic acid (Mulligan & Berg, Proc. Natl. Acad. Sci. USA, 78: 2072, 1981; neo which confers resistance to the aminoglycoside G-418 (Colberre-Garapin, et al., J. Mol. Biol., 150:1, 1981); and hygro, which confers resistance to hygromycin (Santerre, et al., Gene, 30:147, 1984) genes. Recently, additional selectable genes have been described, namely trpB, which allows cells to utilize indole in place of tryptophan; hisD, which allows cells to utilize histinol in place of histindine (Hartman & Mulligan, Proc. Natl. Acad. Sci. USA, 85:8047, 1988); and ODC (ornithine decarboxylase) which confers resistance to the omithine decarboxylase inhibitor, 2-(difluoromethyl)-DL-ornithine, DFMO (McConlogue L., 1987, In: Current Communications in Molecular Biology, Cold Spring Harbor Laboratory, ed.).

Isolation and purification of microbial polypeptide, or fragments thereof, provided by the invention, may be carried out by conventional means including preparative chromatography and immunological separations involving monoclonal or polyclonal antibodies.

In one embodiment, the invention provides substantially purified polypeptide encoded by CACNA1G polynucleotide sequences. Exemplary CACNA1G polypeptide is set forth in SEQ ID NO:52. The term "substantially purified" as used herein refers to a polypeptide which is substantially free of other proteins, lipids, carbohydrates or other materials with which it is naturally associated. One skilled in the art can purify a polypeptide encoded by CACNA1G polynucleotide sequence using standard techniques for protein purification. The substantially pure polypeptide will yield a single major band on a non-reducing polyacrylamide gel. The purity of the CACNA1G polypeptide can also be determined by amino-terminal amino acid sequence analysis.

Minor modifications of the CACNA1G primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity still ex-ists.

The polypeptides of the invention also include dominant negative forms of the CACNA1G polypeptide which do not have the biological activity of CACNA1G polypeptide sequence. A "dominant negative form" of CACNA1G is a polypeptide that is structurally similar to CACNA1G polypeptide but does not have wild-type CACNA1G function. For example, a dominant-negative CACNA1G polypeptide may interfere with wild-type CACNA1G function by binding to, or otherwise sequestering, regulating agents, such as upstream or downstream components, that normally interact functionally with the CACNA1G polypeptide.

Identification and Isolation of CACNA1G

To identify genes differentially methylated in colorectal cancer, methylated CpG island amplification was used followed by representational difference analysis (Razin and Cedar, Cell 17: 473–476, 1994, herein incorporated by reference). One of the clones recovered (MINT31, see U.S. application Ser. No. 09/309,175, incorporated by reference herein in its entirety) mapped to human chromosome 17q21 using a radiation hybrid panel. A Blast search revealed this fragment to be completely indentical to part of a BAC clone (Genbank: AC004590) sequenced by high throughput genomic sequencing. The region surrounding MINT31 fulfills the criteria of a CpG island: GC content 0.67, CpG/GpC ration 0.78 and a total of 305 CpG sites in a 4 kb region. Using this CpG island and 10 kb of flanking sequences in a Blast analysis, several regions highly homologous to the rat T-type calcium channel gene, CACNA1G, were identified (Perez-Reyes et al., Nature 391: 896–900. 1998, herein incorporated by reference). Several ESTs were also identified in this region. Using Genscan, 2 putative coding sequences (G1, and G2) were identified. Blastp analysis revealed that G1 has a high homology to the EH-domainbinding protein, epsin, while G2 is homologous to a C. elegans hypothetical protein (accession No. 2496828).

The MINT31 CpG island corresponds to the 3' region of G1 and G2, based on the direction of the opening reading frame and the presence of a poly A tail, and, without being bound by theory, is unlikely to influence their transportation. The EST closest to MINT31 (H13333) (SEQ ID NO:120; FIG. 5) was sequenced entirely and was found not to contain a continuous open reading frame, but a poly-adenylation signal was identified on one end, along with a poly A tail. These data suggest that H13333 corresponds to the last 2 exons of an unidentified gene. MINT31 is the intron of this gene and is, again without being bound by theory, unlikely to influence transcription of the unidentified gene. However, based on both promoter prediction (TSSG) analysis of this region and homology to the rat CACNA1G sequence, the MINT31 CpG island is also in the 5' region of human CACNA1G gene and is likely to play a role in its transcriptional activity.

The human CACNA1G sequence deposited in Genbank lacks the 5' region of the gene, when compared to the rat homologue. To determine the 5' region of human CACNA1G, cDNA was amplified by RT-PCR using primers based on the BAC sequence (Genbank: AC004590, herein incorporated by reference). The PCR product were cloned and sequenced, and the genomic organization of the gene was determined by comparing the newly identified sequences as well as the known sequences to the BAC that covers this region. CACNA1G is composed of 34 exons which span a 70 kb area. (See, FIG. 3A and SEQ ID NO:52). Based on sequences deposited in Genbank, the gene has two possible 3' ends caused by alternate splicing. Human CACNA1G is highly homologous to rat CACNA1G with 93% identity at the protein level, and 89% identity at the nucleotide level. The 5' flanking region of human CACNA1G lacks TATA and CAAT boxes, which is similar to many housekeeping genes. A putative TFIID binding site was identified 547–556 bp upstream from the translation start site, and several other potential transcription factor binding sites such as AP1 (1 site), AP2 (2 sites) and SP1 (10 sites), were identified upstream of CACNA1G exon 1 using the promoter prediction program, TESS.

Methylation Analysis of CACNA1G

The CACNA1G CpG island is 4 kb, and is large than many typical CpG islands. MINT31 corresponds to the 5' edge of the island while CACNA1G is in the 3' region. It is not known whether large CpG islands such as this are coordinately regulated with regards to protection from methylation, and aberrant methylation in cancer.

To address this issue, the methylation status of the 5' region of CACNA1G was studied using bisulfate-PCR of DNA from normal tissues as well as 35 human cancer cell lines from colon, lung, prostate, breast and hematopoietic tumors. More specifically, forty-nine primary colorectal cancers, 28 colorectal adenomas, 16 primary gastric cancers and 17 acute myelogenous leukemia samples were used for methylation analyses. DNA from eight colon cancer cell lines (Caco2, RKO, SW48, HCT116, DLD1, Lovo, SW837, HT29), 4 lung cancer cell lines (OH3, H249, H157, H209), 4 glioblastoma cell fines (Duay, D283, U87, U373), 8 breast cancer cell lines (MB-468, MCF7, MB-231, MB-484 MB-435, MB-453, BT20, CAMA1, SKBR3), 7 hematopoietic tumor cell lines (CEM, Raji, KG1A, HL60, ML-1, Molt3, K562), and 4 prostate cancer cell lines (DU145, DUPRO, LNCAP, TSUPRL) were also investigated. The CpG island was divided into 8 regions (SEQ ID NOs: 35–42, respectively). The methylation status of each region was examined separately. The genomic DNA was treated with sodium bisulfate and PCR amplified using primers containing no or a minimum number of CpG sites. (For a detailed description of bisulfate-PCR, see, U.S. Pat. No. 5,786,146, incorporated herein by reference in its entirety). Methylated alleles were detected by digesting the PCR products using restriction enzymes which specifically cleave sites created or retained due to the presence of methylated CpGs. None of the regions was methylated in normal colon, consistent with a uniform protection against de-novo methylation.

Regions 1 and 2 were frequently methylated in cancer cell lines, and behaved in a concordant manner with respect to methylation pattern. Indeed, these 2 regions were methylated in most cancer cell types except gliomas. Moreover, most cell lines where methylation was found methylated both regions 1 and 2. in contrast, region 3, which is less CG rich than any of the other regions, had either no methylation or very low levels of methylation in most cell lines. Regions 5, 6, and 7 behaved quite differently compared to 1–3. Methylation of these regions was less frequent than regions 1–2, as 22/35 cell lines had no detectable methylation there, despite often showing methylation of region 1–2. However, when methylation of regions 5, 6, or 7 was present (in 13/35 cell lines), it affected all 3 regions in a coordinate manner, although to vary extents. Finally, regions 4 and 8 behaved differently again, being partially methylated primarily in colon and breast cell lines. Therefore, with regards to hypermethylation in cancer cells, the CpG rich region upstream of CACNA1G appears to be composed of 2 CpG islands which behave independently. MINT31 corresponds to the upstream CpG island (island 1, regions 1 and 2), while the 5' region of CACNA1G is contained in the downstream CpG island (island 2, regions 5–7). Regions 3,4 and 8 correspond to the edge of these CpG islands, and behave a little differently than the hearts of the CpG islands, as previously described for the E-Cad gene (Graff, et al., J. Biol. Chem. 272: 22322–22329, 1997).

Overall, the methylation patterns of CACNA1G fell into 5 distinct categories: (1) No methylation in any region (normal tissue). (2) Slight methylation of island 1 (6 cell lines, e.g., TSU-PRL). (3) Heavy methylation of island1 but no methylation of island 2 (16 cell lines, e.g., Caco2). (4) Heavy methylation of island 1 and moderate to heavy methylation of island 2 (6 cell lines, e.g., RKO and Raji). (5) High methylation of island 1 and low to moderate methylation of island 2 (7 cell lines, e.g., MB-231).

Methylation Dependent Expression of CACNA1G

In a previous study, rat CACNA1G was shown to be expressed most abundantly in the brain (Perez-Reyes et al., Nature 391: 896–900, 1998). To determine the expression of CACNA1G in normal and neoplastic human cells, RT-PCR was performed using cDNA from various normal tissues and from a panel of 27 tumor cell lines. CACNA1G was expressed ubiquitously in a variety of tissues and cell lines. In normal tissues expression was relatively low but easily detectable, while most cell lines had relatively high expression of CACNA1G. However, some cell lines had negligible or totally absent levels of CACNA1G expression. The results of CACNA1G expression was correlated with the detailed methylation analysis previously described. In this analysis, a remarkable pattern emerged. Methylation of regions 1–4 and 8 had no effect on CACNA1G expression. However, there was a strong correlation between methylation of regions 5–7 and expression of the gene. In fact, all cell lines tested that lack methylation of this region strongly express the gene. All 6 cell lines with pattern 4 methylation studied had no detectable expression. Finally, the 7 cell lines with pattern 5 methylation (examples DLD-1 and MB-453) had variable levels of expression ranging from very low to near normal. The fact that patterns 3 and 5 differ significantly with regards to expression, but are almost identical with regards to methylation of all regions except 7 indicates that this area is important in the inactivation of CACNA1G.

To confirm that methylation of the 5' CpG island of CACNA1G is associated with gene inactivation, 3 non-expressing cell lines showing pattern 4 methylation (RKO, SW48 and Raji) and 2 weakly expressing cell lines showing pattern 5 methylation (MB-231 and MB-435) were treated with 1 M of the methyl-transferase inhibitor 5-deoxyazacitidine. After treatment, all of these cell lines re-expressed CACNA1G mRNA. Consistent with re-expression, demethylation of region 7 was observed after 5-deoxyazacitidine treatment.

De novo cytosine methylation is thought to sometimes occur in vitro during cell propagation (Antequera et al., Cell 62: 503–514, 1990). To determine whether the methylation of CACNA1G occurs in vivo, primary human tumors were examined for methylation of the 5' region of CACNA1G. Aberrant methylation was detected in 17 out of 49 (35%) colorectal cancers, 4 out of 28 colorectal adenomas (25%), 4 out of 16 (25%) gastric cancers and 3 out of 17 (18%) acute myelogeneous leukemia cases. In colorectal cancers, there was a significant correlation between methylation of CACNA1G and methylation of p16 ($p<0.005$) and hMLH1 ($p<0.001$), as well as a strong correlation with the presence of microsatellite instability, and the recently identified CpG island methylator phenotype (CIMP), indicating that CACNA1G is also a target for CIMP in colorectal cancer.

To determine whether aberrant methylation of the 5' region of CACNA1G affects the expression status of this gene in primary tumors RT-PCR was performed using cDNA from a series of colorectal adenomas. Six out of 8 cases which showed no methylation of region 7 expressed CACNA1G. In sharp contrast, all 5 cases that showed methylation of region 7 had no detectable expression of the gene.

Thus, a human T-type calcium channel gene (CACNA1G) has been identified and cloned using the MINT31 sequence as a probe. The human T-type calcium channel gene has been determined to be a target of aberrant methylation and silencing in human tumors. The data show that MINT31 (for a representative sequence of MINIT1–33, see, U.S. patent application Ser. No. 09/309,175) hereby incorporated by reference can be used as a probe to identify genes that play a role in disorders such as cell proliferative disorders.

Detailed analysis of the CpG island upstream of CACNA1G revealed that methylation 300 to 800 bp upstream of the gene closely correlated with transcriptional inactivation. The CACNA1 G promoter is contained in a large CG rich area that is not coordinately methylated in cancer. The CpG island around MINT31 is much more frequently methylated in cancers compared to that just upstream of CACNA1G. This may simply be caused by differential susceptibility to de-novo methylation between these two regions, with methylation of MINT31 serving as a trigger, and eventually spreading to CACNA1G, as described in other genes (Graff, et al., J. Biol. Chem. 272: 22322–22329, 1997). However, it is likely that these 2 regions are controlled by different mechanisms because (1) cell lines kept in culture for countless generations do not in fact spread methylation from MINT31 to CACNA1G (e.g., Caco2), (2) region 3 that separates the 2 islands is infrequently and sparsely methylated in cancer and (3) 2 cases of primary colorectal cancer were found which are methylated at the CACNA1G promoter but not at MINT31). Therefore, methylation of MINT31 appears to be independent of methylation of CACNA1G suggesting that they are 2 distinct CpG islands regulated by different mechanisms.

Many CpG islands of silenced genes appear to be methylated uniformly and heavily throughout the island (e.g., Graff, et al., J, Biol. Chem. 272: 22322–22329, 1997). In contrast the methylation patterns of the 5' region of CACNA1G (region 5–7) was heterogeneous in the cell lines which did not express this gene. Nevertheless, methylation clearly plays a role in CACNA1G repression since demethylation readily reactivates the gene.

The mechanism of CACNA1G methylation remains to be determined. Methylation was not detected in normal colon mucosa, placenta, normal breast epithelium and normal bone marrow, including samples from aged patients, suggesting that methylation of this region is specific for cell proliferative disorders such as cancer, and the like. However, there was a significant correlation between methylation of CACNA1G and other tumor suppressor genes such as p16 and hMLH1. Thus, CACNA1G is likely a target for the recently described CIMP phenotype, which results in a form of epigenetic instability with simultaneous inactivation of multiple genes.

T-type calcium channels are involved not only in electrophysiological rhythm generation but also in the control of cytosolic calcium during cell proliferation and cell death (reviewed in Berridge, et al., Nature 395: 645–648, 1998). Expression of CACNA1G is not limited to brain and heart, indicating a likely role in other tissues in which it is expressed. It has previously been shown that Ca2+ influx via T-type channels is an important factor during the initial stages of cell death such as apoptosis (Berridge, et al., Nature 395: 645–648, 1998), ischemia (Fern, J. Neurosci. 18: 7232–7243, 1998) and complement-induced cytotoxicity (Newsholme, et al., Biochem. J. 295: 773–779, 1993.). The studies culminating in the present invention indicates that impairment of voltage gated calcium channels plays an important role in cancer development and progression through altering calcium signaling.

Due to the clear correlation between methylation of CpG islands and cellular proliferative disorders, in another embodiment of the present invention, there are provided methods for detecting a cellular proliferative disorder in a subject having or at risk for said cellular proliferative disorder. The method includes assaying, in nucleic acid-containing specimen taken from said subject, the methylation state of a gene or its associated regulatory regions, wherein the expression state of the gene or its associated regulatory regions is associated with the presence of the cellular proliferative disorder, and identifying as having a cellular proliferative disorder a subject that has aberrant methylation of regions of said gene. The method provides for detecting a cellular proliferative disorder in a subject having or at risk for said cellular proliferative disorder by identifying aberrantly methylation of regions of a gene when compared to the same regions of the gene in a subject not having said cellular proliferative disorder.

The aberrant methylation comprises hypermethylated CpG rich regions (i.e., islands). In one aspect of the present invention, the CpG rich regions are associated with the CACNA1G gene, and affect the expression thereof in a methylation state-dependent manner. A "cell proliferative disorder" or "cellular proliferative disorder" is any disorder in which the proliferative capabilities of the affected cells is different from the normal proliferative capabilities of unaffected cells. An example of a cell proliferative disorder is neoplasia. Malignant cells (i.e., cancer) develop as a result of a multistep process. Specific, non-limiting examples of cell proliferative disorders associated with increased methylation of CpG-islands are low grade astrocytoma, anaplastic astrocytoma, glioblastoma, medulloblastoma, gastric cancer, colorectal cancer, colorectal adenoma, acute myelogenous leukemia, lung cancer, renal cancer, leukemia, breast cancer, prostate cancer, endometrial cancer and neuroblastoma.

A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. For example, the neoplasm may be a head, neck, lung, esophageal, stomach, prostate, small bowel, colon, bladder, kidney, or cervical neoplasm. The term "benign" refers to a tumor that is noncancerous, e.g. its cells do not proliferate or invade surrounding tissues. The term "malignant" refers to a tumor that is metastastic or no longer under normal cellular growth control.

A cell proliferative disorder may be an age-associated disorder. Examples of age-associated disorders which are cell proliferative disorders include colon cancer, lung cancer, breast cancer, leukimia and melanoma, amongst others.

A "nucleic acid containing specimen" includes any type of material containing a nucleic acid to be subject to invention methods. The nucleic acid may be contained in a biological sample. Such samples include but are not limited to any bodily fluid, such as a serum, urine, saliva, blood, cerebrospinal fluid, pleural fluid, ascites fluid, sputum, stool, or a borpsy sample.

samples or specimens include any CpG-rich DNA sequence, whatever the origin, as long as the sequence is detectably present in a sample. While routine diagnostic tests may not be able to identify cancer cells in these samples, the method of the present invention identifies neoplastic cells derived from the primary tumor or from a metastases. The method includes non-invasive sampling (e.g., bodily fluid) as well as invasive sampling (e.g., biopsy). The sample of DNA of the subject may be serum, plasma, lymphocytes, urine, sputum, bile, stool, cervical tissue, saliva, tears, cerebral spinal fluid, regional lymph node, histopathologic margins, and any bodily fluid that drains a body cavity or organ. Therefore, the method provides for the non-invasive detection of various tumor types including head and neck cancer, lung cancer, esophageal cancer, stomach cancer, small bowel cancer, colon cancer, bladder cancer, kidney cancers, cervical cancer and any other organ type that has a draining fluid accessible to analysis. For example, neoplasia of regional lymph nodes associated with a primary mammary tumor can be detected using the method of the invention. Regional lymph nodes for head and neck carcinomas include cervical lymph nodes, prelaryngeal lymph nodes, pulmonary juxtaesophageal lymph nodes and submandibular lymph nodes. Regional lymph nodes for mammary tissue carcinomas include the axillary and intercostal nodes. Samples also include urine DNA for bladder cancer or plasma or saliva DNA for head and neck cancer patients.

Any nucleic acid sample, in purified or nonpurified form, can be utilized as the starting nucleic acid or acids in accordance with the present invention, provided it contains, or is suspected of containing, a nucleic acid sequence containing a target locus (e.g., CpG-containing nucleic acid). In general, the CpG-containing nucleic acid is DNA. However, invention methods may employ, for example, samples that contain DNA, or DNA and RNA, including messenger RNA, wherein DNA or RNA may be single stranded or double stranded, or a DNA-RNA hybrid may be included in the sample. A mixture of nucleic acids may also be employed. The specific nucleic acid sequence to be detected may be a fraction of a larger molecule or an be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. The nucleic acid-containing sample used for detection of methylated CpG may be from any source including, but not limited to, brain, colon, urogenital, lung, renal, pancreas, liver, esophagus, stomach, hematopoietic, breast, thymus, testis, ovarian, prostate and uterine tissue, and may be extracted by a variety of techniques such as that described by Maniatis, et al. (*Molecular Cloning: a Laboratory Manual*, Cold Spring Harbor, N.Y., pp 290, 281, 1982).

The nucleic acid of interest can be any nucleic acid where it is desirable to detect the presence of a differentially methylated CpG island. The CpG island comprises a CpG island located in a gene or regulatory region for a gene. A "CpG island" is a CpG rich region of a nucleic acid sequence. The nucleic acid sequence may include, for example, APOB, CACNA1G, CDX2, EGFR, FBN1, GPR37, HSPA6, IQGAP2, KL, PAR2, PITX2, PTCH, SDC1, or SDC4 (see for example FIGS. 4A–4F). Alternatively the nucleic acid of interest can be, for example, a MINT31 nucleic acid sequence (SEQ ID NO:120. However, any gene or nucleic acid sequence of interest containing a CpG sequence can provide diagnostic information (i.e., via its methylation state) using invention methods.

Moreover, these markers can also be multiplexed in a single amplification reaction to generate a low cost, reliable cancer screening test for many cancers simultaneously. A combination of DNA markers for CpG-rich regions of nucleic acid may be amplified in a single amplification reaction. The markers are multiplexed in a single amplification reaction, for example, by combining primers for more than one locus. For example, DNA from a urine sample can be amplified with three different randomly labeled primer sets, such as those used for the amplification of the CACNA1 G, EGFR and PTCH loci, in the same amplification reaction. The reaction products are separated on a denaturing polyacrylamide gel, for example, and then exposed to film for visualization and analysis. By analyzing a panel of markers, there is a greater probability of producing a more useful methylation profile for a subject acid from a sample are well known in the art (e.g.,Sambrook et al., *Molecular Cloning: a Laboratory Manual*, Cold Spring Harbor Press, 1989, herein incorporated by reference).

In order to data a differential methylation state for a gene or CpG3-containing region of interest, invention methods include any means known in the art for detecting such differential methylation. For example, detecting the differential methylation may include contacting the nucleic acid-containing specimen with an agent that modifies unmethylated cytosine, amplifying a CpG-containing nucleic acid in the specimen by means of CpG-specific oligonucleotide primers, wherein the oligonucleotide primers distinguish between modified methylated and nonmethylated nucleic acid, and detecting the methylated nucleic acid based on the presence or absence of amplification products produced in said amplifying step. This embodiment includes the PCR-based methods described in U.S. Pat. No. 5,786,146, incorporated herein in its entirety.

For the first time, the methylation state of a number of genes has been correlated with cell proliferative disorders. Examples of such genes, primers useful for identifying their methylation state, and general PCR conditions ate set out in Table 1.

TABLE 1

Bisulfite-PCR Primers

| Genes | 5'-primer | 3'-primer | Annealing Temperature (° C.) |
|---|---|---|---|
| APOB | 5'-gttttttgtagtttgggtttttt-3' TaqI | 5'-RccaacaacRccaacaac-3' | 57 |
| CACNA1G | See Table 2 | | |
| R6 | 5'-ttgtggygttggygatagtt-3' HinfI | 5'-acraaaaaaaaaaaaaaaatctctt-3' | 47TD |
| R7 | 5'-gggggygttttttttyggatttt-3' EcoRI | 5'-ttcccctacrcccctaaaacttcc-3' | 49TD |
| CDX2 | 5'-gtaggttagagggagggatygtt-3' TaqI | 5'-aaaacaaacctcaccatactacct-3' | 60 |
| EGFR | 5'-tttgatttYgtttagtattgat-3' HinfI, TaqI | 5'-cccttaccttttcttttcct-3' | 52 |
| FBN1 | 5'-tttttttattgYgttaattttg-3' TaqI | 5'-tttccccacctcttcaaata-3' | 54 |
| GPR37 | 5'-ggttaggtggggtaagagttt-3' HinfI | 5'-aacRtttaatccaattacaaacc-3' | 56 |
| HSPA6 | 5'-tttttttagtagttttgagttagagg-3' Taq1 | 5'-tttcatccttttacacctccc-3' | 60 |
| IQGAP2 | 5'-tttattttttatttttagtgttag-3' TaqI | 5'-ctcttcRtataacatcctac-3' | 52 |
| KL | 5'-gtagtatgttygttagygttt-3' TaqI | 5'-aaataccctaaaaaaaaccc-3' | 60 |
| PAR2 | 5'-YggttttttGaaatttaattc-3' HinfI, TaqI | 5'-aactccRcatcctcctaaa-3' | 45 |
| PITX2 | 5'-taagtgtttygttaggtttttt-3' Taq1 | 5'-ccaaactccactacacaataac-3' | 60 |
| PTCHA | 5'-gttggtttgttaatyggagt-3' Taq1 | 5'-ttaccaaccraaaccatatt-3' | 60 |
| PTCHB | 5'-aatgtgtggaatttaggga-3' Taq1 | 5'-taaaacaaccaactacaacttac-3' | 60 |
| SDC1 | 5'-agaggaattyggtagtagagag-3' Taq1 | 5'-cacaaccaaaaccaaaac-3' | 60 |
| SDC4 | 5'-ggggatttgtttggtagtgg-3' HinfI | 5'-cccgaaattccccaataaa-3' | 56 |

Note: Y = C or T, R = G or A; row 1-SEQ ID NO: 1 and 2; row 2-SEQ ID NO: 3 and 4 and so forth through to SEQ ID NO: 32, respectively. The gene sequences can be found in a gene database found at the following url address: ncbi.nim.nih.gov/UniGene/index.html.

If the sample is impure (e.g., plasma, serum, stool, ejaculate, sputum, saliva, cerebrospinal fluid, or blood or a sample embedded in paraffin), it may be treated before amplification with a reagent effective for lysing the cells contained in the fluids, tissues, or animal cell membranes of the sample, and for exposing the nucleic acid(s) contained therein. Methods for purifying or partially purifying nucleic In one embodiment, the oligonucleotide primes are specifically targeted to CACNA1G and its associated CpG islands as described herein. Examples of oligonucleotides suited for determining the methylation state of the 8 regions of the two CpG islands of MINT31/CACNA1G, as well as PCR conditions and useful methylation sensitive restriction endonucleases are set out in Table 2.

TABLE 2

Primers Useful For Bisulfite/PCR Analysis of CACNA1G

| Region | Primer set, forward/reverse | Annealing temperature (cycles) | Restriction enzyme |
|---|---|---|---|
| Region 1 | 5'-GAYGGYGTAGTAGTTATTTTGTT-3' | 58 (3), 56 (4), | BstUI |
| F165 | 5'-CATCACCACCCCTCACTTTAC-3' | 54 (5), 52 (26) | MaeII |
| Region 1 | 5'-TTYGGGTATTTATAGTTTTTTGGAG-3' | 60 (3), 58 (4), | TaqI |
| GM2 | 5'-AATCTACCRCCTTCACTCACTC-3' | 56 (5), 54 (26) | BstUI |
| Region 3 | 5'-TTTAGGAGYGTTAATGTGAGGTT-3' | 55 (3), 53 (4), | HinfI |
| GM3 | 5'-CTAAAAAAACCCAATCTTAAAAAAAC-3' | 51 (5), 49 (26) | MaeII |
| Region 4 | 5'-TGGATAAAGGATGTTTGGGGTTTG-3' | 55 (5), 53 (5), | MaeII |
| GM5 | 5'-CCCTCCCCTTACCCCTAAATCC-3' | 51 (5), 49 (26) | TaqI |
| Region 5 | 5'-AATYGGATTTTAGTTGTGGTTTTT-3' | 60 (3), 58 (4), | BstUI |
| GM1 | 5'-CACACCACAACTAAATCCCTCACT-3' | 56 (5), 54 (26) | TaqI |
| Region 6 | 5'-TTGTGGYGTTGGYGATAGTT-3' | 53 (3), 51 (4), | HinfI |
| GM6 | 5'-ACRAAAAAAAAAAAAAAAAATCTCTT-3' | 49 (5), 47 (26) | |
| Region 7 | 5'-GGGGGYGTTTTTTTTYGGATTTT-3' | 55 (3), 53 (5), | EcoRI |
| GM4 | 5'-TTCCCCTACRCCCCTAAAACTTCC-3' | 51 (5), 49 (26) | |
| Region 8 | 5'-GGGAGTTTGGGAGTTGTATTTTGTT-3' | 60 (3), 58 (4), | TaqI |
|  | 5'-AACCAAATTAAAAAATCAAACCCTAA-3' | 56 (5), 54 (26) | |
| Region 8 | 5'-GAGGGGGGATYGTAATTTTTTG-3' | 60 (3), 58 (4), | BstUI |
|  | 5'-CCRAAATCTCCTTATTATACCTCCAA-3' | 56 (5), 54 (26) | |

Region 1 F/R = SEQ ID NO: 33 and 34;
Region 2 = SEQ ID NO: 35 and 36 and so forth through Region 8 (TaqI) = SEQ ID NO: 47 and 48 and Region 8 (BstUI) = SEQ ID NO: 49 and 50.

Exemplary target regions (i.e., regions 1–8 of MINT31/CANCNA1G) that are complementary to the primers listed is Table 2 are provided in Table 3:

TABLE 3

Target Sequences

| Region/Primer | Target set, forward/reverse | SEQ ID NO | Corresponding Primer SEQ ID NO |
|---|---|---|---|
| Region 1 | 5'-AACAAAATAACTACTACRCCRTC-3' | 87 | 33 |
| F165 | 5'-GTAAAGTGAGGGGTGGTGATG-3' | 88 | 34 |
| Region 2 | 5'-CTCCAAAAAAACTATAAATACCCRAA-3' | 89 | 35 |
| GM2 | 5'-GAGTGAGTGAAGGYGGTAGATT-3' | 90 | 36 |
| Region 3 | 5'-AACCTCACATTAACRCTCCTAAA-3' | 91 | 37 |
| GM3 | 5'-GTTTTTTTAAGATTGGGTTTTTTTAG-3' | 92 | 38 |
| Region 4 | 5'-CAAACCCCAAACATCCTTTATCCA-3' | 93 | 39 |
| GM5 | 5'-GGATTTAGGGGTAAGGGGAGGG-3' | 94 | 40 |
| Region 5 | 5'-AAAAACCACAACTAAAATCCRATT-3' | 95 | 41 |
| GM1 | 5'-AGTGAGGGATTTAGTTGTGGTGTG-3' | 96 | 42 |
| Region 6 | 5'-AACTATCRCCAACRCCACAA-3' | 97 | 43 |
| GM6 | 5'-AAGAGATTTTTTTTTTTTTTTTYGT-3' | 98 | 44 |
| Region 7 | 5'-AAAATCCRAAAAAAAAACRCCCCC-3' | 99 | 45 |
| GM4 | 5'-GGAAGTTTTAGGGGYGTAGGGGAA-3' | 100 | 46 |
| Region 8 | 5'-AACAAAATACAACTCCCAAACACCC-3' | 101 | 47 |
|  | 5'-TTAGGGTTTGATTTTTTAATTTGGTT-3' | 102 | 48 |
| Region 8 | 5'-CAAAAAATTACRATCCCCCCTC-3' | 103 | 49 |
|  | 5'-TTGGAGGTATAATAAGGAGATTTYGG-3' | 104 | 50 |

TABLE 4

Targets for Bisulfite-PCR Primers

| Genes | | SEQ ID NO | Corresponding Primer SEQ ID NO |
|---|---|---|---|
| APOB 5'-target | 5'-AAAAAACCCAAACTACAAAAAC-3' | 55 | 1 |
| 3'-target | 5'-GTTGTTGGRGTTGTTGGR-3' | 56 | 2 |
| R6 5'-target | 5'-AACTATCYCCAACYCCACAA-3' | 57 | 3 |
| 3'-target | 5'-AAGAGATTTTTTTTTTTTTTRGT-3' | 58 | 4 |
| R7 5'-target | 5'-AAAATCCYAAAAAAAAACYCCCCC-3' | 59 | 5 |
| 3'-target | 5'-GGAAGTTTTAGGGGRGTAGGGGAA-3' | 60 | 6 |
| CDX2 5'-target | 5'-AACYATCCCTCCCTCTAACCTAC-3' | 61 | 7 |
| 3'-target | 5'-AGGTAGTATGGTGAGGTTTGTTTT-3' | 62 | 8 |
| EGFR 5'-target | 5'-ATCAATACTAAACRAAATCAAA-3' | 63 | 9 |
| 3'-target | 5'-AGGAAAAGAAAGGTAAGGG-3' | 64 | 10 |

TABLE 4-continued

Targets for Bisulfite-PCR Primers

| Genes | | SEQ ID NO | Corresponding Primer SEQ ID NO |
|---|---|---|---|
| FBN1 5'-target | 5'-CAAAATTAACRCAATAAAAAAA-3' | 65 | 11 |
| 3'-target | 5'-TATTTGAAGAGGTGGGGAAA-3' | 66 | 12 |
| GPR37 5'-target | 5'-AAACTCTTACCCCACCTAACC-3' | 67 | 13 |
| 3'-target | 5'-GGTTTGTAATTGGATTAAAYGTT-3' | 68 | 14 |
| HSPA6 5'-target | 5'-CCACTAACTCAAAACTAAAAAA-3' | 69 | 15 |
| 3'-target | 5'-GGGAGGTGTAAAAGGATGAAA-3' | 70 | 16 |
| IQGAP2 5'-target | 5'-CTAACACTAAAATAAAAATAAA-3' | 71 | 17 |
| 3'-target | 5'-GTAGGATGTTATAYGAAGAG-3' | 72 | 18 |
| KL 5'-target | 5'-AAACRCTAACRAACATACTAC-3' | 73 | 19 |
| 3'-target | 5'-GGGTTTTTTTTAGGGTATTT-3' | 74 | 20 |
| PAR2 5'-target | 5'-GAATTAAATTTCAAAAAAACCR-3' | 75 | 21 |
| 3'-target | 5'-TTTAGGAGGATGYGGAGTT-3' | 76 | 22 |
| PITX2 5'-target | 5'-AAAAAACCTAACRAAACACTTA-3' | 77 | 23 |
| 3'-target | 5'-GTTATTGTGTAGTGGAGTTTGG-3' | 78 | 24 |
| PTCHA 5'-target | 5'-ACTCCRATTAACAAACCAAC-3' | 79 | 25 |
| 3'-target | 5'-AATATGGTTTYGGTTGGTAA-3' | 80 | 26 |
| PTCHB 5'-target | 5'-TCCCTAAATTCCACACATT-3' | 81 | 27 |
| 3'-target | 5'-GTAAGTTGTAGTTGGTTGTTTTA-3' | 82 | 28 |
| SDC1 5'-target | 5'-CTCTCTACTACCRAATTCCTCT-3' | 83 | 29 |
| 3'-target | 5'-GTTTTGGTTTTGGTTGTG-3' | 84 | 30 |
| SDC4 5'-target | 5'-CCACTACCAAACAAATCCCC-3' | 85 | 31 |
| 3'-target | 5'-TTTATTGGGGAATTTCGGG-3' | 86 | 32 |

TABLE 5

New genes differentially methylated in disease versus normal tissue

| Gene Symbol | Gene name | Map | Unigene Entry[1] | Methylated in[2] |
|---|---|---|---|---|
| APOB | Apolipoprotein B | 2p24 | Hs.585 | Common Tumors |
| CACNAIG | T-type calcium channel | 17 | — | |
| CDX2 | Caudal type homeo box transcription factor 2 | 13q12.3 | Hs.77399 | Leukemias, breast, prostate |
| EGFR | Epidermal Growth Factor Receptor | 7p12 | Hs.77432 | Leukemias, breast |
| FBN1 | Fibrillin-1 | 15q21.1 | Hs.750 | Colon, Breast, prostate, leukemias |
| GPR37 | G protein-coupled receptor 37 | 7q31 | Hs.27747 | colon, breast, leukemias |
| HSPA6 | Heat shock 70 kD protein 6 (HSP70B') | 1q | Hs.3268 | Common tumors |
| IQGAP2 | RasGAP-related protein | 5q | Hs.78993 | Common tumors |
| KL | Klotho | — | Hs.94592 | Common tumors |
| PAR2 | Proteinase-activated receptor 2 | 5q13 | Hs.154299 | Leukemias, breast |
| PITX2 | Paired-like homeodomain transcription factor 2 | 4q25–27 | Hs.92282 | Leukemias, prostate, breast |
| PTCH[3] | Patched | 9Q31 | Hs.159526 | Leukemias |
| SDC1 | Syndecan 1 | 2p24.1 | Hs.82109 | Leukemias |
| SDC4 | Syndecan 4 | 20q12 | Hs.72082 | Leukemias |

Table 5: New genes differentially methylated in cancer and other diseases.
[1]Gene database that can be found at http://www.ncbi.nim.nih.gov/UniGene/index.html.
[2]Examples: List is not comprehensive.
[3]Two promoters are affected.

In another embodiment, detection of differential methylation is accomplished by contacting a nucleic acid sample suspected of comprising a CpG-containing nucleic acid with a methylation sensitive restriction endonuclease that cleaves only unmethylated CpG sites under conditions and for a time to allow cleavage of unmethylated nucleic acid. The sample is further contacted with an isoschizomer of the methylation sensitive restriction endonuclease, that cleaves both methylated and unmethylated CpG-sites, under conditions and for a time to allow cleavage of methylated nucleic acid. Oligonucleotides are added to the nucleic acid sample under conditions and for a time to allow ligation of the oligonucleotides to nucleic acid cleaved by the restriction endonuclease, and the digested nucleic acid is amplified by conventional methods such as PCR wherein primers complementary to the oligonucleotides are employed. Following identification, the methylated CpG-containing nucleic acid can be cloned, using method well known to one of skill in the art (see Sambrook et al., *Molecular Cloning: a Laboratory Manual*, Cold Spring Harbor Press 1989).

As used herein, a "methylation sensitive restriction endonuclease" is a restriction endonuclease that includes CG as part of its recognition site and has altered activity when the C is methylated as compared to when the C is not methylated. Preferably, the methylation sensitive restriction endonuclease has inhibited activity when the C is methylated (e.g., SmaI). Specific non-limiting examples of a methylation sensitive restriction endonucleases include SmaI, BssHII, or HpaII. Such enzymes can be used alone or in combination. Other methylation sensitive restriction endonucleases will be known to those of skill in the art and include, but are not limited to SacII, EagI, and BstUI, for example. An "isoschizomer" of a methylation sensitive restriction endonuclease is a restriction endonuclease which recognizes the same recognition site as a methylation sensitive restriction endonuclease but which cleaves both methylated and unmethylated CGs. One of skill in the art can readily determine appropriate conditions for a restriction endonuclease to cleave a nucleic acid (see Sambrook et al., *Molecular Cloning: a Laboratory Manual*, Cold Spring Harbor Press, 1989). Without being bound by theory, actively transcribed genes generally contain fewer methylated CGs than in other genes.

In one embodiment of the invention, a nucleic acid of interest is cleaved with a methylation sensitive endonuclease. In one aspect, cleavage with the methylation sensitive endonuclease creates a sufficient overhang on the nucleic acid of interest. Following cleavage with the isoschizomer, the cleavage product can still have a sufficient overhang. An "overhang" refers to nucleic acid having two strands wherein the strands end in such a manner that a few bases of one strand are not base paired to the other strand. A "sufficient overhang" refers to an overhang of sufficient length to allow specific hybridization of an oligonucleotide of interest. In one embodiment, a sufficient overhang is at least two bases in length. In another embodiment, the sufficient overhang is four or more bases in length. An overhang of a specific sequence on the nucleic acid of interest may be desired in order for an oligonucleotide of interest to hybridize. In this case, the isoschizomer can be used to create the overhang having the desired sequence on the nucleic acid of interest.

In another aspect of this embodiment, the cleavage with a methylation sensitive endonuclease results in a reaction product of the nucleic acid of interest that has a blunt end or an insufficient overhang. In this embodiment, an isoschizomer of the methylation sensitive restriction endonuclease can create a sufficient overhang on the nucleic acid of interest. "Blunt ends" refers to a flush ending of two strands, the sense strand and the antisense strand, of a nucleic acid.

Once a sufficient overhang is created on the nucleic acid of interest, an oligonucleotide is ligated to the nucleic acid cleaved of interest which has been cleaved by the methylation specific restriction endonuclease. "Ligation" is the attachment of two nucleic acid sequences by base pairing of substantially complementary sequences and/or by the formation of covalent bonds between two nucleic acid sequences. In one aspect of the present invention, an "oligonucleotide" is a nucleic acid sequence of about 2 up to about 40 bases in length. It is presently preferred that the oligonucleotide is from about 15 to 35 bases in length.

In one embodiment, an adaptor is utilized to create DNA ends of desired sequence and overhang. An "adapter" is a double-stranded nucleic acid sequence with one end that has a sufficient overhang at one or both ends such that the adaptor can be ligated by base-pairing to a sufficient overhang on a nucleic acid of interest that has been cleaved by a methylation sensitive restriction enzyme or an isoschizomer of a methylation sensitive restriction enzyme. Adaptors can be obtained commercially, or two oligonucleotides can be utilized to form an adaptor. Thus, in one embodiment, two oligonucleotides are used to form an adapter, these oligonucleotides are substantially complementary over their entire sequence except for the region(s) at the 5' and/or 3' ends that will form a single stranded overhang. The single stranded overhang is complementary to an overhang on the nucleic acid cleaved by a methylation sensitive restriction enzyme or an isoschizomer of a methylation sensitive restriction enzyme, such that the overhang on the nucleic acid of interest will base pair with the 3' or 5' single stranded end of the adapter under appropriate conditions. The conditions will vary depending on the sequence composition (GC vs AT), the length, and the type of nucleic acid (see Sambrook et al. *Molecular Cloning: a Laboratory Manual*, 2nd Ed.; Cold Spring Harbor Laboratory Press, Plainview, N.Y., 1998).

Following the ligation of the oligonucleotide, the nucleic acid of interest is amplified using a primer complementary to the oligonucleotide. Specifically, the term "primer" as used herein refers to a sequence comprising two or more deoxyribonucleotides or ribonucleotides, preferably more than three, and more preferably more than eight, wherein the sequence is capable of initiating synthesis of a primer extension product, which is substantially complementary to a nucleic acid such as an adaptor or a ligated oligonucleotide. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. In one embodiment, the primer is an oligodeoxyribo-nucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the oligonucleotide to be amplified and include the appropriate G or C nucleotides as discussed above. This means that the primers must be sufficiently complementary to hybridize with their respective strands under conditions which allow the agent for polymerization to perform. In other words, the primers should have sufficient complementarity with a 5' and 3' oligonucleotide to hybridize therewith and permit amplification of CpG containing nucleic acid sequence.

Primers of the invention are employed in the amplification process which is an enzymatic chain reaction that produces exponential quantities of target locus relative to the number of reaction steps involved (e.g., polymerase chain reaction or PCR). Typically, one primer is complementary to the negative (−) strand of the locus and the other is complementary to the positive (+) strand. Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphos-phoramidites are used as starting materials and may be synthesized as described by Beaucage, et al. (Tetrahedron Letters, 22:1859–1862, 1981). One method for synthesizing oligonucleotides on a modified solid support is described in U.S. Pat. No. 4,458,166.

Where the CpG-containing nucleic acid sequence of interest contains two strands, it is necessary to separate the strands of the nucleic acid before it can be used as a template for the amplification process. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hofmann-Berling (CSH-Quantitative Biology, 43:63, 1978) and techniques for using RecA an reviewed in C. Radding (Ann. Rev. Genetics, 16:405–437, 1982).

When complementary strands of nucleic acid or acids are eparated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, generally at a pH of about 7–9. Preferably, a molar excess (for genomic nucleic acid, usually about 108:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands, a large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to approximately room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation such as Taq DNA polymerase, and the like). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

Preferably, the method of amplifying is by PCR, as described herein and as is commonly used by those of ordinary skill in the art. However, alternative methods of amplification have been described and can also be employed. PCR techniques and many variations of PCR are known. Basic PCR techniques are described by Saiki et al. (1988 Science 239:487–491) and by U.S. Pat. Nos. 4,683,195, 4,683,202 and 4,800,159, which are incorporated herein by reference.

The conditions generally required for PCR include temperature, salt, cation, pH and related conditions needed for efficient copying of the master-cut fragment. PCR conditions include repeated cycles of heat denaturation (i.e. heating to at least about 95 degree, C.) and incubation at a temperature permitting primer: adaptor hybridization and copying of the master-cut DNA fragment by the amplification enzyme. Heat stable amplification enzymes like the pwo, *Thermus aquaticus* or *Thermococcus litoralis* DNA polymerases are commercially available which eliminate the need to add enzyme after each denaturation cycle. The salt, cation, pH and related factors needed for enzymatic amplification activity are available from commercial manufacturers of amplification enzymes.

As provided herein an amplification enzyme is any enzyme which can be used for in vitro nucleic acid amplification, e.g. by the above-described procedures. Such amplification enzymes include pwo, *Escherichia coli* DNA polymerase I, Klenow fragment of *E. coli* DNA polymerase 1, T4 DNA polymerase, T7 DNA polymerase, *Thermus aquaticus* (Taq) DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Q.beta. replicase. Preferred amplification enzymes are the pwo and Taq polymerases. The pwo enzyme is especially preferred because of its fidelity in replicating DNA.

Once amplified, the nucleic acid can be attached to a solid support, such as a membrane, and can be hybridized with any probe of interest, to detect any nucleic acid sequence. Several membranes are known to one of skill in the art for the adhesion of nucleic and sequences. Specific non-limiting examples of these membranes include nitrocellulose (NITROPURE) or other membranes used in for detection of gene expression such as polyvinylchloride, diazotized paper and other commercially available membranes such as GENESCREEN, ZETAPROBE (Biorad), and NYTRAN Methods for attaching nucleic acids to these membranes are well known to one of skill in the art. Alternatively, screening can be done in a liquid phase.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT convent), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows; 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending an the particular hybridization reaction involved, and can be determined empirically. In general, conditions of high stringency are used for the hybridization of the probe of interest.

The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

In one embodiment, representational difference analysis (RDA, see Lisitsyn et al., Science 259:946–951, 1993, herein incorporated by reference) an be performed on CpG-containing nucleic acid following MCA. MCA utilizes kinetic and subtractive enrichment to purify restriction endonuclease fragments present in one population of nucleic acid fragments but not in another. Thus, RDA enables the identification of small differences between the sequences of two nucleic acid populations. RDA uses nucleic acid from one population as a "tester" and nucleic acid from a second population as a "driver" in order to clone probes for single copy sequences present in (or absent from) one of the two populations. In one embodiment, nucleic acid from a "normal" individual or sample, not having a disorder such as a cell-proliferative disorder is used as a "driver," and nucleic acid from an "affected" individual or sample, having the disorder such as a cell proliferative disorder is used as a "tester." In one embodiment, the nucleic acid used as a "tester" is isolated from an individual having a cell proliferative disorder such as low grade astrocytoma, anaplastic astrocytoma, glioblastoma, medulloblastoma, gastric cancer, colorectal cancer, colorectal adenoma, acute myelogenous leukemia, leukemia, lung cancer, renal cancer, breast cancer, prostate cancer, endometrial cancer and neuroblastoma. The nucleic acid used as a "driver" is thus normal astrocytes, normal glial cells, normal brain cells, normal gastric cells, normal colorectal cells, normal leukocytes, normal lung cells, normal kidney cells, normal breast cells, normal prostate cells, normal uterine cells, and normal neurons, respectively. In an additional embodiment, the nucleic acid used as a "driver" is isolated from an individual having a cell proliferative disorder such as low grade astrocytoma, anaplastic astrocytoma, glioblastoma, medulloblastoma, gastric cancer, colorectal cancer, colorectal adenoma, acute myelogenous leukemia, leukemia, lung cancer, renal cancer, breast cancer, prostate cancer, endometrial cancer and neuroblastoma. The nucleic acid used as a "tester" is thus normal astrocytes, normal filial cells, normal brain cells, normal gastric cells, normal colorectal cells, normal leukocytes, normal lung cells, normal kidney cells, normal breast cells, normal prostate cells, normal uterine cells, and normal neurons, respectively. One of skill in the art will readily be able to identify the "tester" nucleic acid useful with to identify methylated nucleic acid sequences in given "driver" population.

KITS

The materials for use in the assay of the invention are ideally suited for the preparation of a kit. Therefore, in accordance with another embodiment of the present invention, there is provided a kit it useful for the detection of a cellular proliferative disorder in a subject having or at risk for said cellular proliferative disorder. Invention kits include a carrier means compartmentalized to receive a sample in close confinement therein, one or more containers comprising a first container containing a reagent which modifies unmethylated cytosine and a second container containing primers for amplification of a CpG-containing nucleic acid, wherein the primers distinguish between modified methylated and nonmethylated nucleic acid, and optionally, a third container containing a methylation sensitive restriction endonuclease. Primers contemplated for use in accordance with the invention include those set forth in SEQ ID NOs: 1–50.

Carrier means are suited for containing one or more container means such as vials, tubes, and the like, each of the container means comprising one of the separate elements to be used in the method. In view of the description provided herein of invention methods, those of skill in the art can readily determine the apportionment of the necessary regents among the container means. For example, one of the container means are comprise a container containing an oligonucleotide for ligation to nucleic acid cleaved by a methylation sensitive restriction endonuclease. One or more container mesas can also be included comprising a primer complementary to the oligonucleotide. In addition, one or more container means can also be included which comprise a methylation sensitive restriction endonuclease. One or more container means can also be included containing in isoschizomer of said methylation sensitive restriction enzyme.

In another embodiment, the kit may comprise a carrier means containing one or more container means comprising a solid support, wherein the solid support has a nucleic acid sequence of CACNA1G as described herein immobilized on the solid support. In one embodiment, the solid support is a membrane. Several membranes are known to one of skill in the art for the adhesion of nucleic acid sequences. Specific non-limiting examples of these membranes include nitrocellulose (Nitropure) or other membranes used in for detection of gene expression such as polyvinylchloride, diazotized paper and other commercially available membranes such as GENESCREEN, ZETAPROBE (Biorad), and NYTRAN The CACNA1G sequences immobilized on the solid support can then be hybridized to nucleic acid sequences produced by performing the MCA procedure, bisulfite PCR or other methylation detection methods on the nucleic acids of a sample of interest in order to determine if the nucleic acid sequences contained in the sample are methylated.

The term "oligonucleotide primer" refers to a sequence of two or more deoxyribonucleotides or ribonucleotides, preferably at least eight, which sequence is capable of initiating synthesis of a primer extension product that is substantially complementary to a target nucleic acid sound. The oligonucleotide primer typically contains fifteen to twenty-two or more nucleotides, although it may contain fewer nucleotides if the primer is complementary, so as to specifically allow the amplification of the specifically desired target nucleotide sequence.

The oligonucleotide primers for use in the invention may be prepared using any suitable method, such as conventional phosphotriester and phosphodiester methods or automated embodiments thereof. In one such automated embodiment, diethyl-phosphoramidites are used as starting materials and may be synthesized as described by Beaucage et al., Tetrahedron Letter, 22:1859–1862 (1981). One method for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the method of the invention are complementary to each strand of mutant nucleotide sequence to be amplified. The term "complementary" means that the primers must hybridize with their respective strands under conditions which allow the agent for polymerization to function. In other words, the primers that are complementary to the flanking sequences hybridize with the flanking sequences and permit amplification of the nucleotide sequence. Preferably, the 3' terminus of the primer that is extended has perfectly base paired complementarity with the complementary flanking strand.

The term "flanks CpG-rich regions" refers to those DNA sequences on chromosome that are upstream (5') or downstream (3') to the DNA sequence to be amplified. The sequence to be amplified is preferably a CpG-rich region in a gene or regulatory region associated with a gene. For example, when the nucleotide sequence to be amplified is double stranded, a first sequence that is 5' to the nucleotide sequence and a second sequence that is 5' to the nucleotide sequence on the complementary strand flank the CpG-rich DNA sequence.

The nucleotide sequences that flank nucleotide repeats, i.e., the nucleotide sequences to which the oligonucleotide primers hybridize, may be selected from among the following nucleotide sequences: SEQ ID NO:1–50.

In general, the primers used according to the method of the invention embrace oligonucleotides of sufficient length and appropriate sequence which provide specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Oligonucleotide primers used according to the invention are employed in any amplification process that produces increased quantities of target nucleic acid.

The invention includes antibodies immunoreactive with CACNA1G polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., Nature, 256:495, 1975). The term antibody as used in this invention is meant to include intact molecules as well as fragments thereof, such as Fab and F(ab')$_2$, Fv and SCA fragments which are capable of binding an epitope determinant on CACNA1G.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

As used in this invention, the term "epitope" refers to an antigenic determinant on an antigen, such as a CACNA1G polypeptide, to which the paratope of an antibody, such as an CACNA1G-specific antibody, binds. Antigenic determinants usually consist of chemically active surface groupings of molecules, such as amino acids or sugar side chains, and can have specific three-dimensional structural characteristics, as well as specific charge characteristics.

As is mentioned above, antigens that can be used in producing CACNA1G-specific antibodies include CACNA1G polypeptides or CACNA1G polypeptide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

The invention also provides a method for detecting a cell proliferative disorder associated with CACNA1G in a subject, comprising contacting a target cellular component suspected of having a CACNA1G associated disorder, with a reagent which reacts with or binds to CACNA1G and detecting CACNA1G. The target cell component can be nucleic acid, such as DNA or RNA, or it can be protein. When the component is nucleic acid, the reagent is typically a nucleic acid probe or PCR primer. When the cell component is protein, the reagent is typically an antibody probe. The target cell component may be detected directly in situ or it may be isolated from other cell components by common methods known to those of skill in the art before contacting with a probe. (See for example, Maniatis, et al., Molecular Cloning, A Laboratory Manual, Cold Spring Harbor Laboratory, N.Y. 1989; Current Protocols in Molecular Biology, 1994, Ed. Ausubel, et al., Green Publ. Assoc. & Wiley Interscience.) Detection methods include Southern and Northern blot analyses, RNase protection, immunoassays and other detection assays that are known to those of skill in the art.

The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probes or will be able to ascertain such, using routine experimentation.

Since the present invention shows that a decreased level of CACNA1G transcription is often the result of hypermethylation of the CACNA1G gene, it is often desirable to directly determine whether the CACNA1G gene is hypermethylated. In particular, the cytosine rich areas terms "CgG islands" which lie in the 5' regulatory regions of genes are normally unmethylated. The term "hypermethylation" includes any methylation of cytosine which is normally unmethylated in the CACNA1G gene sequence can be detected by restriction endonuclease treatment of CACNA1G polynucleotide (gene) and Southern blot analysis for example. Therefore, in a method of the invention, when the cellular component detected is DNA, restriction endonuclease analysis is preferable to detect hypermethylation of the CACNA1G gene. Any restriction endonuclease that includes CG as part of its recognition site and that is inhibited when the C is methylated, can be utilized. Methylation sensitive restriction endonucleases such as BssHII, MspI, NotI or HpaII, used alone or in combination are examples of such endonucleases. Other methylation sensitive restriction endonucleases will be known to those of skill in the art. In addition, PCR can be utilized to detect the methylation status of the CACNA1G gene. Oligonucleotide primers based on any coding sequence region in the CACNA1G sequence are useful for amplifying DNA by PCR. CACNA1G is described here for exemplary purposes. The other genes described herein as being For purposes of the invention, an antibody or nucleic acid probe specific for CACNA1G may be used to detect the presence of CACNA1G polypeptide (using antibody) or polynucleotide (using nucleic acid probe) in biological fluids or tissues. Oligonucleotide primers based on any coding sequence region in the CACNA1G sequence are useful for amplifying DNA, for example by PCR. Any specimen containing a detectable amount of CACNA1G polynucleotide or CACNA1G polypeptide antigen can be used. Nucleic acid can also be analyzed by RNA in situ methods which are known to those of skill in the art. A preferred sample of this invention is tissue of heart, renal, brain, colon, breast, urogenital, uterine, hematopoietic, prostate, thymus, lung, testis, and ovarian. Preferably the subject is human.

Various disorders which are detectable by the method of the invention include astrocytoma, anaplastic astrocytoma, glioblastoma, medulloblastoma, colon cancer, lung cancer, renal cancer, leukemia, breast cancer, prostate cancer, endometrial cancer and neuroblastoma.

Monoclonal antibodies used in the method of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of CACNA1G. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-CACNA1G immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1–100 $\mu g/\mu l$) may be important, in order to maintain the proper sensitivity yet inhibit any unwanted interference by mutually occurring cross reactive proteins in the specimen.

In using a monoclonal antibody for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the CACNA1G antigen for which the monoclonal antibodies are specific. The concentration of detectably labeled monoclonal antibody which is administered should be sufficient such that the binding to those cells having CACNA1G is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.001 mg/m.sup.2 to about 500 mg/m.sup.2, preferably 0.1 mg/m.sup.2 to about 200 mg/m.sup.2, most preferably about 0.1 mg/m.sup.2 to about 10 mg/m.sup.2. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a1 type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentactic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

A monoclonal antibody useful in the method of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The present invention also provides a method for treating a subject with a cell proliferative disorder associated with of CACNA1G comprising administering to a subject with the disorder a therapeutically effective amount of reagent which modulates CACNA1G expression. In brain, breast and renal cancer cells, for example, the CACNA1G nucleotide sequence is under-expressed as compared to expression in a normal cell, therefore, it is possible to design appropriate therapeutic or diagnostic techniques directed to this sequence. Thus, where a cell-proliferative disorder is associated with the expression of CACNA1G associated with malignancy, nucleic acid sequences that modulate CACNA1G expression at the transcriptional or translational level can be used. In cases when a cell proliferative disorder or abnormal cell phenotype is associated with the under expression of CACNA1G, for example, nucleic acid sequences encoding CACNA1G (sense) could be administered to the subject with the disorder.

The term "cell-proliferative disorder" denotes malignant as well as non-malignant cell populations which often appear to differ from the surrounding tissue both morphologically and genotypically. Such disorders may be associated, for example, with absence of expression of CACNA1G. Essentially, any disorder which is etiologically linked to expression of CACNA1G could be considered susceptible to treatment with a reagent of the invention which modulates CACNA1G expression.

The term "modulate" envisions the suppression of methylation of CACNA1G polynucleotide when CACNA1G is under-expressed. When a cell proliferative disorder is associated with CACNA1G expression, such methylation suppressive reagents as 5-azacytadine can be introduced to a cell.. Alternatively, when a cell proliferative disorder is associated with under-expression of CACNA1G polypeptide, a sense polynucleotide sequence (the DNA coding strand) encoding CACNA1G polypeptide, or 5' regulatory nucleotide sequences (i.e., promoter) of CACNA1G in operable linkage with CACNA1G polynucleotide can be introduced into the cell. Demethylases known in the art could also be used to remove methylation.

The present invention also provides gene therapy for the treatment of cell proliferative disorders which are mediated by CACNA1G. Such therapy would achieve its therapeutic effect by introduction of the appropriate CACNA1G polynucleotide which contains a CACNA1G structural gene (sense), into cells of subjects having the proliferative disorder. Delivery of sense CACNA1G polynucleotide constructs can be achieved using a recombinant expression vector such as a chimeric virus or a colloidal dispersion system.

The polynucleotide sequences used in the method of the invention may be the native, unmethylated sequence or, alternatively, may be a sequence in which a nonmethylatable analog is substituted within the sequence. Preferably, the analog is a nonmethylatable analog of cytidine, such as 5-azacytadine. Other analogs will be known to those of skill in the art. Alternatively, such nonmethylatable analogs could be administered to a subject as drug therapy, alone or simultaneously with a sense structural gene for CACNA1G or sense promoter for CACNA1G operably linked to CACNA1G structural gene.

In another embodiment, a CACNA1G structural gene is operably linked to a tissue specific heterologous promoter and used for gene therapy. For example, a CACNA1G gene can be ligated to prostate specific antigen (PSA)-prostate specific promoter for expression of CACNA1G in prostate tissue. Other tissue specific promoters will be known to those of skill in the art. Alternatively, the promoter for a tumor suppressor gene can be linked to the CACNA1G structural gene and used for gene therapy.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Most preferably, a non-human primate retroviral vector is employed, such as the gibbon ape leukemia virus (GaLV), thereby providing a broader host range than murine vectors, for example.

A number of additional retroviral vectors can incorporate multiple genes. All of these vectors can transfer or incorporate a gene for a selectable marker so that transduced cells can be identified and generated. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the CACNA1G sense or antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to .PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system for CACNA1G polynucleotide is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size of 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The compositions of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting CACNA1G antibody-containing liposomes directly to the malignant tumor. Since the CACNA1G gene product may be indiscriminate with respect to cell type in its action, a targeted delivery system offers a significant improvement over randomly injecting non-specific liposomes. Preferably, the target tissue is human brain, colon, breast, lung, and renal origin. A number of procedures can be used to covalently attach either polyclonal or monoclonal antibodies to a liposome bilayer. Antibody-targeted liposomes can include monoclonal or polyclonal antibodies or fragments thereof such as Fab, or F(ab').sub.2, as long as they bind efficiently to an antigenic epitope on the target cells. Liposomes may also be targeted to cells expressing receptors for hormones or other serum factors.

It should be noted that as used herein and in the appended claims, the singular forms "a," "and," and "the" include plural referents unless the context clearly dictates otherwise. Thus, for example, reference to "a cell" includes a plurality of such cells and reference to "the restriction enzyme" includes reference to one or more restriction enzymes and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the methodologies which are described in the publications which might can used in connection with the presently described invention. The publications discussed above and throughout the text are provided solely for their disclosure prior to the filing data of the present application. Nothing herein is to be construed as an admission that the inventors are not entitled to antedate such disclosure by virtue of prior invention.

The following example is intended to illustrate but not to limit the invention in any manner, shape, or form, either explicitly or implicitly. While they are typical of those that might be used, other procedures, methodologies, or techniques known to those skilled in the art may alternatively be used.

EXAMPLE 1

Identification of CACNA1G as a Target for Hypermethylation on Human Chromosome 17q21

In order to isolate genes differentially methylated in cancer cells as opposed to non-cancerous cells the following experimental protocols were used. An example of the results obtained is provided hereinabove in the description of the isolation and characterization of human CANNA1G.

Tissue Samples and Cell Lines

Forty-nine primary colorectal cancers, 28 colorectal adenomas, 16 primary gastric cancers and 17 acute myelogenous leukemia samples were used for methylation analyses. DNA from eight colon cancer cell lines (Caco2, RKO, SW48, HCT116, DLD1, Lovo, SW837, HT29), 4 lung cancer cell lines (OH3, H249, H157, H209), 4 glioblastoma cell fines (Dauy, D283, U87, U373), 8 breast cancer cell lines (MB-468, MCF7, MB-231, MB-474, MB-435, MB-453, BT20, CAMA1, SKBR3), 7 hematopoietic tumor cell lines (CEM, Raji, KG1A, HL60, ML-1,MoIt3, K562), and 4 prostate cancer cell lines (DU145, DUPRO, LNCAP, TSUPRL) were also investigated. DNA was extracted by standard procedures. RNA was isolated from cell lines and adenomas using TRIZOL (GIBCO-BRL). For re-expression analysis, cell lines were treated with 5-Aza-deoxycytidine (SIGMA) at a final concentration of 1 M for 6 days. All tissue samples were obtained from patients who gave informed consent according to institutional guidelines.

RT-PCR

Six g of total RNA, was reverse transcribed using the SUPERSCRIPT kit (GIBCO-BRL) for first strand cDNA synthesis. One hundred ng of cDNA was used as template for RT-PCR reactions. To design the RT-PCR primers. Blast search was performed using the rat Cacna1G cDNA sequence (Genbank AF027984) reported previously (25) and exon-intron boundaries of the human CACNA1G were predicted by this analysis. Each primer set was designed to amplify the cDNA across several introns. Primer sequences and PCR conditions are available, at the following uniform resource locator (url): med.jhu.edu/methylation/primers. GAPDH was also amplified as a control using primers GAPDHF: 5'-CGGAGTCAACGGATTGGTCGTAT-3' (SEQ ID NO:55) and GAPDHR: 5'-AGCCTTCTCC ATGGTGGTGAAGAC-3' (SEQ ID NO:56). All reactions were performed with RT(-) controls. PCR amplification was performed for 35 cycles of 95° C. 30 sec, 60–65° C. for 30 sec, 72° C. for 30 sec, and the products were analyzed by agarose gel electrophoresis.

DNA Sequencing and Data Analysis

PCR reaction products were precipitated with ethanol, resuspended in diluted water and cloned into the pCR2.1 vector using the TA cloning kit (Invitrogen) according to the manufacturer's instruction. After transformation, plasmid DNA purified using the Wizard Miniprep Kit (Promega). DNA sequence analysis was carried out at the Johns Hopkins University Sequence Facility using automated DNA sequencers (Applied Biosystems). Sequence homology was identified by the BLAST program of the National Center for Biological Information (NCBI) available at the following uniform resource (url): ncbi.nlm.nih.gov/BLAST/. An IMAGE cDNA clone (Genbank: H13333) was identified by BLAST analysis using the sequence of BAC AC004590 (Genbank) which includes MINT31. Putative genes (G1 and G2) were identified by GENSCAN (available at the following uniform resource locator (url): ccr-081.mit.edu/GENSCANMIT.htm1) using the BAC sequence data. IMAGE cDNA clone H1333) was then obtained from the American Type Culture Collection and completely sequenced. Potential transcription factor binding sites and promoter prediction were examined using the TESS and TSSG programs respectively, available at the Baylor College of Medicine BCM Launcher the following uniform resource locator (url): kiwi.imgen.bcm.tme.edu:8088/searchlauncher/launcher.html/). The nucleotide sequence of part of the 5' end of the cDNA of CACNA1G has been submitted to Genbank.

Bisulfite-PCR Methylation Analysis

Bisulfite treatment was performed as reports previously. (Herman, J. G., Graff, J. R., Myohanen, S., Nelkin. B. D. and Baylin, S. B. Proc. Natl. Acad. Sci. USA. 93:9821–9826, 1996). Briefly, 2 g of genomic DNA was denatured with 2 M NaOH for 10 min., followed by incubation with 3 M Na-bisulfite, pH 5.0 for 16 hours at 50° C. After treatment DNA was purified using a Wizard Miniprep Column (Promega), precipitated with ethanol and resuspended in 20 l of diluted water. Two l of the aliquot was used as template for each PCR reaction. Semi-quantitative bisulfite-PCR was performed essentially as described. Xiong, Z. and Laird, P. W. COBRA: a sensitive and quantitative DNA methylation assay. Nucleic Acids Res. 25:2532–2534, 1997. To avoid overestimation of the methylated alleles, the following points were considered. First, primers were designed to contain a minimum number of CpG dinucleotides in the sequence to avoid the biased amplification of methylated alleles. If primers do contain CpG sites, they were designed to amplify methylated and unmethylated alleles equally (using a mixture of C or T for sense and a mixture of G or A for antisense primers). Second, the primers were designed to contain a maximum number of thymidines converted from cytosines to avoid amplifying the non-converted genomic sequence. Third, restriction sites which only appear after bisulfite conversion (e.g. ACGC to ACGT) were used (regions 1–8). PCR was performed as described previously (Herman, supra). Primer sequences, annealing temperature and PCR cycles are available at http://www.jhu.edu/methylation/primers. Twenty % of the PCR products were digested with the appropriate restriction enzymes, precipitated with ethanol and separated by 5% polysacrylamide gel electrophoresis. Gels were stained with ethidium bromide, and the intensity of each allele was calculated by densitometry, using the Image Quant software (Molecular Dynamics).

Although the invention has been described with reference to the presently preferred embodiment, it should be understood that various modifications can be made without departing from the spirit of the invention. Accordingly, the invention is limited only by the following claims.

What is claimed is:

1. A method for detecting colorectal adenoma or a cancer other than glioma, comprising:
    a) contacting a nucleic acid-containing specimen from a subject with an agent that provides a determination of the methylation state of at least one of a first region and a second region of a CpG island of CACNA1G, wherein the first region is a region of the CACNA1G CpG island that is amplified by SEQ ID NO:33 and SEQ ID NO:34, and wherein the second region is a region of the CACNA1G CpG island that is amplified by SEQ ID NO:35 and SEQ ID NO:36, and
    b) detecting hypermethylation of at least one of the first region and the second region, wherein hypermethylation of at least one of the first region and the second region as compared to the same region of the CACNA1G gene in a subject not having colorectal adenoma or a cancer other than glioma is indicative of the colorectal adenoma or cancer other than glioma.

2. The method of claim 1, wherein the agent is a pair of primers that amplify the first region or the second region.

3. The method of claim 2, wherein the primer pair is SEQ ID NOS: 33 and 34, or SEQ ID NOS: 35 and 36.

4. The method of claim 1, wherein the nucleic acid-containing specimen comprises a tissue selected from the group consisting of brain, colon, urogenital, lung, renal, prostate, pancreas, liver, esophagus, stomach, hematopoietic, breast, thymus, testis, ovarian, and uterine.

5. The method of claim 1, wherein the nucleic acid-containing specimen is selected from the group consisting of serum, urine, saliva, blood, cerebrospinal fluid, pleural fluid, ascites fluid, sputum, stool, and biopsy sample.

6. A method for detecting a colorectal adenoma or a cancer other than glioma, the method comprising contacting a nucleic acid-containing specimen from a subject with SEQ ID NO:33 and SEQ ID NO:34 or with SEQ ID NO:35 and SEQ ID NO:36, wherein SEQ ID NO:33 and SEQ ID NO:34 are a primer pair for amplification of a first region of a CACNA1G CpG island, and wherein SEQ ID NO:35 and SEQ ID NO:36 are a primer pair for amplification of a second region of the CACNA1G CpG island, wherein hypermethylation of one or both of the first region and the second region of the CACNA1G CpG island is indicative of the presence of the colorectal adenoma or the cancer other than glioma, thereby detecting the colorectal adenoma or the cancer other than glioma.

7. The method of claim 6, wherein the cancer is colorectal cancer, colorectal adenoma, gastric cancer, lung cancer, breast cancer, hematopoietic tumors, prostate cancer, or acute myeloid leukemia (AML).

8. The method of claim 6, wherein the cancer is medulloblastoma, lung cancer, renal cancer, endometrial cancer or neuroblastoma.

9. The method of claim 6, wherein the cancer is colorectal cancer, gastric cancer, or acute myelogenous leukemia (AML).

10. The method of claim 6, wherein the method further comprises contacting the nucleic acid-containing specimen from the subject with a primer pair for amplifying a fourth region of the CACNA1G CpG island wherein the primer pair is SEQ ID NO:39 and SEQ ID NO:40, a fifth region of the CACNA1G CpG island wherein the primer pair is SEQ ID NO:41 and SEQ ID NO:42, a sixth region of the CACANA1G CpG island wherein the primer pair is SEQ ID NO:43 and SEQ ID NO:44, a seventh region of the CACNA1G CpG island wherein the primer pair is SEQ ID NO:45 and SEQ ID NO:46, or an eighth region of the CACNA1G CpG island wherein the primer pair is SEQ ID NO:47 and SEQ ID NO:48, and wherein hypermethylation of one or more of the fourth region, the fifth region, the sixth region, the seventh region, or the eighth region of the CACNA1G CpG island is indicative of the presence of the cancer other than glioma or colorectal adenoma.

11. A method for detecting colorectal adenoma, colorectal cancer, gastric cancer, or acute myelogenous leukemia (AML), comprising:

a) contacting a nucleic acid-containing specimen from a subject with an agent that provides a determination of the methylation state of at least one of a fifth region, a sixth region, and a seventh region of a CpG island of a CACNA1G, wherein the fifth region is the region of the CACNA1G CpG island that is amplified by SEQ ID NO:41 and SEQ ID NO:42, wherein the sixth region is the region of the CACNA1G CpG island that is amplified by SEQ ID NO:42 and SEQ ID NO:43 and wherein the seventh region is the region of the CACNA1G CpG island that is amplified by SEQ ID NO:44 and SEQ ID NO:45, and b) detecting hypermethylation of at least one of the fifth region, the sixth region, and the seventh region, wherein hypermethylation of at least one of the fifth region, the sixth region, and the seventh region as compared to the same region of the CACNA1G gene is a subject not having colorectal adenoma, colorectal cancer, gastric cancer, or AML is indicative of the colorectal adenoma, colorectal cancer, or gastric cancer, or AML.

12. A method for detecting colorectal adenoma, colorectal cancer, gastric cancer, or acute myelogenous leukemia (AML), comprising contacting a nucleic acid-containing specimen from a subject with SEQ ID NO:41 and SEQ ID NO:42, with SEQ ID NO:43 and SEQ ID NO:44 or with SEQ ID NO:45 and SEQ ID NO:46, wherein SEQ ID NO:41 and SEQ ID NO:42 are a primer pair for amplification of a fifth region of a CACNA1G CpG island, wherein SEQ ID NO:43 and SEQ ID NO:44 are a primer pair for amplification of a sixth region of a CACNA1G CpG island, and wherein SEQ ID NO:45 and SEQ ID NO:46 are a primer pair for amplification of a seventh region of the CACNA1G CpG island, wherein hypermethylation of one or more of the fifth region, the sixth region, or the seventh region of the CACNA1G CpG island is indicative of the presence of the colorectal adenoma, colorectal cancer, gastric cancer, or the AML, thereby detecting the colorectal adenoma, colorectal cancer, gastric cancer, or the AML.

* * * * *

UNITED STATES PATENT AND TRADEMARK OFFICE
CERTIFICATE OF CORRECTION

PATENT NO. : 6,783,933 B1
DATED : August 31, 2004
INVENTOR(S) : Jean-Pierre Issa It is certified that error appears in the above-identified patent and that said Letters Patent is hereby corrected as shown below:

Column 1,
Line 8, please insert the following:
-- This invention was made with Government support under the following grants: Grant No. CA62924, awarded by the National Cancer Institute as a Colon Cancer SPORE Grant No. CA77045, awarded by the National Cancer Institute; and Grant No. 6213-98, awarded by the Leukemia Society of America. The Government has certain rights in this invention. --

Signed and Sealed this

Third Day of May, 2005

JON W. DUDAS
*Director of the United States Patent and Trademark Office*

SEQUENCE LISTING

<160> NUMBER OF SEQ ID NOS: 120

<210> SEQ ID NO 1
<211> LENGTH: 22

```
<212> TYPE: DNA
<213> ORGANISM: Artificial Sequence
<220> FEATURE:
<223> OTHER INFORMATION: Bisulfite-PCR primer

<400> SEQUENCE: 1
gtttttgtag tttgggtttt tt                                          22

<210> SEQ ID NO 2
<211> LENGTH: 18
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: r = G or A

<400> SEQUENCE: 2
rccaacaacr ccaacaac                                               18

<210> SEQ ID NO 3
<211> LENGTH: 20
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: y = C or T

<400> SEQUENCE: 3
ttgtggygtt ggygatagtt                                             20

<210> SEQ ID NO 4
<211> LENGTH: 26
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: r = G or A

<400> SEQUENCE: 4
acraaaaaaa aaaaaaaaaa tctctt                                      26

<210> SEQ ID NO 5
<211> LENGTH: 23
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: y = C or T

<400> SEQUENCE: 5
gggggygttt tttttyggat ttt                                         23

<210> SEQ ID NO 6
<211> LENGTH: 24
<212> TYPE: DNA
<213> ORGANISM: Artificial Sequence
<220> FEATURE:
```

```
<223> OTHER INFORMATION: Bisulfite-PCR primer
<220> FEATURE:
<221> NAME/KEY: misc_feature
<222> LOCATION: (0)...(0)
<223> OTHER INFORMATION: r = G or A

<400> SEQUENCE: 6
ttcccctacr ccctaaaac ttcc                                         24

<210> SEQ ID NO 7
<211> LENGTH: 23
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: y = C or T

<400> SEQUENCE: 7
gtaggttaga gggagggaty gtt                                         23

<210> SEQ ID NO 8
<211> LENGTH: 24
<212> TYPE: DNA
<213> ORGANISM: Artificial Sequence
<220> FEATURE:
<223> OTHER INFORMATION: Bisulfite-PCR primer

<400> SEQUENCE: 8
aaaacaaacc tcaccatact acct                                        24

<210> SEQ ID NO 9
<211> LENGTH: 22
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: y = C or T

<400> SEQUENCE: 9
tttgatttyg tttagtattg at                                          22

<210> SEQ ID NO 10
<211> LENGTH: 19
<212> TYPE: DNA
<213> ORGANISM: Artificial Sequence
<220> FEATURE:
<223> OTHER INFORMATION: Bisulfite-PCR primer

<400> SEQUENCE: 10 cccttaccttt tctttcct                                              19

<210> SEQ ID NO 11
<211> LENGTH: 22
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: y = C or T

<400> SEQUENCE: 11
```

```
tttttttatt gygttaatttg tg                                              22
```

<210> SEQ ID NO 12
<211> LENGTH: 20
<212> TYPE: DNA
<213> ORGANISM: Artificial Sequence
<220> FEATURE:
<223> OTHER INFORMATION: Bisulfite-PCR primer

<400> SEQUENCE: 12

```
tttccccacc tcttcaaata                                                  20
```

<210> SEQ ID NO 13
<211> LENGTH: 21
<212> TYPE: DNA
<213> ORGANISM: Artificial Sequence
<220> FEATURE:
<223> OTHER INFORMATION: Bisulfite-PCR primer

<400> SEQUENCE: 13

```
ggttaggtgg ggtaagagtt t                                                21
```

<210> SEQ ID NO 14
<211> LENGTH: 23
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: r = G or A

<400> SEQUENCE: 14

```
aacrttttaat ccaattacaa acc                                             23
```

<210> SEQ ID NO 15
<211> LENGTH: 25
<212> TYPE: DNA
<213> ORGANISM: Artificial Sequence
<220> FEATURE:
<223> OTHER INFORMATION: Bisulfite-PCR primer

<400> SEQUENCE: 15

```
tttttttagta gttttgagtt agagg                                           25
```

<210> SEQ ID NO 16
<211> LENGTH: 21
<212> TYPE: DNA
<213> ORGANISM: Artificial Sequence
<220> FEATURE:
<223> OTHER INFORMATION: Bisulfite-PCR primer

<400> SEQUENCE: 16

```
tttcatcctt ttacacctcc c                                                21
```

<210> SEQ ID NO 17
<211> LENGTH: 22
<212> TYPE: DNA
<213> ORGANISM: Artificial Sequence
<220> FEATURE:
<223> OTHER INFORMATION: Bisulfite-PCR primer

<400> SEQUENCE: 17

```
tttattttta tttagtgtt ag                                                22
```

```
<210> SEQ ID NO 18
<211> LENGTH: 20
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: r = G or A

<400> SEQUENCE: 18
ctcttcrtat aacatcctac                                               20

<210> SEQ ID NO 19
<211> LENGTH: 21
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: y = C or T

<400> SEQUENCE: 19
gtagtatgtt ygttagygtt t                                             21

<210> SEQ ID NO 20
<211> LENGTH: 20
<212> TYPE: DNA
<213> ORGANISM: Artificial Sequence
<220> FEATURE:
<223> OTHER INFORMATION: Bisulfite-PCR primer

<400> SEQUENCE: 20
aaataccctc aaaaaaaccc                                               20

<210> SEQ ID NO 21
<211> LENGTH: 22
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: y = C or T

<400> SEQUENCE: 21
yggttttttt gaaatttaat tc                                            22

<210> SEQ ID NO 22
<211> LENGTH: 19
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: r = G or A

<400> SEQUENCE: 22
aactccrcat cctcctaaa                                                19

<210> SEQ ID NO 23
<211> LENGTH: 22
```

```
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: y = C or T

<400> SEQUENCE: 23
taagtgttty gttaggtttt tt                                              22

<210> SEQ ID NO 24
<211> LENGTH: 22
<212> TYPE: DNA
<213> ORGANISM: Artificial Sequence
<220> FEATURE:
<223> OTHER INFORMATION: Bisulfite-PCR primer

<400> SEQUENCE: 24
ccaaactcca ctacacaata ac                                              22

<210> SEQ ID NO 25
<211> LENGTH: 20
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: y = C or T

<400> SEQUENCE: 25
gttggtttgt taatyggagt                                                 20

<210> SEQ ID NO 26
<211> LENGTH: 20
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: r = G or A

<400> SEQUENCE: 26
ttaccaaccr aaaccatatt                                                 20

<210> SEQ ID NO 27
<211> LENGTH: 19
<212> TYPE: DNA
<213> ORGANISM: Artificial Sequence
<220> FEATURE:
<223> OTHER INFORMATION: Bisulfite-PCR primer

<400> SEQUENCE: 27
aatgtgtgga atttaggga                                                  19

<210> SEQ ID NO 28
<211> LENGTH: 23
<212> TYPE: DNA
<213> ORGANISM: Artificial Sequence
<220> FEATURE:
<223> OTHER INFORMATION: Bisulfite-PCR primer

<400> SEQUENCE: 28
```
taaaacaacc aactacaact tac                                          23

<210> SEQ ID NO 29
<211> LENGTH: 22
<212> TYPE: DNA
<213> ORGANISM: Artificial Sequence
<220> FEATURE:
<223> OTHER INFORMATION: Bisulfite-PCR primer
<220> FEATURE:
<221> NAME/KEY: misc_feature
<222> LOCATION: (0)...(0)
<223> OTHER INFORMATION: y = C or T

<400> SEQUENCE: 29
agaggaatty ggtagtagag ag                                           22

<210> SEQ ID NO 30
<211> LENGTH: 18
<212> TYPE: DNA
<213> ORGANISM: Artificial Sequence
<220> FEATURE:
<223> OTHER INFORMATION: Bisulfite-PCR primer

<400> SEQUENCE: 30
cacaaccaaa accaaaac                                                18

<210> SEQ ID NO 31
<211> LENGTH: 20
<212> TYPE: DNA
<213> ORGANISM: Artificial Sequence
<220> FEATURE:
<223> OTHER INFORMATION: Bisulfite-PCR primer

<400> SEQUENCE: 31
ggggatttgt ttggtagtgg                                              20

<210> SEQ ID NO 32
<211> LENGTH: 19
<212> TYPE: DNA
<213> ORGANISM: Artificial Sequence
<220> FEATURE:
<223> OTHER INFORMATION: Bisulfite-PCR primer

<400> SEQUENCE: 32
cccgaaattc cccaataaa                                               19

<210> SEQ ID NO 33
<211> LENGTH: 23
<212> TYPE: DNA
<213> ORGANISM: Artificial Sequence
<220> FEATURE:
<223> OTHER INFORMATION: Primer useful for bisulfite/PCR analysis of
      CACNA1G
<220> FEATURE:
<221> NAME/KEY: misc_feature
<222> LOCATION: (0)...(0)
<223> OTHER INFORMATION: y = C or T

<400> SEQUENCE: 33
gayggygtag tagttatttt gtt                                          23

<210> SEQ ID NO 34
<211> LENGTH: 21
<212> TYPE: DNA
<213> ORGANISM: Artificial Sequence
<220> FEATURE:
<223> OTHER INFORMATION: Primer useful for bisulfite/PCR analysis of
      CACNA1G

```
<400> SEQUENCE: 34
catcaccacc cctcacttta c                                              21

<210> SEQ ID NO 35
<211> LENGTH: 25
<212> TYPE: DNA
<213> ORGANISM: Artificial Sequence
<220> FEATURE:
<223> OTHER INFORMATION: Primer useful for bisulfite/PCR analysis of
      CACNA1G
<220> FEATURE:
<221> NAME/KEY: misc_feature
<222> LOCATION: (0)...(0)
<223> OTHER INFORMATION: y = C or T

<400> SEQUENCE: 35
ttygggtatt tatagttttt tggag                                          25

<210> SEQ ID NO 36
<211> LENGTH: 22
<212> TYPE: DNA
<213> ORGANISM: Artificial Sequence
<220> FEATURE:
<223> OTHER INFORMATION: Primer useful for bisulfite/PCR analysis of
      CACNA1G
<220> FEATURE:
<221> NAME/KEY: misc_feature
<222> LOCATION: (0)...(0)
<223> OTHER INFORMATION: r = G or A

<400> SEQUENCE: 36
aatctaccrc cttcactcac tc                                             22

<210> SEQ ID NO 37
<211> LENGTH: 23
<212> TYPE: DNA
<213> ORGANISM: Artificial Sequence
<220> FEATURE:
<223> OTHER INFORMATION: Primer useful for bisulfite/PCR analysis of
      CACNA1G
<220> FEATURE:
<221> NAME/KEY: misc_feature
<222> LOCATION: (0)...(0)
<223> OTHER INFORMATION: y = C or T

<400> SEQUENCE: 37
tttaggagyg ttaatgtgag gtt                                            23

<210> SEQ ID NO 38
<211> LENGTH: 26
<212> TYPE: DNA
<213> ORGANISM: Artificial Sequence
<220> FEATURE:
<223> OTHER INFORMATION: Primer useful for bisulfite/PCR analysis of
      CACNA1G

<400> SEQUENCE: 38
ctaaaaaaac ccaatcttaa aaaaac                                         26

<210> SEQ ID NO 39
<211> LENGTH: 24
<212> TYPE: DNA
<213> ORGANISM: Artificial Sequence
<220> FEATURE:
<223> OTHER INFORMATION: Primer useful for bisulfite/PCR analysis of
      CACNA1G

<400> SEQUENCE: 39
```
tggataaagg atgtttgggg tttg    24

<210> SEQ ID NO 40
<211> LENGTH: 22
<212> TYPE: DNA
<213> ORGANISM: Artificial Sequence
<220> FEATURE:
<223> OTHER INFORMATION: Primer useful for bisulfite/PCR analysis of
      CACNA1G

<400> SEQUENCE: 40
ccctcccctt acccctaaat cc    22

<210> SEQ ID NO 41
<211> LENGTH: 24
<212> TYPE: DNA
<213> ORGANISM: Artificial Sequence
<220> FEATURE:
<223> OTHER INFORMATION: Primer useful for bisulfite/PCR analysis of
      CACNA1G
<220> FEATURE:
<221> NAME/KEY: misc_feature
<222> LOCATION: (0)...(0)
<223> OTHER INFORMATION: y = C or T

<400> SEQUENCE: 41
aatyggattt tagttgtggt tttt    24

<210> SEQ ID NO 42
<211> LENGTH: 24
<212> TYPE: DNA
<213> ORGANISM: Artificial Sequence
<220> FEATURE:
<223> OTHER INFORMATION: Primer useful for bisulfite/PCR analysis of
      CACNA1G

<400> SEQUENCE: 42
cacaccacaa ctaaatccct cact    24

<210> SEQ ID NO 43
<211> LENGTH: 20
<212> TYPE: DNA
<213> ORGANISM: Artificial Sequence
<220> FEATURE:
<223> OTHER INFORMATION: Primer useful for bisulfite/PCR analysis of
      CACNA1G
<220> FEATURE:
<221> NAME/KEY: misc_feature
<222> LOCATION: (0)...(0)
<223> OTHER INFORMATION: y = C or T

<400> SEQUENCE: 43
ttgtggygtt ggygatagtt    20

<210> SEQ ID NO 44
<211> LENGTH: 26
<212> TYPE: DNA
<213> ORGANISM: Artificial Sequence
<220> FEATURE:
<223> OTHER INFORMATION: Primer useful for bisulfite/PCR analysis of
      CACNA1G
<220> FEATURE:
<221> NAME/KEY: misc_feature
<222> LOCATION: (0)...(0)
<223> OTHER INFORMATION: r = G or A

<400> SEQUENCE: 44
acraaaaaaa aaaaaaaaaa tctctt    26

<210> SEQ ID NO 45
<211> LENGTH: 23
<212> TYPE: DNA
<213> ORGANISM: Artificial Sequence
<220> FEATURE:
<223> OTHER INFORMATION: Primer useful for bisulfite/PCR analysis of CACNA1G
<220> FEATURE:
<221> NAME/KEY: misc_feature
<222> LOCATION: (0)...(0)
<223> OTHER INFORMATION: y = C or T

<400> SEQUENCE: 45 ggggggygttt tttttyggat ttt                                      23

<210> SEQ ID NO 46
<211> LENGTH: 24
<212> TYPE: DNA
<213> ORGANISM: Artificial Sequence
<220> FEATURE:
<223> OTHER INFORMATION: Primer useful for bisulfite/PCR analysis of CACNA1G
<220> FEATURE:
<221> NAME/KEY: misc_feature
<222> LOCATION: (0)...(0)
<223> OTHER INFORMATION: r = G or A

<400> SEQUENCE: 46
ttcccctacr ccctaaaac ttcc                                       24

<210> SEQ ID NO 47
<211> LENGTH: 25
<212> TYPE: DNA
<213> ORGANISM: Artificial Sequence
<220> FEATURE:
<223> OTHER INFORMATION: Primer useful for bisulfite/PCR analysis of CACNA1G

<400> SEQUENCE: 47
gggagtttgg gagttgtatt ttgtt                                     25

<210> SEQ ID NO 48
<211> LENGTH: 26
<212> TYPE: DNA
<213> ORGANISM: Artificial Sequence
<220> FEATURE:
<223> OTHER INFORMATION: Primer useful for bisulfite/PCR analysis of CACNA1G

<400> SEQUENCE: 48
aaccaaatta aaaatcaaa ccctaa                                     26

<210> SEQ ID NO 49
<211> LENGTH: 22
<212> TYPE: DNA
<213> ORGANISM: Artificial Sequence
<220> FEATURE:
<223> OTHER INFORMATION: Primer useful for bisulfite/PCR analysis of CACNA1G
<220> FEATURE:
<221> NAME/KEY: misc_feature
<222> LOCATION: (0)...(0)
<223> OTHER INFORMATION: y = C or T

<400> SEQUENCE: 49
gaggggggat ygtaatttt tg                                         22

<210> SEQ ID NO 50
<211> LENGTH: 26
<212> TYPE: DNA
<213> ORGANISM: Artificial Sequence
<220> FEATURE:
<223> OTHER INFORMATION: Primer useful for bisulfite/PCR analysis of CACNA1G
<220> FEATURE:
<221> NAME/KEY: misc_feature
<222> LOCATION: (0)...(0)
<223> OTHER INFORMATION: r = G or A

<400> SEQUENCE: 50

```
ccraaatctc cttattatac ctccaa                                          26
```

<210> SEQ ID NO 51
<211> LENGTH: 3993
<212> TYPE: DNA
<213> ORGANISM: Artificial Sequence
<220> FEATURE:
<223> OTHER INFORMATION: CAGNA1G - a gene encoding a T-type calcium channel
<220> FEATURE:
<221> NAME/KEY: CDS
<222> LOCATION: (373)...(3993)

<400> SEQUENCE: 51

```
cctttcgtt cgccctctcg gggcggcttc gccgaaggta cgccgaatc cggcaaccgg        60 agcctgggcg cgaagcgaag aagccggaac aaagtgaggg ggagccggcc ggctggcccg     120
ggaagcccca ggggcgcagg ggaagcggga ctcgcgccgg gcggggtttc cctgcgcccc     180
ggcgccccgc gggcagcatg ccctgcggg caggggggagc tgggctgaac tggccctccc     240
gggggctcag cttgcgccct agagcccacc agatgtgccc ccgccgggc cccggggttg     300 cgtgaggaca cctcctctga ggggcgccgc ttgccctct ccggatcgcc cggggccccg     360
gctggccaga gg atg gac gag gag gag gat gga gcg ggc gcc gag gag tcg    411
              Met Asp Glu Glu Glu Asp Gly Ala Gly Ala Glu Glu Ser
                1               5                  10 gga cag ccc cgg agc ttc atg cgg ctc aac gac ctg tcg ggg gcc ggg      459
Gly Gln Pro Arg Ser Phe Met Arg Leu Asn Asp Leu Ser Gly Ala Gly
 15                  20                  25 ggc cgg ccg ggg ccg ggg tca gca gaa aag gac ccg ggc agc gcg gac      507
Gly Arg Pro Gly Pro Gly Ser Ala Glu Lys Asp Pro Gly Ser Ala Asp
 30                  35                  40                  45 tcc gag gcg gag ggg ctg ccg tac ccg gcg ctg gcc ccg gtg gtt ttc      555
Ser Glu Ala Glu Gly Leu Pro Tyr Pro Ala Leu Ala Pro Val Val Phe
                 50                  55                  60 ttc tac ttg agc cag gac agc cgc ccg cgg agc tgg tgt ctc cgc acg      603
Phe Tyr Leu Ser Gln Asp Ser Arg Pro Arg Ser Trp Cys Leu Arg Thr
 65                  70                  75 gtc tgt aac ccc tgg ttt gag cgc atc agc atg ttg gtc atc ctt ctc      651
Val Cys Asn Pro Trp Phe Glu Arg Ile Ser Met Leu Val Ile Leu Leu
             80                  85                  90 aac tgc gtg acc ctg ggc atg ttc cgg cca tgc gag gac atc gcc tgt      699
Asn Cys Val Thr Leu Gly Met Phe Arg Pro Cys Glu Asp Ile Ala Cys
 95                 100                 105 gac tcc cag cgc tgc cgg atc ctg cag gcc ttt gat gac ttc atc ttt      747
Asp Ser Gln Arg Cys Arg Ile Leu Gln Ala Phe Asp Asp Phe Ile Phe
110                 115                 120                 125 gcc ttc ttt gcc gtg gag atg gtg gtg aag atg gtg gcc ttg ggc atc      795
Ala Phe Phe Ala Val Glu Met Val Val Lys Met Val Ala Leu Gly Ile
                130                 135                 140 ttt ggg aaa aag tgt tac ctg gga gac act tgg aac cgg ctt gac ttt      843
```

```
                    Phe Gly Lys Lys Cys Tyr Leu Gly Asp Thr Trp Asn Arg Leu Asp Phe
                                    145                 150                 155 ttc atc gtc atc gca ggg atg ctg gag tac tcg ctg gac ctg cag aac             891
Phe Ile Val Ile Ala Gly Met Leu Glu Tyr Ser Leu Asp Leu Gln Asn
                160                 165                 170 gtc agc ttc tca gct gtc agg aca gtc cgt gtg ctc gac ccg ctc agg             939
Val Ser Phe Ser Ala Val Arg Thr Val Arg Val Leu Arg Pro Leu Arg
        175                 180                 185 gcc att aac cgg gtg ccc agc atg cgc atc ctt gtc acg ttg ctg ctg             987
Ala Ile Asn Arg Val Pro Ser Met Arg Ile Leu Val Thr Leu Leu Leu
190                 195                 200                 205 gat acg ctg ccc atg ctg ggc aac gtc ctg ctc tgc ttc ttc gtc                 1035
Asp Thr Leu Pro Met Leu Gly Asn Val Leu Leu Cys Phe Phe Val
                210                 215                 220 ttc ttc atc ttc ggc atc gtc ggc gtc cag ctg tgg gca ggg ctg ctt             1083
Phe Phe Ile Phe Gly Ile Val Gly Val Gln Leu Trp Ala Gly Leu Leu
                225                 230                 235 cgg aac cga tgc ttc cta cct gag aat ttc agc ctc ccc ctg agc gtg             1131
Arg Asn Arg Cys Phe Leu Pro Glu Asn Phe Ser Leu Pro Leu Ser Val
                240                 245                 250 gac ctg gag cgc tat tac cag aca gag aac gag gat gag agc ccc ttc             1179
Asp Leu Glu Arg Tyr Tyr Gln Thr Glu Asn Glu Asp Glu Ser Pro Phe
        255                 260                 265 atc tgc tcc cag cca cgc gag aac ggc atg cgg tcc tgc aga agc gtg             1227
Ile Cys Ser Gln Pro Arg Glu Asn Gly Met Arg Ser Cys Arg Ser Val
270                 275                 280                 285 ccc acg ctg cgc ggg gac ggg ggc ggt ggc cca cct tgc ggt ctg gac             1275
Pro Thr Leu Arg Gly Asp Gly Gly Gly Pro Pro Cys Gly Leu Asp
                290                 295                 300 tat gag gcc tac aac agc tcc agc aac acc acc tgt gtc aac tgg aac             1323
Tyr Glu Ala Tyr Asn Ser Ser Ser Asn Thr Thr Cys Val Asn Trp Asn
                305                 310                 315 cag tac tac acc aac tgc tca gcg ggg gag cac aac ccc ttc aag ggc             1371
Gln Tyr Tyr Thr Asn Cys Ser Ala Gly Glu His Asn Pro Phe Lys Gly
        320                 325                 330 gcc atc aac ttt gac aac att ggc tat gcc tgg atc gcc atc ttc cag             1419
Ala Ile Asn Phe Asp Asn Ile Gly Tyr Ala Trp Ile Ala Ile Phe Gln
335                 340                 345 gtc atc acg ctg gag ggc tgg gtc gac atc atg tac ttt gtg atg gat             1467
Val Ile Thr Leu Glu Gly Trp Val Asp Ile Met Tyr Phe Val Met Asp
350                 355                 360                 365 gct cat tcc ttc tac aat ttc atc tac ttc atc ctc ctc atc atc gtg             1515
Ala His Ser Phe Tyr Asn Phe Ile Tyr Phe Ile Leu Leu Ile Ile Val
                370                 375                 380 ggc tcc ttc ttc atg atc aac ctg tgc ctg gtg gtg att gcc acg cag             1563
Gly Ser Phe Phe Met Ile Asn Leu Cys Leu Val Val Ile Ala Thr Gln
                385                 390                 395 ttc tca gag acc aag cag cgg gaa agc cag ctg atg cgg gag cag cgt             1611
Phe Ser Glu Thr Lys Gln Arg Glu Ser Gln Leu Met Arg Glu Gln Arg
                400                 405                 410 gtg cgg ttc ctg tcc aac gcc agc acc ctg gct agc ttc tct gag ccc             1659
Val Arg Phe Leu Ser Asn Ala Ser Thr Leu Ala Ser Phe Ser Glu Pro
        415                 420                 425 ggc agc tgc tat gag gag ctg ctc aag tac ctg gtg tac atc ctt cgt             1707
Gly Ser Cys Tyr Glu Glu Leu Leu Lys Tyr Leu Val Tyr Ile Leu Arg
430                 435                 440                 445 aag gca gcc cgc agg ctg gct cag gtc tct cgg gca gca ggt gtg cgg             1755
Lys Ala Ala Arg Arg Leu Ala Gln Val Ser Arg Ala Ala Gly Val Arg
                450                 455                 460
```

-continued

| | |
|---|---|
| gtt ggg ctg ctc agc agc cca gca ccc ctc ggg ggc cag gag acc cag<br>Val Gly Leu Leu Ser Ser Pro Ala Pro Leu Gly Gly Gln Glu Thr Gln<br>465                               470                          475 | 1803 |
| ccc agc agc agc tgc tct cgc tcc cac cgc cgc cta tcc gtc cac cac<br>Pro Ser Ser Ser Cys Ser Arg Ser His Arg Arg Leu Ser Val His His<br>       480                          485                         490 | 1851 |
| ctg gtg cac cac cac cac cac cat cac cac cac tac cac ctg ggc aat<br>Leu Val His His His His His His His His His Tyr His Leu Gly Asn<br>495                               500                         505 | 1899 |
| ggg acg ctc agg gcc ccc cgg gcc agc ccg gag atc cag gac agg gat<br>Gly Thr Leu Arg Ala Pro Arg Ala Ser Pro Glu Ile Gln Asp Arg Asp<br>510                          515                         520                        525 | 1947 |
| gcc aat ggg tcc cgc cgg ctc atg ctg cca cca ccc tcg acg cct gcc<br>Ala Asn Gly Ser Arg Arg Leu Met Leu Pro Pro Pro Ser Thr Pro Ala<br>                       530                         535                        540 | 1995 |
| ctc tcc ggg gcc ccc cct ggt ggc gca gag tct gtg cac agc ttc tac<br>Leu Ser Gly Ala Pro Pro Gly Gly Ala Glu Ser Val His Ser Phe Tyr<br>545                               550                         555 | 2043 |
| cat gcc gac tgc cac tta gag cca gtc cgc tgc cag gcg ccc cct ccc<br>His Ala Asp Cys His Leu Glu Pro Val Arg Cys Gln Ala Pro Pro Pro<br>                       560                         565                        570 | 2091 |
| agg tcc cca tct gag gca tcc ggc agg act gtg ggc agc ggg aag gtg<br>Arg Ser Pro Ser Glu Ala Ser Gly Arg Thr Val Gly Ser Gly Lys Val<br>575                               580                         585 | 2139 |
| tat ccc acc gtg cac acc agc cct cca ccg gag acg ctg aag gag aag<br>Tyr Pro Thr Val His Thr Ser Pro Pro Pro Glu Thr Leu Lys Glu Lys<br>590                             595                        600                        605 | 2187 |
| gca cta gta gag gtg gct gcc agc tct ggg ccc cca acc ctc acc agc<br>Ala Leu Val Glu Val Ala Ala Ser Ser Gly Pro Pro Thr Leu Thr Ser<br>                       610                         615                        620 | 2235 |
| ctc aac atc cca ccc ggg ccc tac agc tcc atg cac aag ctg ctg gag<br>Leu Asn Ile Pro Pro Gly Pro Tyr Ser Ser Met His Lys Leu Leu Glu<br>625                               630                         635 | 2283 |
| aca cag agt aca ggt gcc tgc caa agc tct tgc aag atc tcc agc cct<br>Thr Gln Ser Thr Gly Ala Cys Gln Ser Ser Cys Lys Ile Ser Ser Pro<br>                       640                         645                        650 | 2331 |
| tgc ttg aaa gca gac agt gga gcc tgt ggt cca gac agc tgc ccc tac<br>Cys Leu Lys Ala Asp Ser Gly Ala Cys Gly Pro Asp Ser Cys Pro Tyr<br>655                               660                        665 | 2379 |
| tgt gcc cgg gcc ggg gca ggg gag gtg gag ctc gcc gac cgt gaa atg<br>Cys Ala Arg Ala Gly Ala Gly Glu Val Glu Leu Ala Asp Arg Glu Met<br>670                          675                         680                        685 | 2427 |
| cct gac tca gac agc gag gca gtt tat gag ttc aca cag gat gcc cag<br>Pro Asp Ser Asp Ser Glu Ala Val Tyr Glu Phe Thr Gln Asp Ala Gln<br>                       690                         695                        700 | 2475 |
| cac agc gac ctc cgg gac ccc cac agc cgg cgg caa cgg agc ctg ggc<br>His Ser Asp Leu Arg Asp Pro His Ser Arg Arg Gln Arg Ser Leu Gly<br>705                               710                         715 | 2523 |
| cca gat gca gag ccc agc tct gtg ctg gcc ttc tgg agg cta atc tgt<br>Pro Asp Ala Glu Pro Ser Ser Val Leu Ala Phe Trp Arg Leu Ile Cys<br>                       720                         725                        730 | 2571 |
| gac acc ttc cga aag att gtg gac agc aag tac ttt ggc cgg gga atc<br>Asp Thr Phe Arg Lys Ile Val Asp Ser Lys Tyr Phe Gly Arg Gly Ile<br>735                               740                         745 | 2619 |
| atg atc gcc atc ctg gtc aac aca ctc agc atg ggc atc gaa tac cac<br>Met Ile Ala Ile Leu Val Asn Thr Leu Ser Met Gly Ile Glu Tyr His<br>750                               755                        760                        765 | 2667 |
| gag cag ccc gag gag ctt acc aac gcc cta gaa atc agc aac atc gtc<br>Glu Gln Pro Glu Glu Leu Thr Asn Ala Leu Glu Ile Ser Asn Ile Val<br>                       770                         775                        780 | 2715 |

-continued

| | |
|---|---|
| ttc acc agc ctc ttt gcc ctg gag atg ctg ctg aag ctg ctt gtg tat<br>Phe Thr Ser Leu Phe Ala Leu Glu Met Leu Leu Lys Leu Leu Val Tyr<br>              785                    790                  795 | 2763 |
| ggt ccc ttt ggc tac atc aag aat ccc tac aac atc ttc gat ggt gtc<br>Gly Pro Phe Gly Tyr Ile Lys Asn Pro Tyr Asn Ile Phe Asp Gly Val<br>        800                    805                    810 | 2811 |
| att gtg gtc atc agc gtg tgg gag atc gtg ggc cag cag ggg ggc ggc<br>Ile Val Val Ile Ser Val Trp Glu Ile Val Gly Gln Gln Gly Gly Gly<br>815                    820                    825 | 2859 |
| ctg tcg gtg ctg cgg acc ttc cgc ctg atg cgt gtg ctg aag ctg gtg<br>Leu Ser Val Leu Arg Thr Phe Arg Leu Met Arg Val Leu Lys Leu Val<br>830                    835                    840                    845 | 2907 |
| cgc ttc ctg ccg gcg ctg cag cgg cag ctg gtg gtg ctc atg aag acc<br>Arg Phe Leu Pro Ala Leu Gln Arg Gln Leu Val Val Leu Met Lys Thr<br>                  850                    855                    860 | 2955 |
| atg gac aac gtg gcc acc ttc tgc atg ctg ctt atg ctc ttc atc ttc<br>Met Asp Asn Val Ala Thr Phe Cys Met Leu Leu Met Leu Phe Ile Phe<br>                    865                    870                    875 | 3003 |
| atc ttc agc atc ctg ggc atg cat ctc ttc ggc tgc aag ttt gcc tct<br>Ile Phe Ser Ile Leu Gly Met His Leu Phe Gly Cys Lys Phe Ala Ser<br>880                    885                    890 | 3051 |
| gag cgg gat ggg gac acc ctg cca gac cgg aag aat ttt gac tcc ttg<br>Glu Arg Asp Gly Asp Thr Leu Pro Asp Arg Lys Asn Phe Asp Ser Leu<br>895                    900                    905 | 3099 |
| ctc tgg gcc atc gtc act gtc ttt cag atc ctg acc cag gag gac tgg<br>Leu Trp Ala Ile Val Thr Val Phe Gln Ile Leu Thr Gln Glu Asp Trp<br>910                  915                    920                    925 | 3147 |
| aac aaa gtc ctc tac aat ggt atg gcc tcc acg tcg tcc tgg gcg gcc<br>Asn Lys Val Leu Tyr Asn Gly Met Ala Ser Thr Ser Ser Trp Ala Ala<br>                  930                    935                    940 | 3195 |
| ctt tat ttc att gcc ctc atg acc ttc ggc aac tac gtg ctc ttc aat<br>Leu Tyr Phe Ile Ala Leu Met Thr Phe Gly Asn Tyr Val Leu Phe Asn<br>                    945                    950                    955 | 3243 |
| ttg ctg gtc gcc att ctg gtg gag ggc ttc cag gcg gag gga gat gcc<br>Leu Leu Val Ala Ile Leu Val Glu Gly Phe Gln Ala Glu Gly Asp Ala<br>960                    965                    970 | 3291 |
| aac aag tcc gaa tca gag ccc gat ttc ttc tca ccc agc ctg gat ggt<br>Asn Lys Ser Glu Ser Glu Pro Asp Phe Phe Ser Pro Ser Leu Asp Gly<br>975                    980                    985 | 3339 |
| gat ggg gac agg aag aag tgc ttg gcc ttg gtg tcc ctg gga gag cac<br>Asp Gly Asp Arg Lys Lys Cys Leu Ala Leu Val Ser Leu Gly Glu His<br>990                  995                   1000               1005 | 3387 |
| ccg gag ctg cgg aag agc ctg ctg ccg cct ctc atc atc cac acg gcc<br>Pro Glu Leu Arg Lys Ser Leu Leu Pro Pro Leu Ile Ile His Thr Ala<br>                  1010                    1015                   1020 | 3435 |
| gcc aca ccc atg tcg ctg ccc aag agc acc agc acg ggc ctg ggc gag<br>Ala Thr Pro Met Ser Leu Pro Lys Ser Thr Ser Thr Gly Leu Gly Glu<br>                    1025                    1030                   1035 | 3483 |
| gcg ctg ggc cct gcg tcg cgc cgc acc agc agc agc ggg tcg gca gag<br>Ala Leu Gly Pro Ala Ser Arg Arg Thr Ser Ser Ser Gly Ser Ala Glu<br>1040                    1045                    1050 | 3531 |
| cct ggg gcg gcc cac gag atg aag tca ccg ccc agc gcc cgc agc tct<br>Pro Gly Ala Ala His Glu Met Lys Ser Pro Pro Ser Ala Arg Ser Ser<br>1055                    1060                    1065 | 3579 |
| ccg cac agc ccc tgg agc gct gca agc agc tgg acc agc agg cgc tcc<br>Pro His Ser Pro Trp Ser Ala Ala Ser Ser Trp Thr Ser Arg Arg Ser<br>1070                    1075                    1080                   1085 | 3627 |
| agc cgg aac agc ctc ggc cgt gca ccc agc ctg aag cgg aga agc cca<br>Ser Arg Asn Ser Leu Gly Arg Ala Pro Ser Leu Lys Arg Arg Ser Pro | 3675 |

```
                1090                1095                1100
agt gga gag cgg cgg tcc ctg ttg tcg gga gaa ggc cag gag agc cag    3723
Ser Gly Glu Arg Arg Ser Leu Leu Ser Gly Glu Gly Gln Glu Ser Gln
            1105                1110                1115 gat gaa gag gag agc tca gaa gag gag cgg gcc agc cct gcg ggc agt    3771
Asp Glu Glu Glu Ser Ser Glu Glu Glu Arg Ala Ser Pro Ala Gly Ser
        1120                1125                1130 gac cat cgc cac agg ggg tcc ctg gag cgg gag gcc aag agt tcc ttt    3819
Asp His Arg His Arg Gly Ser Leu Glu Arg Glu Ala Lys Ser Ser Phe
    1135                1140                1145 gac ctg cca gac aca ctg cag gtg cca ggg ctg cat cgc act gcc agt    3867
Asp Leu Pro Asp Thr Leu Gln Val Pro Gly Leu His Arg Thr Ala Ser
1150                1155                1160                1165 ggc cga ggg tct gct tct gag cac cag gac tgc aat ggc aag tcg gct    3915
Gly Arg Gly Ser Ala Ser Glu His Gln Asp Cys Asn Gly Lys Ser Ala
                1170                1175                1180 tca ggg cgc ctg gcc cgg gcc ctg cgg cct gat gac ccc cca ctg gat    3963
Ser Gly Arg Leu Ala Arg Ala Leu Arg Pro Asp Asp Pro Pro Leu Asp
            1185                1190                1195 ggg gat gac gcc gat gac gag ggc aac ctg                            3993
Gly Asp Asp Ala Asp Asp Glu Gly Asn Leu
        1200                1205
```

<210> SEQ ID NO 52
<211> LENGTH: 1207
<212> TYPE: PRT
<213> ORGANISM: Artificial Sequence
<220> FEATURE:
<223> OTHER INFORMATION: CACNA1G - a gene ecoding a T-type calcium
      channel

<400> SEQUENCE: 52

```
Met Asp Glu Glu Asp Gly Ala Gly Ala Glu Glu Ser Gly Gln Pro
 1               5                  10                  15

Arg Ser Phe Met Arg Leu Asn Asp Leu Ser Gly Ala Gly Gly Arg Pro
                20                  25                  30

Gly Pro Gly Ser Ala Glu Lys Asp Pro Gly Ser Ala Asp Ser Glu Ala
            35                  40                  45

Glu Gly Leu Pro Tyr Pro Ala Leu Ala Pro Val Val Phe Phe Tyr Leu
        50                  55                  60

Ser Gln Asp Ser Arg Pro Arg Ser Trp Cys Leu Arg Thr Val Cys Asn
65                  70                  75                  80

Pro Trp Phe Glu Arg Ile Ser Met Leu Val Ile Leu Leu Asn Cys Val
                85                  90                  95

Thr Leu Gly Met Phe Arg Pro Cys Glu Asp Ile Ala Cys Asp Ser Gln
            100                 105                 110

Arg Cys Arg Ile Leu Gln Ala Phe Asp Asp Phe Ile Phe Ala Phe Phe
        115                 120                 125

Ala Val Glu Met Val Val Lys Met Val Ala Leu Gly Ile Phe Gly Lys
    130                 135                 140

Lys Cys Tyr Leu Gly Asp Thr Trp Asn Arg Leu Asp Phe Phe Ile Val
145                 150                 155                 160

Ile Ala Gly Met Leu Glu Tyr Ser Leu Asp Leu Gln Asn Val Ser Phe
                165                 170                 175

Ser Ala Val Arg Thr Val Arg Val Leu Arg Pro Leu Arg Ala Ile Asn
            180                 185                 190

Arg Val Pro Ser Met Arg Ile Leu Val Thr Leu Leu Leu Asp Thr Leu
        195                 200                 205
```

```
Pro Met Leu Gly Asn Val Leu Leu Cys Phe Phe Val Phe Phe Ile
    210                 215                 220
Phe Gly Ile Val Gly Val Gln Leu Trp Ala Gly Leu Leu Arg Asn Arg
225                 230                 235                 240
Cys Phe Leu Pro Glu Asn Phe Ser Leu Pro Leu Ser Val Asp Leu Glu
                245                 250                 255
Arg Tyr Tyr Gln Thr Glu Asn Glu Asp Glu Ser Pro Phe Ile Cys Ser
            260                 265                 270
Gln Pro Arg Glu Asn Gly Met Arg Ser Cys Arg Ser Val Pro Thr Leu
        275                 280                 285
Arg Gly Asp Gly Gly Gly Pro Pro Cys Gly Leu Asp Tyr Glu Ala
290                 295                 300
Tyr Asn Ser Ser Ser Asn Thr Thr Cys Val Asn Trp Asn Gln Tyr Tyr
305                 310                 315                 320
Thr Asn Cys Ser Ala Gly Glu His Asn Pro Phe Lys Gly Ala Ile Asn
                325                 330                 335
Phe Asp Asn Ile Gly Tyr Ala Trp Ile Ala Ile Phe Gln Val Ile Thr
            340                 345                 350
Leu Glu Gly Trp Val Asp Ile Met Tyr Phe Val Met Asp Ala His Ser
        355                 360                 365
Phe Tyr Asn Phe Ile Tyr Phe Ile Leu Leu Ile Ile Val Gly Ser Phe
370                 375                 380
Phe Met Ile Asn Leu Cys Leu Val Val Ile Ala Thr Gln Phe Ser Glu
385                 390                 395                 400
Thr Lys Gln Arg Glu Ser Gln Leu Met Arg Glu Gln Arg Val Arg Phe
                405                 410                 415
Leu Ser Asn Ala Ser Thr Leu Ala Ser Phe Ser Glu Pro Gly Ser Cys
            420                 425                 430
Tyr Glu Glu Leu Leu Lys Tyr Leu Val Tyr Ile Leu Arg Lys Ala Ala
        435                 440                 445
Arg Arg Leu Ala Gln Val Ser Arg Ala Ala Gly Val Arg Val Gly Leu
450                 455                 460
Leu Ser Ser Pro Ala Pro Leu Gly Gly Gln Glu Thr Gln Pro Ser Ser
465                 470                 475                 480
Ser Cys Ser Arg Ser His Arg Arg Leu Ser Val His His Leu Val His
                485                 490                 495
His His His His His His His Tyr His Leu Gly Asn Gly Thr Leu
            500                 505                 510
Arg Ala Pro Arg Ala Ser Pro Glu Ile Gln Asp Arg Asp Ala Asn Gly
        515                 520                 525
Ser Arg Arg Leu Met Leu Pro Pro Ser Thr Pro Ala Leu Ser Gly
530                 535                 540
Ala Pro Pro Gly Gly Ala Glu Ser Val His Ser Phe Tyr His Ala Asp
545                 550                 555                 560
Cys His Leu Glu Pro Val Arg Cys Gln Ala Pro Pro Arg Ser Pro
                565                 570                 575
Ser Glu Ala Ser Gly Arg Thr Val Gly Ser Gly Lys Val Tyr Pro Thr
            580                 585                 590
Val His Thr Ser Pro Pro Pro Glu Thr Leu Lys Glu Lys Ala Leu Val
        595                 600                 605
Glu Val Ala Ala Ser Ser Gly Pro Pro Thr Leu Thr Ser Leu Asn Ile
610                 615                 620
```

```
Pro Pro Gly Pro Tyr Ser Ser Met His Lys Leu Leu Glu Thr Gln Ser
625                 630                 635                 640

Thr Gly Ala Cys Gln Ser Ser Cys Lys Ile Ser Ser Pro Cys Leu Lys
            645                 650                 655

Ala Asp Ser Gly Ala Cys Gly Pro Asp Ser Cys Pro Tyr Cys Ala Arg
                660                 665                 670

Ala Gly Ala Gly Glu Val Glu Leu Ala Asp Arg Glu Met Pro Asp Ser
            675                 680                 685

Asp Ser Glu Ala Val Tyr Glu Phe Thr Gln Asp Ala Gln His Ser Asp
690                 695                 700

Leu Arg Asp Pro His Ser Arg Arg Gln Arg Ser Leu Gly Pro Asp Ala
705                 710                 715                 720

Glu Pro Ser Ser Val Leu Ala Phe Trp Arg Leu Ile Cys Asp Thr Phe
                725                 730                 735

Arg Lys Ile Val Asp Ser Lys Tyr Phe Gly Arg Gly Ile Met Ile Ala
            740                 745                 750

Ile Leu Val Asn Thr Leu Ser Met Gly Ile Glu Tyr His Glu Gln Pro
            755                 760                 765

Glu Glu Leu Thr Asn Ala Leu Glu Ile Ser Asn Ile Val Phe Thr Ser
770                 775                 780

Leu Phe Ala Leu Glu Met Leu Leu Lys Leu Leu Val Tyr Gly Pro Phe
785                 790                 795                 800

Gly Tyr Ile Lys Asn Pro Tyr Asn Ile Phe Asp Gly Val Ile Val Val
                805                 810                 815

Ile Ser Val Trp Glu Ile Val Gly Gln Gln Gly Gly Leu Ser Val
            820                 825                 830

Leu Arg Thr Phe Arg Leu Met Arg Val Leu Lys Leu Val Arg Phe Leu
            835                 840                 845

Pro Ala Leu Gln Arg Gln Leu Val Val Leu Met Lys Thr Met Asp Asn
850                 855                 860

Val Ala Thr Phe Cys Met Leu Leu Met Leu Phe Ile Phe Ile Phe Ser
865                 870                 875                 880

Ile Leu Gly Met His Leu Phe Gly Cys Lys Phe Ala Ser Glu Arg Asp
                885                 890                 895

Gly Asp Thr Leu Pro Asp Arg Lys Asn Phe Asp Ser Leu Leu Trp Ala
            900                 905                 910

Ile Val Thr Val Phe Gln Ile Leu Thr Gln Glu Asp Trp Asn Lys Val
            915                 920                 925

Leu Tyr Asn Gly Met Ala Ser Thr Ser Ser Trp Ala Ala Leu Tyr Phe
930                 935                 940

Ile Ala Leu Met Thr Phe Gly Asn Tyr Val Leu Phe Asn Leu Leu Val
945                 950                 955                 960

Ala Ile Leu Val Glu Gly Phe Gln Ala Glu Gly Asp Ala Asn Lys Ser
                965                 970                 975

Glu Ser Glu Pro Asp Phe Phe Ser Pro Ser Leu Asp Gly Asp Gly Asp
                980                 985                 990

Arg Lys Lys Cys Leu Ala Leu Val Ser Leu Gly Glu His Pro Glu Leu
            995                 1000                1005

Arg Lys Ser Leu Leu Pro Pro Leu Ile Ile His Thr Ala Ala Thr Pro
    1010                1015                1020

Met Ser Leu Pro Lys Ser Thr Ser Thr Gly Leu Gly Glu Ala Leu Gly
1025                1030                1035                1040

Pro Ala Ser Arg Arg Thr Ser Ser Ser Gly Ser Ala Glu Pro Gly Ala
```

-continued

```
                         1045                1050                1055
Ala His Glu Met Lys Ser Pro Pro Ser Ala Arg Ser Ser Pro His Ser
            1060                1065                1070
Pro Trp Ser Ala Ala Ser Ser Trp Thr Ser Arg Arg Ser Ser Arg Asn
        1075                1080                1085
Ser Leu Gly Arg Ala Pro Ser Leu Lys Arg Arg Ser Pro Ser Gly Glu
    1090                1095                1100
Arg Arg Ser Leu Leu Ser Gly Glu Gly Gln Glu Ser Gln Asp Glu Glu
1105                1110                1115                1120
Glu Ser Ser Glu Glu Arg Ala Ser Pro Ala Gly Ser Asp His Arg
            1125                1130                1135
His Arg Gly Ser Leu Glu Arg Glu Ala Lys Ser Ser Phe Asp Leu Pro
        1140                1145                1150
Asp Thr Leu Gln Val Pro Gly Leu His Arg Thr Ala Ser Gly Arg Gly
        1155                1160                1165
Ser Ala Ser Glu His Gln Asp Cys Asn Gly Lys Ser Ala Ser Gly Arg
    1170                1175                1180
Leu Ala Arg Ala Leu Arg Pro Asp Asp Pro Pro Leu Asp Gly Asp Asp
1185                1190                1195                1200
Ala Asp Asp Glu Gly Asn Leu
            1205
```

<210> SEQ ID NO 53
<211> LENGTH: 23
<212> TYPE: DNA
<213> ORGANISM: Artificial Sequence
<220> FEATURE:
<223> OTHER INFORMATION: primer for PCR (GAPDH)

<400> SEQUENCE: 53
cggagtcaac ggattggtcg tat                                          23

<210> SEQ ID NO 54
<211> LENGTH: 24
<212> TYPE: DNA
<213> ORGANISM: Artificial Sequence
<220> FEATURE:
<223> OTHER INFORMATION: primer for PCR (GAPDH)

<400> SEQUENCE: 54
agccttctcc atggtggtga agac                                         24

<210> SEQ ID NO 55
<211> LENGTH: 22
<212> TYPE: DNA
<213> ORGANISM: Artificial Sequence
<220> FEATURE:
<223> OTHER INFORMATION: Target sequence for bisulfite-PCR primer

<400> SEQUENCE: 55
aaaaaaccca aactacaaaa ac                                           22

<210> SEQ ID NO 56
<211> LENGTH: 18
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: r = G or A -continued

```
<400> SEQUENCE: 56
gttgttggrg ttgttggr                                                   18

<210> SEQ ID NO 57
<211> LENGTH: 20
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: y = C or T

<400> SEQUENCE: 57
aactatcycc aacyccacaa                                                 20

<210> SEQ ID NO 58
<211> LENGTH: 26
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: r = G or A

<400> SEQUENCE: 58
aagagatttt ttttttttt tttrgt                                           26

<210> SEQ ID NO 59
<211> LENGTH: 23
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: y = C or T

<400> SEQUENCE: 59
aaaatccyaa aaaaaacycc ccc                                             23

<210> SEQ ID NO 60
<211> LENGTH: 24
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: r = G or A

<400> SEQUENCE: 60
ggaagtttta ggggrgtagg ggaa                                            24

<210> SEQ ID NO 61
<211> LENGTH: 23
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
```

```
<223> OTHER INFORMATION: y = C or T

<400> SEQUENCE: 61
aacyatccct ccctctaacc tac                                      23

<210> SEQ ID NO 62
<211> LENGTH: 24
<212> TYPE: DNA
<213> ORGANISM: Artificial Sequence
<220> FEATURE:
<223> OTHER INFORMATION: Target sequence for bisulfite-PCR primer

<400> SEQUENCE: 62
aggtagtatg gtgaggtttg tttt                                     24

<210> SEQ ID NO 63
<211> LENGTH: 22
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: r = G or A

<400> SEQUENCE: 63
atcaatacta aacraaatca aa                                       22

<210> SEQ ID NO 64
<211> LENGTH: 19
<212> TYPE: DNA
<213> ORGANISM: Artificial Sequence
<220> FEATURE:
<223> OTHER INFORMATION: Target sequence for bisulfite-PCR primer

<400> SEQUENCE: 64
aggaaaagaa aggtaaggg                                           19

<210> SEQ ID NO 65
<211> LENGTH: 22
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: r = G or A

<400> SEQUENCE: 65
caaaattaac rcaataaaaa aa                                       22

<210> SEQ ID NO 66
<211> LENGTH: 20
<212> TYPE: DNA
<213> ORGANISM: Artificial Sequence
<220> FEATURE:
<223> OTHER INFORMATION: Target sequence for bisulfite-PCR primer

<400> SEQUENCE: 66
tatttgaaga ggtgggggaaa                                         20

<210> SEQ ID NO 67
<211> LENGTH: 21
<212> TYPE: DNA
<213> ORGANISM: Artificial Sequence
```

```
<220> FEATURE:
<223> OTHER INFORMATION: Target sequence for bisulfite-PCR primer

<400> SEQUENCE: 67
aaactcttac cccacctaac c                                                   21

<210> SEQ ID NO 68
<211> LENGTH: 23
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: y = C or T

<400> SEQUENCE: 68
ggtttgtaat tggattaaay gtt                                                 23

<210> SEQ ID NO 69
<211> LENGTH: 22
<212> TYPE: DNA
<213> ORGANISM: Artificial Sequence
<220> FEATURE:
<223> OTHER INFORMATION: Target sequence for bisulfite-PCR primer

<400> SEQUENCE: 69
ccactaactc aaaactaaaa aa                                                  22

<210> SEQ ID NO 70
<211> LENGTH: 21
<212> TYPE: DNA
<213> ORGANISM: Artificial Sequence
<220> FEATURE:
<223> OTHER INFORMATION: Target sequence for bisulfite-PCR primer

<400> SEQUENCE: 70
gggaggtgta aaaggatgaa a                                                   21

<210> SEQ ID NO 71
<211> LENGTH: 22
<212> TYPE: DNA
<213> ORGANISM: Artificial Sequence
<220> FEATURE:
<223> OTHER INFORMATION: Target sequence for bisulfite-PCR primer

<400> SEQUENCE: 71
ctaacactaa aataaaaata aa                                                  22

<210> SEQ ID NO 72
<211> LENGTH: 20
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: y = C or T

<400> SEQUENCE: 72
gtaggatgtt ataygaagag                                                     20

<210> SEQ ID NO 73
<211> LENGTH: 21
<212> TYPE: DNA
```

```
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: r = G or A

<400> SEQUENCE: 73
aaacrctaac raacatacta c                                              21

<210> SEQ ID NO 74
<211> LENGTH: 20
<212> TYPE: DNA
<213> ORGANISM: Artificial Sequence
<220> FEATURE:
<223> OTHER INFORMATION: Target sequence for bisulfite-PCR primer

<400> SEQUENCE: 74
gggttttttt tagggtattt                                                20

<210> SEQ ID NO 75
<211> LENGTH: 22
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: r = G or A

<400> SEQUENCE: 75
gaattaaatt tcaaaaaaac cr                                             22

<210> SEQ ID NO 76
<211> LENGTH: 19
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: y = C or T

<400> SEQUENCE: 76
tttaggagga tgyggagtt                                                 19

<210> SEQ ID NO 77
<211> LENGTH: 22
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: r = G or A

<400> SEQUENCE: 77
aaaaaaccta acraaacact ta                                             22

<210> SEQ ID NO 78
<211> LENGTH: 22
<212> TYPE: DNA
<213> ORGANISM: Artificial Sequence
<220> FEATURE:
<223> OTHER INFORMATION: Target sequence for bisulfite-PCR primer
```

```
<400> SEQUENCE: 78
gttattgtgt agtggagttt gg                                          22

<210> SEQ ID NO 79
<211> LENGTH: 20
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: r = G or A

<400> SEQUENCE: 79
actccratta acaaaccaac                                             20

<210> SEQ ID NO 80
<211> LENGTH: 20
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: y = C or T

<400> SEQUENCE: 80
aatatggttt yggttggtaa                                             20

<210> SEQ ID NO 81
<211> LENGTH: 19
<212> TYPE: DNA
<213> ORGANISM: Artificial Sequence
<220> FEATURE:
<223> OTHER INFORMATION: Target sequence for bisulfite-PCR primer

<400> SEQUENCE: 81
tccctaaatt ccacacatt                                              19

<210> SEQ ID NO 82
<211> LENGTH: 23
<212> TYPE: DNA
<213> ORGANISM: Artificial Sequence
<220> FEATURE:
<223> OTHER INFORMATION: Target sequence for bisulfite-PCR primer

<400> SEQUENCE: 82
gtaagttgta gttggttgtt tta                                         23

<210> SEQ ID NO 83
<211> LENGTH: 22
<212> TYPE: DNA
<213> ORGANISM: Artificial Sequence
<220> FEATURE:
<223> OTHER INFORMATION: Target sequence for bisulfite-PCR primer
<220> FEATURE:
<221> NAME/KEY: misc_feature
<222> LOCATION: (0)...(0)
<223> OTHER INFORMATION: r = G or A

<400> SEQUENCE: 83
ctctctacta ccraattcct ct                                          22

<210> SEQ ID NO 84
```

```
<211> LENGTH: 18
<212> TYPE: DNA
<213> ORGANISM: Artificial Sequence
<220> FEATURE:
<223> OTHER INFORMATION: Target sequence for bisulfite-PCR primer

<400> SEQUENCE: 84
gttttggttt tggttgtg                                                 18

<210> SEQ ID NO 85
<211> LENGTH: 20
<212> TYPE: DNA
<213> ORGANISM: Artificial Sequence
<220> FEATURE:
<223> OTHER INFORMATION: Target sequence for bisulfite-PCR primer

<400> SEQUENCE: 85
ccactaccaa acaaatcccc                                               20

<210> SEQ ID NO 86
<211> LENGTH: 19
<212> TYPE: DNA
<213> ORGANISM: Artificial Sequence
<220> FEATURE:
<223> OTHER INFORMATION: Target sequence for bisulfite-PCR primer

<400> SEQUENCE: 86
tttattgggg aatttcggg                                                19

<210> SEQ ID NO 87
<211> LENGTH: 23
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (0)...(0)
<223> OTHER INFORMATION: r = G or A

<400> SEQUENCE: 87
aacaaaataa ctactacrcc rtc                                           23

<210> SEQ ID NO 88
<211> LENGTH: 21
<212> TYPE: DNA
<213> ORGANISM: Artificial Sequence
<220> FEATURE:
<223> OTHER INFORMATION: Target sequence

<400> SEQUENCE: 88
gtaaagtgag gggtggtgat g                                             21

<210> SEQ ID NO 89
<211> LENGTH: 25
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (0)...(0)
<223> OTHER INFORMATION: r = G or A

<400> SEQUENCE: 89
ctccaaaaaa ctataaatac ccraa                                         25
```

```
<210> SEQ ID NO 90
<211> LENGTH: 22
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (0)...(0)
<223> OTHER INFORMATION: y = C or T

<400> SEQUENCE: 90
gagtgagtga aggyggtaga tt                                              22

<210> SEQ ID NO 91
<211> LENGTH: 23
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (0)...(0)
<223> OTHER INFORMATION: r = G or A

<400> SEQUENCE: 91
aacctcacat taacrctcct aaa                                             23

<210> SEQ ID NO 92
<211> LENGTH: 26
<212> TYPE: DNA
<213> ORGANISM: Artificial Sequence
<220> FEATURE:
<223> OTHER INFORMATION: Target sequence

<400> SEQUENCE: 92 gttttttaa gattgggttt ttttag                                           26

<210> SEQ ID NO 93
<211> LENGTH: 24
<212> TYPE: DNA
<213> ORGANISM: Artificial Sequence
<220> FEATURE:
<223> OTHER INFORMATION: Target sequence

<400> SEQUENCE: 93
caaaccccaa acatcctta tcca                                             24

<210> SEQ ID NO 94
<211> LENGTH: 22
<212> TYPE: DNA
<213> ORGANISM: Artificial Sequence
<220> FEATURE:
<223> OTHER INFORMATION: Target sequence

<400> SEQUENCE: 94
ggatttaggg gtaagggag gg                                               22

<210> SEQ ID NO 95
<211> LENGTH: 24
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (0)...(0)
<223> OTHER INFORMATION: r = G or A
```

```
<400> SEQUENCE: 95
aaaaaccaca actaaaatcc ratt                                          24

<210> SEQ ID NO 96
<211> LENGTH: 24
<212> TYPE: DNA
<213> ORGANISM: Artificial Sequence
<220> FEATURE:
<223> OTHER INFORMATION: Target sequence

<400> SEQUENCE: 96
agtgagggat ttagttgtgg tgtg                                          24

<210> SEQ ID NO 97
<211> LENGTH: 20
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (0)...(0)
<223> OTHER INFORMATION: r = G or A

<400> SEQUENCE: 97
aactatcrcc aacrccacaa                                               20

<210> SEQ ID NO 98
<211> LENGTH: 26
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (0)...(0)
<223> OTHER INFORMATION: y = C or T

<400> SEQUENCE: 98
aagagatttt tttttttttt tttygt                                        26

<210> SEQ ID NO 99
<211> LENGTH: 23
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (0)...(0)
<223> OTHER INFORMATION: r = G or A

<400> SEQUENCE: 99
aaaatccraa aaaaaacrcc ccc                                           23

<210> SEQ ID NO 100
<211> LENGTH: 24
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (0)...(0)
<223> OTHER INFORMATION: y = C or T

<400> SEQUENCE: 100
ggaagtttta ggggygtagg ggaa                                          24
```

-continued

<210> SEQ ID NO 101
<211> LENGTH: 25
<212> TYPE: DNA
<213> ORGANISM: Artificial Sequence
<220> FEATURE:
<223> OTHER INFORMATION: Target sequence

<400> SEQUENCE: 101
aacaaaatac aactcccaaa caccc                                       25

<210> SEQ ID NO 102
<211> LENGTH: 26
<212> TYPE: DNA
<213> ORGANISM: Artificial Sequence
<220> FEATURE:
<223> OTHER INFORMATION: Target sequence

<400> SEQUENCE: 102
ttagggtttg atttttaat ttggtt                                       26

<210> SEQ ID NO 103
<211> LENGTH: 22
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (0)...(0)
<223> OTHER INFORMATION: r = G or A

<400> SEQUENCE: 103
caaaaaatta cratccccc tc                                           22

<210> SEQ ID NO 104
<211> LENGTH: 26
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (0)...(0)
<223> OTHER INFORMATION: y = C or T

<400> SEQUENCE: 104
ttggaggtat aataaggaga tttygg                                      26

<210> SEQ ID NO 105
<211> LENGTH: 576
<212> TYPE: DNA
<213> ORGANISM: Homo sapiens
<220> FEATURE:
<221> NAME/KEY: gene
<222> LOCATION: (0)...(0)
<223> OTHER INFORMATION: APOB CpG ISLAND

<400> SEQUENCE: 105
cccgggaggc gcccttggga cctttttgcaa tcctggcgct cttgcagcct gggcttccta    60
taaatggggt gcgggcgccg gccgcgcatt cccaccggga cctgcggggc tgagtgccct   120
tctcggttgc tgccgctgag gagcccgccc agccagccag ggccgcgagg ccgaggccag   180
gccgcagccc aggagccgcc ccaccgcagc tggcgatgga cccgccgagg cccgcgctgc   240
tggcgctgcc tgcgctgctg ctgctgctgc tggcgggcgc cagggccggt gagtgcgcgg   300

-continued

| | | | | |
|---|---|---|---|---|
| ccgctctgcg | ggcagcagag | ggagcgggag | ggagccggcg | gaccgaggtt ggccggggca | 360 |
| gcctgggcct | aggccagagg | gagggcagcc | acagggtcca | ggcgagtgg ggggattgga | 420 |
| ccagctggcg | gcccctgcag | gctcaggatg | ggggcgcgg | gatggagggg ctgaggaggg | 480 |
| ggtctccgga | gcctgcctcc | ctcctgaaag | gtgaaacctg | tgccggtggt cccctgtcg | 540 |
| ggccctagc | acccgctggg | aagacgtggg | aagctc | | 576 |

<210> SEQ ID NO 106
<211> LENGTH: 2093
<212> TYPE: DNA
<213> ORGANISM: Homo sapiens
<220> FEATURE:
<221> NAME/KEY: gene
<222> LOCATION: (0)...(0)
<223> OTHER INFORMATION: CACNA1G CpG ISLAND

<400> SEQUENCE: 106

| | | | | |
|---|---|---|---|---|
| cctgcggccc | tacgccagga | ccccgcgccg | aatactctga | ttcttcgggc tccctccaag | 60 |
| ggagtcccaa | agaccccaat | ggccaatagg | aaagtgggtt | cggtctgggc agcagtctga | 120 |
| ttggctccag | ccttcgggag | cggacccagg | ggcaagggga | gggagaggg gcggtcctgg | 180 |
| gttttggggt | gggaatcgga | ttccagctgt | ggttctctcc | ctgcgctccc gcccgcactg | 240 |
| ccacggcgga | cggccaatgg | gcgcgcggct | cggggccggc | ggcgtccggc gattggctgc | 300 |
| ggggctgtct | ggggcgggg | ccgaggcttg | aagttgaagt | gagggatcca gctgtggtgt | 360 |
| gcgcggggct | cctcgccgcc | gctttcgctc | gctcgctccg | cgtctcggcc ggaggaggag | 420 |
| gctgtggcgc | cggcgacagc | tacggcagcg | gcagccaccg | cggcggctgc ggcggcggca | 480 |
| tctccgcctc | cactcccgcc | cgggactgcc | cccactgtc | tccccgcccc tcccggacag | 540 |
| tgagcccgcg | gcggggcggg | ggaaggagcc | gccccaccc | cctccaagcc caccctaaa | 600 |
| gagatccctc | ctcccctccc | ccgccgcctg | gcgcggagcc | gggacgatgc tgaccccta | 660 |
| gatccggctc | cagctgcgcc | gcgggaagag | ggggcgcccc | tccccggacc ccgccctcc | 720 |
| gccgctgccc | ccctttcgt | tcgccctctc | ggggcggctt | cgccgaaggt agcgccgaat | 780 |
| ccggcaaccg | gagcctgggc | gcgaagcgaa | gaagccggaa | caaagtgagg gggagccggc | 840 |
| cggctggccc | gggaagcccc | aggggcgcag | gggaagcggg | actcgcgccg ggcgggttt | 900 |
| ccctgcgccc | cggcgccccg | cgggcagcat | gcccctgcgg | gcaggggag ctgggctgaa | 960 |
| ctggccctcc | cggggctca | gcttgcgccc | tagagcccac | cagatgtgcc cccgccgggg | 1020 |
| cccccgggtt | gcgtgaggac | acctcctctg | agggcgccg | cttgcccctc tccggatcgc | 1080 |
| ccggggcccc | ggctggccag | aggatggacg | aggaggagga | tggagcgggc gccgaggagt | 1140 |
| cgggacagcc | ccggagcttc | atgcggctca | acgacctgtc | ggggccggg ggcggccggg | 1200 |
| gccggggtca | gcagaaaagg | acccgggcag | cgcggactcc | gaggcggagg ggctgccgta | 1260 |
| cccggcgctg | gccccggtgg | ttttcttcta | cttgagccag | acagccgcc cgcggagctg | 1320 |
| gtgtctccgc | acggtctgta | acccatatcc | ttcggggcac | gacggccagg cgcggggtca | 1380 |
| gaaggggac | gggccgcacc | gccggggtc | ggggggaag | aagacccacc gccaggtgag | 1440 |
| tcgaagtgag | cccggagggt | aggcggatgg | gggggggct | gccagggagg ggaggggca | 1500 |
| ccagagtggg | agcggagacg | cgagcaggtc | tcgtcggtaa | cccgggctta ccccaccctgc | 1560 |
| gtacacacac | ctcagtcttc | ctgggttggg | ggggtgggga | tccaggccag gagaagagag | 1620 |
| ctgtgccccg | ctggctcgca | gctggacgcc | ctccagatgt | ggtcagggga gggtcgtcat | 1680 |
| cctccagatg | tgggaagctt | cgggagcctg | ggagctgtac | tctgcccgcg ccggttagcg | 1740 |

```
agctgggttt ggtttccgag tttggtgggg ggtgggtggg ggcggtgggg aggaagctgc    1800
ggggacggag gagggggggac cgcaatctcc tgggtttccc tccttccccc gccccaaagt    1860
ttgcggcgga ttctagatgt tggggggcgg ggaccaggtc ctggcccacc tcaccccca     1920 cctcgcgggt tggaggcaca acaaggagat tccggcggcg gctgatgtca ggggcgcaga    1980
atgagaacaa gatgtggtgg aggggagctg tctgccccg gagctgggag tggagccct     2040 ttccgctaga gcccagtgcc gcgggtgcct cctacccgat ctccattcga tgc           2093
```

<210> SEQ ID NO 107
<211> LENGTH: 327
<212> TYPE: DNA
<213> ORGANISM: Homo sapiens
<220> FEATURE:
<221> NAME/KEY: gene
<222> LOCATION: (0)...(0)
<223> OTHER INFORMATION: CDX2 CpG Island

<400> SEQUENCE: 107

```
ctcgttaatc acggaagccg ccggcctggg gctccgcacg ccagcctgtg cgggtcttcc      60
ccgcctctgc agcctagtgg gaaggaggtg ggaggaaaga aggaagaaag ggagggaggg    120
aggaggcagg ccagagggag ggaccgcctc ggaggcagaa gagccgcgag gagccagcgg    180
agcaccgcgg gctgggcgc agccacccgc cgctcctcga gtcccctcgc ccctttccct    240
tcgtgccccc cggcagcctc cagcgtcggt ccccaggcag catggtgagg tctgctcccg    300
gtccctcgcc accatgtacg tgagcta                                         327
```

<210> SEQ ID NO 108
<211> LENGTH: 1663
<212> TYPE: DNA
<213> ORGANISM: Homo sapiens
<220> FEATURE:
<221> NAME/KEY: gene
<222> LOCATION: (0)...(0)
<223> OTHER INFORMATION: EGFR CpG Island

<400> SEQUENCE: 108

```
gtccgcgggg accgggtcca gaggggcagt gctgggaacg cccctctcgg aaattaactc      60
ctcagggcac cgctcccctc ccatgcgccg ccccactccc gccggagact aggtcccgcg    120
ggggccaccg tgtccaccgc ctcgcggccg ctggccttgg gtccccgctg ctggttctcc    180
tccctcctcc tcgcattctc ctcctcctct gctcctcccg atccctcctc cgccgctgg     240 tccctcctcc tcccgccctg cctcccgcgc ctcggcccgc gcgagctaga cgtccgggca    300
gcccccggcg cagcgcggcc gcagcagcct cctccccccg cacggtgtga gcgcccgccg    360
cgccgaggcg gccggagtcc cgagctagcc ccgcggccgc cgccgcccag accggacgac    420
aggccacctc gtcgcgtccg cccgagtccc gcctcgccg ccaacgccac aaccaccgcg     480
cacggccccc tgactccgtc cagtattgat cgggagagcc ggagcgagct cttcggggag    540
cagcgatgcg accctccggg acggccgggg cagcgctcct ggcgctgctg gctgcgctct    600
gcccggcgag tcgggctctg gaggaaaaga aaggtaaggg cgtgtctcgc ggctccccgc    660
cgccccggga tcgcgccccg gacccgcag cccgcccaac cgcaccgcgc accggcttcg    720
cccgcgcccc cgcccgtcct ttcctgtttc cttgagatca cgtgcgccgc cgaccgggac    780
cgcgggagga acgggacgtt tcgttcttcg gccgggagag tctggggcgg gcggaggagg    840
agacgcgtgg gacaccgggc tgcaggccag gcggggaacg gccgccggga cctccggcgc    900
```

-continued

```
cccgaaccgc tcccaactttt cttccctcac tttccccgcc cagctgcgca ggatcggcgt    960
cagtgggcga agccgggtg ctggtgggcg cctgggccg ggtcccgca cgggctcccc       1020 gcgctgtctt cccagggcgc gacgggtcc tggcgcgcac ccgagggccg ctgcccaccc      1080
gccgagactg cctgtttagg gaagctgagg aaggaaccca aaaatacagc ctccgctcgg    1140
accccgcggg acaggcggct ttctgagagg acctccccgc ctccgcgctc cgcgcaggtc    1200
tcaaactgaa gccggcgccc gccagcctgg ccccggcccc tctccaggtc cccgcgatcc    1260
tcgttcccca gtgtggagtc gcagcctcga cctgggagct gggagaactc gtctaccacc    1320
acctgcggct cccggggagg ggtggtgctg gcggcggtta gtttcctcgt tggcaaaagg    1380
caggtggggt ccgacccgcc ccttgggcgc agaccccggc cgctcgcctc gcccggtgcg    1440
ccctcgtctt gcctatccaa gagtgccccc cactcccggg accccagctc cctccgcgcc    1500
cgcgccgaaa gccccaggct ctccttcgat ggccgcctcg cggagacgtc cgggtctgct    1560
ccacctgcag cccttcggtc gcgcctggcc ttcgcggtgg agcgggacgc ggctgtccgg    1620
ccactgcagg gggggatcgc gggactcttg agcggaagcc ccg                      1663
```

<210> SEQ ID NO 109
<211> LENGTH: 1787
<212> TYPE: DNA
<213> ORGANISM: Homo sapiens
<220> FEATURE:
<221> NAME/KEY: gene
<222> LOCATION: (0)...(0)
<223> OTHER INFORMATION: FBN1 CpG Island
<220> FEATURE:
<221> NAME/KEY: misc_feature
<222> LOCATION: (1)...(1787)
<223> OTHER INFORMATION: n = A,T,C or G

<400> SEQUENCE: 109

```
agagccgcgt ctggagtggg ctctcgacac ccagggcaag tgggggcggc agagccctct     60
cctcggtcgg cacagcagcc tctgccgcgg tcccggcctg cgacgcgccc agtcttagcc    120
tcccggcctc cggcgtctgc tgagtgtccg gcgggagagg cgcagggagc gcgctaccgg    180
gaggcgcggg cagcggggac tggttttctc tcgggccagg gcctccgggg caaccgtctc    240
cagcgcgcat tcttggtgca ggtggaacag ctttctgctc cggtagggct tcacctatcg    300
cgggagaggt taatctcgga tctaaacctc gcagccgcag agcgggctaa aaccgctact    360
ccacctcttc ccatttctcc cctccccacc tcaagacaaa aagtcccagg ccgggcagga    420
cctgatcacc tctgcctcct cccactgcgc taatcctgcg agcgagaggc cccgcaccga    480
ggcggaggct gcaagggga gtggaaaggg aggatggatg gggccggggg gtggggtggt    540
gatgagggcg acgaaggagg gggtgtcatt ttcttttttct ttctttttttt aaaaaagta    600 tttctctcgc gagaaaccgc tgcgcggacg atacttgaag aggtggggaa aggaggggggc    660 tgcgggagcc gcggcagaga ctgtgggtgc acaagcgga caggagccac agctgggaca    720
gctgcgagcg gagccgagca gtggctgtag cggccacgac tgggagcagc gccgccgcc    780 tcctcgggag tcgagccgc cgcttctcca gtgggtgcag ccggggtccg acggggtcg    840 ggcggccacc ggggctggag ctgcggccac ggaggctttt gcgtttgcgc cgnnngaggg    900
cagggacagg gactggggtg aggggctgtc ccggaacgtc caacgtggnc gctgaccct    960 cccctgcctg acagcttcct gnccggggct tcttggtgcc ggnccggcgt cagatgttcg    1020
gggggcggtg catcgcccgg agtcggcggg acggcgcgg ctgcttccag ctggcggaga    1080
gggcaggctg aggagtgggg cgttcagagc gcgcatcgcg cgcaattcgt gccgctaaaa    1140
```

```
aaaataaacc cagagagctc gcccggggct taggaccgct ggggatatgg gtactttgcg    1200
ccgcgctctt ctggcggggc ccgggaggcg agggattggc cggggctgct gcgccgggc     1260 ctgggctttc cagccagctg tggaccaaac ggtcttccct tacccaaatt aactgcgcca    1320
caggcggccg acnggttggg ctttgggaat ggggaccgcg agcttcagca tcccgatgcc    1380
ctgaaagtct ccccgcctcg ggatttgtc tctgtgttgc agctggcagg ggccgcctga     1440
agtgggagca gcgcctggag aaggcgggag gagcccggcc cggggacgg gcggcgggat     1500 agcgggaccc cggcggcgcg gtgcgcttca gggcgcagcg gcgccgcag accgagcccc     1560 gggcgcggca agaggcggcg ggagccggtg gcggctcggc atcatgcgtc gagggcgtct    1620
gctggagatc gccctgggat ttaccgtgct tttagcgtcc tacacgagcc atggggcgga    1680
cgccaatttg gaggctggga acgtgaagga aaccagagcc agtcgggcca agagaagagg    1740
cggtggagga cacgacgcgc ttaaagggta aaggaaccgg ttccctc                  1787
```

```
<210> SEQ ID NO 110
<211> LENGTH: 810
<212> TYPE: DNA
<213> ORGANISM: Homo sapiens
<220> FEATURE:
<221> NAME/KEY: gene
<222> LOCATION: (0)...(0)
<223> OTHER INFORMATION: GPR37 CpG Island

<400> SEQUENCE: 110
tcccgccccg cacccgcccc tagcccgggc tcggggacct gtcaggctgg tttcgacagc     60
tggggaatta acctgtcccg cccatcccta gcctcgagcc gcgcaggctc cgcgcctccg    120
cccttgttcc ctcccagctc ctccgagtgg aagccgctac aaatggcttg aatgaaacgt    180
gtgtgggttt agtgagtggt gaaccaccag gggatcccgt ctccccacaa accagtatct    240
ctccgaggag gaggcgaagg agtgggagga ggcaacgagc cgagagtcga gcttcgcggg    300
cgcgcgcagc ggctggagcg cggggggcgag gccgggccac ctccccttcc cggccgcgca    360
ctgcctggcc cgcggcggtt ccaggcacca cccttcccgt ccgggctgag cccgctgtgg    420
cagtgactag ctcccgcggc tagcggcact gtccaccgac gagcggcgcc ctcttctccc    480
ccttctcccc acgatttcct tctctgcggc ggcacgccgt ccagcagcct gcttcgcccc    540
gtcgtcaact ttgagctgga ggagaagcaa ctttggcagt ggccgcgggg ttggaatccc    600
gcttctcctc ggcagcagta ggctcgcaag tcgctgggt taggtggggc aagagttccg    660
ccggcgcatc agcgctgctt cggactgttt gcaacgtgtt tccagcgagc tgggagcggg    720
gttgtgactg cgagtcgtct ggggagggg gacttgtttt tcttttcctc tagagacctc    780
ggcttgcaac tggatcaaac gctgtcgaaa                                    810
```

```
<210> SEQ ID NO 111
<211> LENGTH: 550
<212> TYPE: DNA
<213> ORGANISM: Homo sapiens
<220> FEATURE:
<221> NAME/KEY: gene
<222> LOCATION: (0)...(0)
<223> OTHER INFORMATION: HSPA6 CpG Island

<400> SEQUENCE: 111
tgtattcgca tggtaacata tcttcggtct tcctgccgct gggctctcag cggccctcca     60
aggcagcccg caggcccgtg ctcgcctcag ggatcctcca cagccccggg gagaccttgc    120
```

```
ctctaaagtt gctgcttttg cagctctgcc acaaccgcgc gtcctcagag ccagccggga      180
ggagctagaa ccttccccgc gtttctttca gcagccctga gtcagaggcg ggctggcctt      240
gcaagtagcc gcccagcctt cttcggtctc acggaccgat ccgcccgaac cttctcccgg      300
ggtcagcgcc gcgctgcgcc gcccggctga ctcagcccgg gcgggcgggc gggaggctct      360
cgactgggcg ggaaggtgcg ggaaggttcg cggcggcggg gtcggggagg tgcaaaagga      420
tgaaaagccc gtggacggag ctgagcagat ccggccgggc tggcggcaga gaaaccgcag      480
ggagagcctc actgctgagc gcccctcgac gcgggcggca gcagcctccg tggcctccag      540
catccgacaa                                                             550

<210> SEQ ID NO 112
<211> LENGTH: 278
<212> TYPE: DNA
<213> ORGANISM: Homo sapiens
<220> FEATURE:
<221> NAME/KEY: gene
<222> LOCATION: (0)...(0)
<223> OTHER INFORMATION: IQGAP2 CpG Island

<400> SEQUENCE: 112
agagttcact tttacttcag tgtcagcgcg cggcggccgt ggctggctct ggcgagagag       60
caccgaggga gtgggtcgca gatcttcggg cggctagggg aaatcggcga gaggcgggat      120
ccgagcgcgc cggcggggcg cagagcccgc gagcctggcc agcgagggta gccgcggggg      180
gcgcgccccg ggcgggcccc cggagacgcg caggatgcca cacgaagagc tgccgtcgct      240
gcagagaccc cgctatggct ctattgtgga cgatgaaa                              278

<210> SEQ ID NO 113
<211> LENGTH: 1461
<212> TYPE: DNA
<213> ORGANISM: Homo sapiens
<220> FEATURE:
<221> NAME/KEY: gene
<222> LOCATION: (0)...(0)
<223> OTHER INFORMATION: KL CpG Island

<400> SEQUENCE: 113
ctcgaaagag gggcgcgggt gggcgcgtct ccccgcgagc atctcaccta aggggggaatc      60 cctttcagcg cacggcgaag ttccccctcg gctgtcccac ctggcagtcc ctctaggatt     120
tcggccagtc cctaattggc tccagcaatg tccagccgga gcttctttgg gcctccgagt     180
gggagaaaag tgagagcagg tgcttcccca gcggcgcgct ccgctagggc ccggcaggat     240
cccgccccca agtcgggaaa agttggtcgg cgccttttct ccccgacgaa gccgctccag     300
ggctgctctc agaggacgcg cggcaggcaa agagaatgaa cctgagcgtc cacgaaacgt     360
cctgcacggc tcccgggagc tgggagaaac aggtgccttt ctccgacgtc cgcgggcgac     420
gcctgccgca ccttgcccgc tgccgcgccc tcccgggca ccctcgccc tcggcgcccc      480 tgcccccacc cccagtgcca gggcggaggc agtcccggct cgcaggtaat tattgccagc     540
ggagcccgcg ggggagcggg ggtgggcgcg cggcggtgg gcgggcgggc gcggcggggc     600
gcgggcataa agggcgcgg cgcgggccc cggagcctgg ctcccgcgca gcatgcccgc      660
cagcgccccg ccgcgccgcc cgcggccgcc gccgcgtcg ctgtcgctgc tgctggtgct     720
gctgggcctg ggcggccgcc gcctgcgtgc ggagccgggc gacggcgcgc agacctgggc     780
ccgtttctcg cggcctcctg cccccgaggc gcgggcctc ttccagggca ccttcccga      840 cggcttcctc tgggccgtgg gcagcgccgc ctaccagacc gagggcggct ggcagcagca     900
```

-continued

```
cggcaagggt gcgtccatct gggacacgtt cacccaccac ccctggcac cccgggaga    960 ctcccggaac gccagtctgc cgttgggcgc cccgtcgccg ctgcagcccg ccaccgggga   1020
cgtagccagc gacagctaca acaacgtctt ccgcgacacg gaggcgctgc gcgagctcgg   1080
ggtcactcac taccgcttct ccatctcgtg ggcgcgagtg ctccccaatg gcagcgcggg   1140
cgtccccaac cgcgaggggc tgcgctacta ccggcgcctg ctggagcggc tgcgggagct   1200
gggcgtgcag cccgtggtca ccctgtacca ctgggacctg ccccagcgcc tgcaggacgc   1260
ctacggcggc tgggccaacc cgccctggc cgaccacttc agggattacg cggagctctg    1320
cttccgccac ttcggcggtc aggtcaagta ctggatcacc atcgacaacc cctacgtggt   1380
ggcctggcac ggctacgcca ccgggcgcct ggccccggc atccggggca gcccgcggct    1440
cgggtacctg gtggcgcaca a                                              1461

<210> SEQ ID NO 114
<211> LENGTH: 249
<212> TYPE: DNA
<213> ORGANISM: Homo sapiens
<220> FEATURE:
<221> NAME/KEY: gene
<222> LOCATION: (0)...(0)
<223> OTHER INFORMATION: PAR2 CpG Island

<400> SEQUENCE: 114
cccggggcgt ggcctcccgc aggtgagtac gctgctcctt cggtttccct gaaacctaac    60
ccgccctggg gaggcgcgca gcagaggctc cgattcgggg caggtgagag gctgactttc   120
tctcggtgcg tccagtggag ctctgagttt cgaatcggcg gcggcggatt ccccgcgcgc   180
ccggcgtcgg ggcttccagg aggatgcgga gccccagcgc ggcgtggctg ctgggggccg   240
ccatcctgc                                                             249

<210> SEQ ID NO 115
<211> LENGTH: 709
<212> TYPE: DNA
<213> ORGANISM: Homo sapiens
<220> FEATURE:
<221> NAME/KEY: gene
<222> LOCATION: (0)...(0)
<223> OTHER INFORMATION: PITX2 CpG Island

<400> SEQUENCE: 115
agtccgtgct cctgctcctc ggttggctcc taagtgcccc gccaggtccc ctctcctttc     60
gctctcccgg ctccggctcc cgactcttcg gcccgctggc atctgcttcc ctcccctgcc   120
tcgtttctcg tcgcccctgc tcgctccccc cggcgctcgc ccgggcgctg tgctcgctcc   180
tggatcgcca gccgcgcagc cgggctcggc cggccgcccg cgcgccactg tgcagtggag   240
tttggtggaa tctctgctga cgtcacgtca ctccccacac ggagtaggag cagagggaag   300
agagagggat gagagggagg gagaggagag agagtgcgag accgagcgag aaagctggag   360
aggagcagaa agaaactgcc agtggcggct agatttcgga ggcccagtg cacccgtgga     420 ctccttcgga acttggcacc ctcaggagcc ctgcagtcct ctcaggcccg gctttcgggc   480
gcttgccgtg cagccggagg ctcggctcgc tggaaatcgc cccgggaagc agtgggacgc   540
ggagacagca gctctctccc ggtagccgat aacggggaaa tggagaccaa ctgccgcaaa   600
ctggtgtcgg cgtgtctgca attagagaaa gataaaagcc agcaggggaa gaatgaggac   660
gtgggcgccg aggacccgtc taagaagaag cggcaaaggc ggcagcgga                709
```

<210> SEQ ID NO 116
<211> LENGTH: 1496
<212> TYPE: DNA
<213> ORGANISM: Homo sapiens
<220> FEATURE:
<221> NAME/KEY: gene
<222> LOCATION: (0)...(0)
<223> OTHER INFORMATION: PTCA CpG Island
<220> FEATURE:
<221> NAME/KEY: misc_feature
<222> LOCATION: (1)...(1496)
<223> OTHER INFORMATION: n = A,T,C or G

<400> SEQUENCE: 116

```
gcggccgcag cggcagcagc gcccgccgtg tgagcagcag cagcggctgg tctgtcaacc      60
ggagcccgag cccgagcagc ctgcggccag cagcgtcctc gcaagccgag cgcccaggcg     120
cgccaggagc ccgcagcagc ggcagcagcg cgccgggccg cccgggaagc ctccgtcccc     180
gcggcggcgg cggcggcggc ggcaacatgg cctcggctgg taacgccgcc gagccccagg     240
accgcggcgg cggcggcagc ggctgtatcg gtgccccggg acggccggct ggaggcggga     300
ggcgcagacg gacgggggggg ctgcgccgtg ctgccgcgcc ggaccgggac tatctgcacc     360
ggcccagcta ctgcgacgcc gccttcgntn nggagnagat ttnccanggn nggcatttca     420
gactntntcn ttcccacttt ntcttcccnt acctntaact cntngggat cgcccccgcc     480
acacacaaac acacacactn tcttcctctn tntctcacac acaacacaca cactcactca     540
cacntctnca ggaaaagcag cagacaaatg gggattgaaa aattcaaacc ctccctctgg     600
tnntgggagg aaagggctgt ctgaggtccg caggggggtgg aggtgtgtgt gtgtgcgtgt     660
gtgtgtgtgn anacacacgc cctccctggt gtgccttttc cggagcactg gaaagccgtc     720
cacggcggac cacctcaagg gcggccgcgc ggtcgtagcg gtagtagcgt tcgtcgtgtg     780
agtagtagta gcggttggtt tgttaatcgg agttcgagtt cgagtagttt gcggttagta     840
gcgtttcgt aagtcgagcg tttaggcgcg ttaggagttc gtagtagcgg tagtagcgcg     900
tcgggtcgtt cgggaagttt tcgttttcgc ggcggcggcg gcggcggcgg taatatggtt     960
tcggttggta acgtcgtcga gttttaggat cgcggcggcg gcggtagcgg ttgtatcggt    1020
gtttcgggac ggtcggttgg aggcgggagg cgtagacgga cgggggggtt gcgtcgtgtt    1080
gtcgcgtcgg atcgggatta tttgtatcgg tttagttatt gcgacgtcgt tttcgntnng    1140
gagnagattt nttanggnng gtattttaga ttntntnttt tttattttnt tttttttntat    1200
ttntaatttn tnggggatcg ttttcgttat atataaatat atatattntt ttttttntn    1260
ttttatatat aatatatata tttatttata tnttttntagg aaaagtagta gataaatggg    1320
gattgaaaaa tttaaatttt tttttttggtn ntgggaggaa agggttgttt gaggttcgta    1380
gggggtggag gtgtgtgtgt gtgcgtgtgt gtgtgtgnan atatacgttt tttttggtgt    1440
gttttttcg gagtattgga aagtcgttta cggcggatta ttttaagggc ggtcgt        1496
```

<210> SEQ ID NO 117
<211> LENGTH: 701
<212> TYPE: DNA
<213> ORGANISM: Homo sapiens
<220> FEATURE:
<221> NAME/KEY: gene
<222> LOCATION: (0)...(0)
<223> OTHER INFORMATION: PTCHB CpG Island
<220> FEATURE:
<221> NAME/KEY: misc_feature
<222> LOCATION: (1)...(701)
<223> OTHER INFORMATION: n = A,T,C or G

<400> SEQUENCE: 117

```
gcggccgcgg cactgtcctg ccccgtgccc cctgccctga acttcttcct cctgcgcccc      60
tgcccctatt tgcagcctaa actcctgtac ggctgccaca tttcttaaca tcttggaggg     120
ggaggcggag tggagagagg cggagagagg aaggggggag ggagccgaaa taaaggtggt     180
ttcctttttt ggcagccagt tttggttttg ttgagcatga aatctctgct cccttaaaaa     240
attattctcg gaaaaagata tccccccgt tttccaggtt ttgagccgcc tctccttagg     300
gcctggtcgg gggaggaaaa gttgtaaaca aattgccacc ttaaattcgc ggtgcgantc     360
tgcggagctg ccgggttcat tgtgtttacg aggctcgctg aaatgtgtgg aatccaggga    420
aggcgagcac ccagacgggg gcccgccggg gccgcggcca cgccggggga aatgccgcgc    480
cggggagcag catgcgccgg cctgagccct tccctttgca ctcggctgtt ttttacgttt    540
aaccagaaag gaagggagag gagggaaaga tccatgtggc tgccctcttc cgatcacaaa    600
tattgtcgta agttgcagct ggctgcccca nttcctaatt cagctcacac agcntntccc    660
cacgctatgg aaatgcgtcg ggagtgaact ccggcggccg c                        701
```

<210> SEQ ID NO 118
<211> LENGTH: 273
<212> TYPE: DNA
<213> ORGANISM: Homo sapiens
<220> FEATURE:
<221> NAME/KEY: gene
<222> LOCATION: (0)...(0)
<223> OTHER INFORMATION: SDC1 CpG Island

<400> SEQUENCE: 118

```
ggagaggtgc gggccgaatc cgagccgagc gagaggaatc cggcagtaga gagcggactc      60
cagccggcgg accctgcagc cctcgcctgg gacagcggcg cgctgggcag gcgcccaaga    120
gagcatcgag cagcggaacc cgcgaagccg gcccgcagcc gcgacccgcg cagcctgccg    180
ctctcccgcc gccggtccgg gcagcatgag gcgcgcggcg ctctggctct ggctgtgcgc    240
gctggcgctg agcctgcagc tggccctgcc gca                                 273
```

<210> SEQ ID NO 119
<211> LENGTH: 751
<212> TYPE: DNA
<213> ORGANISM: Homo sapiens
<220> FEATURE:
<221> NAME/KEY: gene
<222> LOCATION: (0)...(0)
<223> OTHER INFORMATION: SDC4 CpG Island

<400> SEQUENCE: 119

```
agtaggagcc ggcgggctcg ggcagggcgg gtcccttggg gtttccaact ccgcgggcgg      60
gcgcagtgcc ccgcaggcct cgcttccact ggggaattcc gggcgggtg cgggcggcgg    120
ggcgggggcg ggccggggcg gggccggtag gccgcctata agatgggtgg cgcgcccgcc    180
cggggccact cgccgcagcc tgcgcgcctt ctccagtccg cggtgccatg gccccgccc    240
gtctgttcgc gctgctgctg ttcttcgtag gcggagtcgc cgagtcggtg ggtgcttgga    300
ggttcccggg ctggggcga agcggggcg caggccggtg cctcctttgt tcgtcggagc    360
gtgggatggg gggggcaga tcgggggtac gctacccca accggacacc gaggcccggg    420
aaactttgtt ggaaactttg ctccggggtc acgggccagc ctcgggatg gcttcacgcg    480
ccgtgcgccc ctcgcctgtt gctcttcccg cctccccggg cctcagcccc gccgcgggct    540
```

-continued

```
acgggctcgt tagtgactaa gccggtgtca actcttcaac tcccacaccc tcgtcccttc    600
cctggtgacc ctggggcagg cttggagcgc tgaatcccct cctcgctctc ggggcgccca    660
gagcagacag ctttaggatc cgagatggcc ctgggggtcg ggggctgcg tgtactcgga     720 aggggggaggg ttttagggtt gtgcgaggcc c                                  751
```

<210> SEQ ID NO 120
<211> LENGTH: 673
<212> TYPE: DNA
<213> ORGANISM: Artificial Sequence
<220> FEATURE:
<223> OTHER INFORMATION: DNA fragment termed MINT31
<220> FEATURE:
<221> NAME/KEY: misc_feature
<222> LOCATION: (1)...(673)
<223> OTHER INFORMATION: n = A,T,C or G

<400> SEQUENCE: 120

```
cccgggcct ctatcctggc gggaagggca ggccgacccg gcagactgcg gcctctcggg      60
agggaagaag gtgtcagacg cgcggagcaa ccataaatag ccccccttc ccagaagacg    120 gcacggggtt caagactcag gcgccgcata ctcagaatga gagcagagac tcccgccagg    180
aaaaaagggc acttagggga tctgctcatt aacatgaaat gcaaatgagc ccgcccggcc    240
tcatttacac aactctgtgc atggattcgg cgaaagggca accagggaga cgacggcgca    300
gcagccactc tgccacttcc cccatccct cccccccatc ggccggggcg ggaactgaga     360 cgacccaac cctctgcggc ggcgggaggt gcgcggggc tgcgtgggtg gtgcagcctt      420
aggggagtga acaacgccca ggggtgatgg cctcagcaaa gtgaggggtg gtgatggagg    480
tcatccgacc catcccgccg cctctccgca gtggcgcaag cgcccaaaaa tctccggaga    540
nggaactgag tgacccacta ggttccgccg tgtctacctc tcgcagatgt tggggaagtg    600
cttcccggcg tctaatcctc gctgttcccc cctccaccgg cgcccagcac acccgcggcg    660
ctccgctccc ggg                                                       673
```